United States Patent
McMichael et al.

(10) Patent No.: US 7,514,087 B2
(45) Date of Patent: *Apr. 7, 2009

(54) METHODS AND REAGENTS FOR IMMUNIZATION WHICH GENERATE A CD8 T CELL IMMUNE RESPONSE

(75) Inventors: Andrew McMichael, Beckley (GB);
Adrian V. S. Hill, Old Headington (GB);
Sarah C. Gilbert, Headington (GB);
Jörg Schneider, Barton (GB);
Magdalena Plebanski, Melbourne (AU);
Tomas Hanke, Old Marston (GB);
Geoffrey L. Smith, Oxford (GB); Tom Blanchard, Banjul (GM)

(73) Assignee: Oxxon Therapeutics Limited, Oxford (GB)

( * ) Notice: Subject to any disclaimer, the term of this patent is extended or adjusted under 35 U.S.C. 154(b) by 88 days.

This patent is subject to a terminal disclaimer.

(21) Appl. No.: 10/833,439

(22) Filed: Apr. 28, 2004

(65) Prior Publication Data

US 2004/0175365 A1   Sep. 9, 2004

Related U.S. Application Data

(60) Continuation of application No. 10/686,943, filed on Oct. 16, 2003, which is a continuation of application No. 09/454,204, filed on Dec. 9, 1999, now Pat. No. 6,663,871, which is a continuation of application No. PCT/GB98/01681, filed on Jun. 9, 1998, application No. 10/833,439, which is a continuation of application No. 10/653,624, filed on Sep. 2, 2003, which is a division of application No. 09/454,204, filed on Dec. 9, 1999, now Pat. No. 6,663,871, which is a continuation of application No. PCT/GB98/01681, filed on Jun. 9, 1998.

(30) Foreign Application Priority Data

Jun. 9, 1997   (GB) ................................. 9711957.2

(51) Int. Cl.
*A61K 39/275* (2006.01)
*A61K 39/12* (2006.01)
*A61K 31/70* (2006.01)
*C07H 21/02* (2006.01)
*A01N 43/04* (2006.01)

(52) U.S. Cl. ................ 424/232.1; 424/199.1; 536/23.1; 514/44

(58) Field of Classification Search .............. 424/199.1; 435/455
See application file for complete search history.

(56) References Cited

U.S. PATENT DOCUMENTS

| 4,053,582 | A | 10/1977 | Stickl |
| 4,748,019 | A | 5/1988 | Lysons |
| 5,110,587 | A | 5/1992 | Paoletti et al. |
| 5,185,146 | A | 2/1993 | Altenburger |
| 5,225,336 | A | 7/1993 | Paoletti |
| 5,453,364 | A | 9/1995 | Paoletti |
| 5,462,734 | A | 10/1995 | Letchworth, III et al. |
| 5,766,597 | A | 6/1998 | Paoletti et al. |
| 5,846,546 | A | 12/1998 | Hurwitz et al. |
| 6,103,244 | A | 8/2000 | Dorner et al. |
| 6,355,252 | B1 | 3/2002 | Smith et al. |
| 6,663,871 | B1 | 12/2003 | McMichael et al. |
| 7,273,605 | B2 | 9/2007 | Laidlaw et al. |
| 2001/0036928 | A1* | 11/2001 | Chamberlain et al. ......... 514/44 |
| 2003/0138454 | A1 | 7/2003 | Hill et al. |
| 2004/0018177 | A1 | 1/2004 | Hill et al. |
| 2004/0131594 | A1 | 7/2004 | McMichael et al. |
| 2004/0142002 | A1 | 7/2004 | Smith et al. |
| 2004/0171272 | A1 | 9/2004 | McMichael et al. |
| 2004/0197349 | A1 | 10/2004 | McMichael et al. |
| 2004/0213799 | A1 | 10/2004 | McMichael et al. |
| 2005/0025747 | A1 | 2/2005 | Laidlaw et al. |
| 2005/0175627 | A1 | 8/2005 | Schneider |

FOREIGN PATENT DOCUMENTS

| CN | 1 324 661 A | 12/2001 |
| EP | 0 638 316 A1 | 2/1995 |
| EP | 0 753 581 A1 | 1/1997 |
| EP | 0 517 292 B1 | 2/2000 |
| WO | WO 92/22641 A1 | 12/1992 |
| WO | WO 93/03145 A1 | 2/1993 |
| WO | WO 96/26271 | 8/1996 |
| WO | WO 97/39771 | 10/1997 |
| WO | WO 98/04728 | 2/1998 |
| WO | WO 98/04728 A1 | 2/1998 |
| WO | WO 98/56919 A2 | 12/1998 |
| WO | WO 99/41383 A1 | 8/1999 |
| WO | WO 01/02607 A1 | 1/2001 |
| WO | WO 01/14416 A2 | 3/2001 |
| WO | WO 01/21201 A2 | 3/2001 |

(Continued)

OTHER PUBLICATIONS

Thomson, S. Delivery of multiple CD8 cytotoxic T cell epitopes by DNA vaccination. The Journal of Immunology 1998, vol. 160, p. 1717-1723.*

(Continued)

*Primary Examiner*—Bruce Campell
*Assistant Examiner*—Louise Humphrey
(74) *Attorney, Agent, or Firm*—Hamilton, Brook, Smith & Reynolds, P.C.

(57) ABSTRACT

New methods and reagents for vaccination are described which generate a CD8 T cell immune response against malarial and other antigens such as viral and tumor antigens. Novel vaccination regimes are described which employ a priming composition and a boosting composition, the boosting composition comprising a non-replicating or replication-impaired pox virus vector carrying at least one CD8 T cell epitope which is also present in the priming composition.

29 Claims, 18 Drawing Sheets

FOREIGN PATENT DOCUMENTS

| | | |
|---|---|---|
| WO | WO 01/85932 A2 | 11/2001 |
| WO | WO 01/85932 A3 | 11/2001 |
| WO | WO 02/24224 A2 | 3/2002 |
| WO | WO 02/068654 A2 | 9/2002 |
| WO | WO 02/068654 A3 | 9/2002 |
| WO | WO 2005/026370 A2 | 3/2005 |
| WO | WO 2005/030964 A1 | 4/2005 |
| WO | WO 2006/061643 A1 | 6/2006 |
| WO | WO 2006/120474 A2 | 11/2006 |
| WO | WO 2006/125983 A1 | 11/2006 |

OTHER PUBLICATIONS

Conry, R. Safety and immunogenicity of a DNA vaccine encoding carcinoembryonic antigen and hepatitis B surface antigen in colorectal carcinoma patients. Clinical Cancer Research Sep. 2002, vol. 8, p. 2782-2787.*

Ramarathinam L. Mutliple lineages of tumors express a common tumor antigen, P1A, but they are not cross-protected. The Journal of Immunology 1995, vol. 155: 5323-5329.*

Ahlers, J.D., et al., "Cytokine-in-Adjuvant Steering of the Immune Response Phenotype to HIV-1 Vaccine Constructs," *The Journal of Immunology*, 158(8):3947-3958 (1997).

Allen, T.M. and Watkins, D.I., SIV and SHTV CTL Epitopes Identified in Macaques [online], Dec. 1998. Retrieved from the Internet <URL:http://hiv-web.lanl.gov/content/hiv-db/COMPENDIUM/1998/III/Allen98.pdf>.

An, L.-L., and Whitton, J.L., "A Multivalent Minigene Vaccine, Containing B-Cell, Cytotoxic T-Lymphocyte, and $T_h$ Epitopes from Several Microbes, Induces Appropriate Responses In Vivo and Confers Protection against More than One Pathogen," *Journal of Virology*, 71(3): 2292-2302 (1997).

Austyn, J.M. and Wood, K.J., "An Overview of Immune Responses," In *Principles of Cellular and Molecular Immunology*, (NY: Oxford University Press Inc.), pp. 42-44 (1993).

Bakker, A.B.H., et al., "Identification of a Novel Peptide Derived from the Melanocyte-Specific GP100 Antigen as the Dominant Epitope Recognized by an HLA-A2.1-Restricted Anti-Melanoma CTL Line," *Int. J. Cancer*, 62: 97-102 (1995).

Bergmann, C.C., et al., "Flanking Residues Alter Antigenicity and Immunogenicity of Multi-Unit CTL Epitopes," *The Journal of Immunology*, 157(8): 3242-3249 (1996).

Bukowski, J.F., et al., "Natural Killer Cell Depletion Enhances Virus Synthesis and Virus-Induced Hepatitis In Vivo," *The Journal of Immunology*, 131(3): 1531-1538 (1983).

Casares, N., et al., "$CD4^+/CD25^+$ Regulatory Cells Inhibit Activation of Tumor-Primed $CD4^+$ T Cells with IFN-γ-Dependent Antiangiogenic Activity, as well as Long-Lasting Tumor Immunity Elicited by Peptide Vaccination," *The Journal of Immunology*, 171(11): 5931-5939 (2003).

Cox, W.I., et al., Induction of Cytotoxic T Lymphocytes by Recombinant Canarypox (ALVAC) and Attenuated Vaccinia (NYVAC) Viruses Expressing the HIV-1 Envelope Glycoprotein, *Virology*, 195: 845-850 (1993).

Egan, M.A., et al., "Use of Major Histocompatibility Complex Class I/Peptide/β2M Tetramers To Quantitate $CD8^+$ Cytotoxic T Lymphocytes Specific for Dominant and Nondominant Viral Epitopes in Simian-Human Immunodeficiency Virus-Infected Rhesus Monkeys," *Journal of Virology*, 73(7): 5466-5472 (1999).

Eisenlohr, L.C., et al., "Flanking Sequences Influence the Presentation of an Endogenously Sythesized Peptide to Cytotoxic T Lymphocytes," *The Journal of Experimental Medicine*, 175: 481-487 (1992).

Feng, C.G., et al., "Induction of $CD^{*+}$ T-lymphocyte Responses to a Secreted Antigen of *Mycobacterium tuberculosis* by an Attenuated Vaccinia Virus," *Immunology and Cell Biology*, 79: 569-575 (2001).

Gherardi, M.M., et al., "Prime Boost Immunization Schedules Based on Influenza Virus and Vaccinia Virus Vectors Potentiate Cellular Immune Responses Against Human Immunodeficiency Virus Env Protein Systemically and in the Genitorectal Draining Lymph Nodes," *The Journal of Virology*, 77(12): 7048-7057 (2003).

Gönczöl, E., et al., "Preclinical Evaluation of an ALVAC (canarypox)-human Cytomegalovirus Glycoprotein B Vaccine Candidate," *Vaccine*, 13(12): 1080-1085 (1995).

HIV CTL Epitopes Table 2 p24. [online], Dec. 1996. Retrieved from the Internet <URL:http://hiv-web.lanl.gov/content/immunology/pdf/1996/CTL/TABLES/p24.pdf>.

HTV CTL Epitopes Table 3: p24 [online], Dec. 1999. Retrieved from the Internet <URL:http://hiv-web.lanl.gov/content/immunology/pdf/1999/1/tables/p24.pdf>.

HTV CTL Epitopes Table 4: Pol [online], Dec. 1997. Retrieved from the Internet <URL:http://hiv-web.lanl.gov/content/hiv-db/immunology/PDF/1997/CTL/tables/pol.pdf>.

HTV CTL Epitopes Table 6 gp120. [online], Dec. 1996. Retrieved from the Internet <URL:http://hiv-web-lanl.gov/content/immunology/pdf/1996/CTL/TABLES/gp120.pdf>.

HTV CTL Epitopes Table 7 gp41. [online], Dec. 1996. Retrieved from the Internet <URL:http://hiv-web.lanl.gov/content/immunology/pdf/1996/CTL/TABLES/gp41.pdf>.

HTV CTL Epitopes Table 8 Nef. [online], Dec. 1996. Retrieved from the Internet <URL:http://hiv-web.lanl.gov/content/immunology/pdf/1996/CTL/TABLES/nef.pdf>.

Hu, S.-L., et al., "Protection of Macaques Against SIV Infection by Subunit Vaccines of SIV Envelope Glycoprotein gp160," *Science*, 255: 456-459 (1992).

Hunter, C.A., "How are NK Cell Responses Regulated During Infection?," *Experimental Parasitology*, 84: 444-448 (1996).

Janeway, C.A., et al., "General Properties of Armed Effector T Cells," In *Immuno Biology*, (NY: Garland Publishing a member of the Taylor & Francis Group) p. 319 (2001).

Konishi, E., et al., "Induction of Japanese Encephalitis Virus-specific Cytotoxic T Lymphocytes in Humans by Poxvirus-based JE Vaccine Candidates," *Vaccine*, 16(8): 842-849 (1998).

Konishi, E., et al., "Poxvirus-Based Japanese Encephalitis Vaccine Candidates Induce JE Virus-Specific $CD8^+$ Cytotoxic T Lymphocytes in Mice," *Virology*, 227: 353-360 (1997).

Kuby, J., "Cell-Mediated and Humoral Effector Responses," In *Immunology*, (NY: W. H. Freeman and Company) pp. 379-412 (1997).

Linnemeyer, P.A., "The Immune System—An Overview," [online] Nov. 1993 [retrieved on Apr. 12, 2006]. Retrieved from the Internet <URL:http://www.thebody.com/step/immune.html>.

Malcherek, G., et al., "Supermotifs Enable Natural Invariant Chain-derived Peptides to Interact with Many Major Histocompatibility Complex-Class II Molecules," *J. Exp. Med.*, 181: 527-536 (1995).

Martin, R.M. and Lew, A.M., "Is IgG2a a Good Th1 Marker in Mice?" *Immunology Today*, 19:49 (1998).

Müller, H.M., et al., "Thrombospondin Related Anonymous Protein (TRAP) of *Plasmodium falciparum* in Parasite-Host Cell Interactions," *Parassitologia* 35(*Suppl.*): 69-72 (1993).

Narvaiza, I., et al., Intratumoral Coinjection of Two Adenoviruses, One Encoding the Chemokine IFN-γ-Inducible Protein-10 and Another Encoding IL-12, Results in Marked Antitumoral Synergy, *The Journal of Immunology*, 164(6): 3112-3122 (2000).

Ojcius, D. M., et al., "Is Antigen Processing Guided by Major Histocompatibility Complex Molecules?," *FASEB J.*, 8: 974-978 (1994).

Okuda, K., et al., "Induction of Potent Humoral and Cell-Mediated Immune Responses Following Direct Injection of DNA Encoding the HIV Type 1 *env* and *rev* Gene Products," *Aids Research and Human Retroviruses*, 11(8): 933-943 (1995).

Ramirez, J.C., et al., "Biology of Attenuated Modified Vaccinia Virus Ankara Recombinant Vector in Mice: Virus Fate and Activation of B- and T-Cell Immune Responses in Comparison with the Western Reserve Strain and Advantages as a Vaccine," *Journal of Virology*, 74(2): 923-933 (2000).

Reusser, P., et al., "Cytomegalovirus-Specific T-Cell Immunity in Recipients of Autologous Peripheral Blood Stem Cell or Bone Marrow Transplants," *Blood*, 89(10): 3873-3879 (1997).

Romero, P., et al., "Cloned Cytotoxic T Cells Recognize an Epitope in the Circumsporozoite Protein and Protect Against Malaria," *Nature*, 341: 323-326 (1989).

Takada, K., et al., "Definition of an Epitope on Japanese Encephalitis Virus (JEV) Envelope Protein Recognized by JEV-specific Murine CD8+ Cytotoxic T Lymphocytes," *Arch Virol.*, 145: 523-534 (2000).

Vasmatzis, G., et al., "Computational Determination of Side Chain Specificity for Pockets in Class I MHC Molecules," *Molecular Immunology*, 33(16): 1231-1239 (1996).

Whitton, J.L., et al., "A "String-of-Beads" Vaccine, Comprising Linked Minigenes, Confers Protection from Lethal-Dose Virus Challenge," *Journal of Virology*, 67(1): 348-352 (1993).

Yang, Y., et al., "Upregulation of Class I Major Histocompatibility Complex Antigens by Interferon γ is Necessary for T-cell-mediated Elimination of Recombinant Adenovirus-infected Hepatocytes In Vivo," *Proc. Natl. Acad. Sci. USA*, 92: 7257-7261 (1995).

Yellen-Shaw, A.J., et al., "Point Mutation Flanking a CTL Epitope Ablates In Vitro and In Vivo Recognition of a Full-Length Viral Protein," *The Journal of Immunology*, 158(7): 3227-3234 (1997).

Zhu, M., et al., "Specific Cytoltic T-Cell Responses to Human CEA from Patients Immunized with Recombinant Avipox-CEA Vaccine," *Clinical Cancer Research*, 6: 24-33 (2000).

Ada, G., "Do Cytotoxic T Lymphocytes Clear Some HIV/SIV Infections?," *J. Med. Primatol.* 25(3):158-162 (Jun. 1996).

Aidoo, M., et al., "Identification of Conserved Antigenic Components For a Cytotoxic T Lymphocyte-Inducing Vaccine Against Malaria," *Lancet* 345(8956):1003-1007 (Apr. 22, 1995).

Aidoo, M., et al., "Recombinant Vaccinia Viruses for the Characterization of *Plasmodium falciparum*-specific Cytotoxic T Lymphocytes: Recognition of Processed Antigen Despite Limited Re-Stimulation Efficacy," *Intl. Immunol.* 9(5):731-737 (Jan. 1997).

Allsopp, C.E.M., et al., "Comparison of Numerous Delivery Systems for the Induction of Cytotoxic T Lymphocytes By Immunization," *Eur. J. Immunol.* 26:1951-1959 (1996).

Blanchard, T., et al., "Future Vaccines for HIV," *Lancet* 348(9043):1741 (Dec. 1996).

Blanchard, T.J., et al., "Modified Vaccinia Virus Ankara Undergoes Limited Replication in Human Cells and Lacks Several Immunomodulatory Proteins: Implications for Use as a Human Vaccine," *J. Gen. Virol.* 79:1159-1167 (1998).

Carroll, M.W., et al., "Highly Attenuated Modified Vaccinia Virus Ankara (MVA) as an Effective Recombinant Vector: A Murine Tumor Model," *Vaccine* 15(14):387-394 (1997).

Chamberlain, R.S., et al., "Use of Multiple Vaccination Vectors for the Generation of CTL Against a Model Tumor Antigen," *Proceedings of the Annual Meeting of the American Association for Cancer Research* (Washington, Apr. 20-24, 1996, 37, Abstract No. 3263).

Doolan, D.L., "The Complexity of Protective Immunity Against Live-Stage Malaria," *J. Immunol.*, 165(3): 1453-1462 (2000).

Doolan, D.L., et al., "Circurmventing Genetic Restriction of Protection against Malaria with Multigene DNA Immunization: CD8+ T Cell-, Interferon γ-, and Nitric Oxide-Dependent Immunity," *J. Exp. Med.* 183(4):1739-1746 (Apr. 1996).

Fuller, D.H., et al., "Gene Gun-Based Nucleic Acid Immunization Alone or in Combination with Recombinant Vaccinia Vectors Suppresses Virus Burden in Rhesus Macaques Challenged with a Heterologous SIV," *Immunol. Cell Biol.* 75(4):389-396 (Aug. 1997).

Fuller, D.H., et al., "Enhancement of Immunodeficiency Virus-Specific Immune Responses in DNA-Immunized Rhesus Macaques," *Vaccine*, 15(8):924-926 (Jun. 1997).

Gallimore, A., et al., "Early Suppression of SIV Replication By CD8+ nef-specific Cytotoxic T Cells In Vaccinated Macaques," *Nature Med.* 1(11):1167-1173 (Nov. 1995).

Gilbert, S.C., et al., "A Protein Particle Vaccine Containing Multiple Malaria Epitopes," *Nat. Biotechnol.*, 15(12):1280-1284 (1997).

Greenspan, N.S., et al., "Defining Epitopes: It's Not As Easy As It Seems," *Nature Biotechnology* 7:936-937 (1999).

Hanke, T., et al., "Immunogenicities of Intravenous and Intramuscular Administrations of Modified Vaccinia Virus Ankara-Based Multi-CTL Epitope Vaccine for Human Immunodeficiency Virus Type 1 in Mice," *J. Gen. Virol.* 79:83-90 (1998).

Hanke, T., et al., "Enhancement of MHC Class I-Restricted Peptide-Specific T Cell Induction by a DNA Prime/MVA Boost Vaccination Regime," *Vaccine* 16(5):439-445 (1998).

Hanke, T., et al., "DNA Multi-CTL Epitope Vaccines for HIV and *Plasmodium falciparum*: Immunogenicity in Mice," *Vaccine* 16(4):426-435 (1998).

Hill, AV, "DNA-Based Vaccines for Malaria: a Heterologous Prime-Boost Immunisation Strategy," *Dev. Biol.* (Basel), 104:171-179 (2000).

Hill, A.V.S., et al., "Common West African HLA Antigens Are Associated With Protection From Severe Malaria," *Nature* 352(6336):595-600 (Aug. 15, 1991).

Hirsch, V,M., et al., "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara," *J. Virol.* 70(6):3741-3752 (Jun. 1996).

Hodge, J.W., et al., "Diversified Prime and Boost Protocols Using Recombinant Vaccinia Virus and Recombinant Non-Replicating Avian Pox Virus to Enhance T-Cell Immunity and Antitumor Responses," *Vaccine* 15(6/7):759-768 (Apr./May 1997).

Huygen, K., et al., "Immunogenicity and Protective Efficacy of a Tuberculosis DNA Vaccine," *Nat. Med.* 2: 893-898 (1996).

Irvine, K.R., et al., "Route of Immunization and the Therapeutic Impact of Recombinant Anticaner Vaccines," *J. Natl. Cancer Inst.* 89(5):390-392 (Mar. 1997).

Irvine, K.R., et al., "Enhancing Efficacy of Recombinant Anticancer Vaccines With Prime/Boost Regiments That Use Two Different Vectors," *J. Natl. Cancer Inst.* 89(21):1595-1601 (Nov. 1997).

Lalvani, A., et al., "An HLA-Based Approach to the Design of a CTL-Inducing Vaccine Against *Plasmodium falciparum*," *Research in Immunology* 145(6):461-468 (1994).

Lanar, D.E., et al., "Attenuated Vaccinia Virus-Circumsporozoite Protein Recombinants Confer Protection against Rodent Malaria," *Infec. Immun.* 64(5):1666-1671 (May 1996).

Layton, F.T., et al., "Induction of Single and Dual Cytotoxic T-Lymphocyte Responses to Viral Proteins in Mice Using Recombinant Hybrid Ty-Virus-Like Particles," *Immunology* 87(2):171-178 (Feb. 1996).

Leong, K.H., et al., "Selective Induction of Immune Responses by Cytokines Coexpressed in Recombinant Fowlpox Virus," *J. Virol.*, 68(12):8125-8130 (Dec. 1994).

Leong, K.H., et al., "Generation of Enhanced Immune Responses by Consecutive Immunization with DNA and Recombinant Fowl Pox Vectors." In *Vaccines 95*, Cold Spring Harbor Laboratory Press, p. 327-331 (1995).

Li, Shengqiang, et al., "Priming With Recombinant Influenza Virus Followed By Administration of Recombinant Vaccinia Virus Induces CD8+ T-Cell-Mediated Protective Immunity against Malaria," *Proc. Natl. Acad. Sci. USA* 90(11):5214-5218 (Jun. 1993).

Limbach, K.J. and Paoletti, E., "Non-Replicating Expression Vectors: Application in Vaccine Development and Gene Therapy," *Epidemiol. Infect.* 116:241-256 (1996).

Mahnel, et al., "Experiences with Immunization Against Orthopox Viruses of Humans and Animals Using Vaccine Strain MVA," *Berliner Und Munchener Tierarztliche Wochenschrift* 107(8):253-256 (1994) Abstract Only.

McMichael, A., et al., "Malaria and Other Tropical Diseases," *Immunol. Letters* 56(1/3):28, 425, 291 (Jun. 22-25, 1997)(Abstract Nos. O.4.05.7, P.4.05.08, P.4.01.18 and P.4.01.22).

McShane, H., et al., "Enhanced Immunogenicity of CD4+ T-Cell Responses and Protective Efficacy of a DNA-Modified Vaccinia Virus Ankara Prime-Boost Vaccination Regimen for Murine Tuberculosis," *Infect. Imm.* 69(2):681-686 (2001).

Moorthy, M.S., et al., "Safety of DNA and Modified vaccina virus Ankara Vaccines Against Liver-Stage *P. falciparum* Malaria in Non-Immune Volunteers," *Vaccine*, 21(17-18):1995-2002 (2003).

Moorthy, M.S. and Hill, A., "Malaria Vaccines," *Br. Med. Bull.*, 62:59-72 (2002).

Moreno, A., et al., "Cytotoxic CD4+ T Cells From a Sporozoite-Immunized Volunteer Recognize the *Plamodium falciparum* CS Protein," *Int-Immunol*, 3(10):997-1003 (1991).

Moss, B., et al., "Host Range Restricted, Non-Replicating Vaccinia Virus Vectors as Vaccine Candidates," *Advances in Experimental Medicine and Biology* 397:7-13 (1996).

Müller, H.M., et al., "Thrombospondin Related Anonymous Protein (TRAP) of *Plasmodium falciparum* Binds Specifically to Sulfated Glycoconjugates and to HepG2 Hepatoma Cells Suggesting a Role for this Molecule in Sporozoite Invasion of Hepatocytes," *Embo J.*:2881-2889 (Jul. 1993).

Murata, K., et al., "Characterization of in Vivo Primary and Secondary CD8+ T Cell Responses Induced by Recombinant Influenza and Vaccinia Viruses," *Cell. Immunol.* 173(1):96-107 (Oct. 10, 1996).

Nardin, E.H. and Nussenzweig, R.S., "T Cell Responses to Pre-Erythrocytic Stages of Malaria: Role in Protection and Vaccine Development Against Pre-Erythrocytic Stages," *Annu. Rev. Immunol.* 11:687-727 (1993).

Plebanski, M., et al., "Protection From *Plasmodium berghei* Infection By Priming and Boosting T Cells to a Single Class I-Restricted Epitope with Recombinant Carriers Suitable for Human Use," *Eur. J. Immunol.*, 28(12):4345-4355 (1998).

Richmond, J.F.L., et al., "Screening of HIV-1 Env Glycoproteins for the Ability to Raise Neutralizing Antibody Using DNA Immunization and Recombinant Vaccinia Virus Boosting," *Virology* 230:265-274 (1997).

Rodrigues, E.G., et al., "Single Immunizing Dose of Recombinant Adenovirus Efficiently Induces CD8+ T Cell-Mediated Protective Immunity Against Malaria," *J. Immunol.* 158(3):1268-1274 (Feb. 1997).

Rodrigues, M., et al., "Influenza and Vaccinia Viruses Expressing Malaria CD8+ T and B Cell Epitopes," *J. Immunol.* 153(10):4636-4648 (Nov. 15, 1994).

Schneider, J., et al., "A Prime-Boost Immunisation Regimen Using DNA Followed By Recombinant Modified Vaccinia Virus Ankara Induces Strong Cellular Immune Responses Against the *Plasmodium falciparum* TRAP Antigen In Chimpanzees," *Vaccine*, 19(32):4595-4602 (2001).

Schneider, J., et al., "Induction of CD8+ T Cells Using Heterologous Prime-Boost Immunisation Strategies," *Immunological Reviews*, 170:29-38 (1999).

Schneider, J., et al., "Enhanced Immunogenicity for CD8+ T Cell Induction and Complete Protective Efficacy of Malaria DNA Vaccination by Boosting with Modified Vaccinia Virus Ankara," *Nature Medicine* 4(4): 397-402 (Apr. 1998).

Schödel, F., et al., "Immunity to Malaria Elicited by Hybrid Hepatitis B Virus Core Particles Carrying Circumsporozoite Protein Epitopes," *J. Exp. Med.* 180(3):1037-1046 (Sep. 1994).

Sedegah, M., et al., "Protection against Malaria by Immunization with Plasmid DNA Encoding Circumsporozoite Protein," *Proc. Natl. Acad. Sci. USA* 91(21):9866-9870 (Oct. 1994).

Seguin, M.C., et al., "Induction of Nitric Oxide Synthase Protects against Malaria in Mice Exposed to Irradiated *Plasmodium berghei* Infected Mosquitoes: Involvement of Interferon γ and CD8+ T Cells," *J. Exp. Med.* 180(1):353-358 (Jul. 1994).

Stoute, J.A., et al., "A Preliminary Evaluation of a Recombinant Circumsporozoite Protein Vaccine Against *Plasmodium falciparum* Malaria," *NE J. of Medicine* 336:86-91 (1997).

Sutter, G., et al., "A Recombinant Vector Derived From the Host Range-Restricted and Highly Attenuated MVA Strain of Vaccinia Virus Stimulates Protective Immunity in Mice to Influenza Virus," *Vaccine* 12(11):1032-1040 (Aug. 1994).

Tartaglia, J., et al., "NYVAC: A Highly Attenuated Strain of Vaccinia Virus," *Virology* 188(1):217-232 (May 1992).

Tascon, et al., "Vaccination Against Tuberculosis by DNA Injection," *Nat. Med.* 2: 888-892 (1996).

Tsang, K.Y., et al., "Generation of Human Cytotoxic T Cells Specific for Human Carcinoembryonic Antigen Epitopes From Patients Immunized With Recombinant Vaccinia-CEA Vaccine," *J. Natl. Cancer Inst.* 87(13):982-990 (Jul. 1995).

Tsuji, M., et al., "CD4+ Cytolytic T Cell Clone Confers Protection Against Murine Malaria," *J. Exp Med.*, 172(5):1353-1357 (1990).

Wang, R., et al., "Induction of CD4+ T Cell-Dependent CD8+ Type 1 Responses in Humans By a Malaria DNA Vaccine," *PNAS*, 98:10817-10822 (2001).

Wizel, B., et al., "Irradiated Sporozoite Vaccine Induces HLA-B8-Restricted Cytotoxic T Lymphocyte Responses against Two Overlapping Epitopes of the *Plasmodium falciparum* Sporozoite Surface Protein 2," *J. Exp. Med.* 182(5):1435-1445 (Nov. 1995).

Zhu, X., et al., "Functions and Specificity of T Cells Following Nucleic Acid Vaccination of Mice Against *Mycobacterium tuberculosis* Infection," *J. Immunol.*, 158:5921-5926 (1997).

Sequence Alignment of SEQ ID No. 2 with Geneseq database ID No. AAR43244 from WO 93/201103-A. Entry date: May 1994 Inventor: Elvin, et al.

Sequence Alignment of SEQ ID No. 4 with Geneseq database ID No. AAR43245 from WO 93/201103-A. Entry date: May 1994 Inventor: Elvin, et al.

Sequence Alignment of SEQ ID No. 6 with Geneseq database ID No. AAR43243 from WO 93/201103-A. Entry date: May 1994 Inventor: Elvin, et al.

Rodriguez, D., et al., "Regulated Expression of Nuclear Genes by T3 RNA Polymerase and *lac* Repressor Using Recombinant Vaccinia Virus Vectors," *J. Virol.* 64(10):4851-4857 (Oct. 1990).

Watson, J.C., et al., "General Immunization Practices," Ch. 5, in *Vaccines*, Plotkin, S.A. and Orenstein, eds., WB Saunders publ. 1999.

Drexler, I., et al., "Highly Attenuated Modified Vaccinia Virus Ankara Replicates in Baby Hamster Kidney Cells, a Potential Host for Virus Propagation, But Not in Various Human Transformed and Primary Cells," *J. Gen. Virol.* 79:347-352 (1998).

Reece, WHH, et al., "A DNA/MVA Prime-Boost Vaccination Regime Induces Strong Immune Responses and Partial Protection Agains *Plasmodium falciparum* in Humans," *Poster at the British Society for Immunology* (Dec. 2001).

Peptide Database, Cancer Immunity, Mar. 2001, online, retrieved from the Internet on Jun. 23, 2003. <URL:http://cancerimmunity.org/peptidedatabase/tcellepitopes.htm>.

Zorn, E., et al., 'A Natural Cytotoxic T Cell Response in a Spontaneously Regressing Human Melanoma Targets a Neoantigen Resulting Froma Somatic Point Mutation,' *Eur. J. Immunol.*, 29:592-601 (1999).

Rimoldi, D., et al., 'Efficient Simultaneous Presentation of NY-ESO-1/LAGE-1 Primary and Nonprimary Open Reading Frame-Derived CTL Epitopes in Melanoma,' *J. Immunol.*, 165:7253-7261 (2000).

Castelli, C., et al. 'Mass Spectrometric Identification of a Naturally Processed Melanoma Peptide Recognized by CD8+ Cytotoxic T Lymphocytes', *J. Exp. Med.*, 181:363-368 (1995).

Ohminami, H., et al., 'HLA Class I-Restricted Lysis of Leukemia Cells by a CD8+ Cytotoxic T-Lymphocyte Clone Specific for WTI Peptide,' *Blood*, 95:286-293 (2000).

'Epitope Maps', HIV Molecular Immunology database, online, retrieved from the Internet on Jun. 23, 2003. <URL: http://hiv-web.lanl.gov/content/immunology/maps/maps.html>.

SYFPEITHI Database, 'FInd Your Motif, Ligand or Epitope,.' <URL:http://syfpeithi.bmiheidelberg.com/Scripts/MHCServer.dll/findyourmotif.htm>.

Egan, M.A., et al., "Induction of Human Immunodeficiency . . . ," *Concise Communications*, 171:1623-1627, 1995.

Wang, M., et al., "Active Immunotherapy of Cancer . . . ," *The American Association of Immunologists*, p. 4685-4692, 1995.

Tartaglia, J., et al., "Protection of Cats against Feline . . . ," *Journal of Virology*, p. 2370-2375, 1993.

Brossart, P., et al., "Virus-Mediated Delivery of Antigenic . . . ," *The American Association of Immunologists*, p. 3270-3276, 1997.

Chamberlain, R.S,, Poster Presentation presented at the Meeting of the American Association of Cancer Research, Apr. 20 through Apr. 24, 1996.

Irvine, K., et al., "Comparison of a CEA-Recombinant Vaccinia . . . ," *Vaccine Research*, 2(2):79-94, 1993.

Franchini, G., et al., "Highly Attenuated HIV Type 2 . . . ," *AIDS Research and Human Retroviruses*, 11(8):909-920, 1995.

The Schlom Declaration cited in the opposition proceedings of European Patent Application No. EP0979284, to which the subject application claims priority.

The Gritz Declaration cited in the opposition proceedings of European Patent Application No. EP0979284, to which the subject application claims priority.

The Chamberlain Declaration cited in the opposition proceedings of European Patent Application No. EP0979284, to which the subject application claims priority.

Thompson, S.A., et al., "Recombinant Polyepitope Vaccines for the Delivery of Multiple CD8 Cytotoxic T Cell Epitopes," *J. Immunol.*, 157(2):822-826 (1996).

Afonso, C.L., et al., "The Genome of Fowlpox Virus," *J. Virol.* 74(8):3815-3831 (2000).

Anderson, et al., "Enhanced CD8 T Cell Response and Protective Efficacy Against Malaria Using Recombinant Fowlpox Virus In Heterologous Prime/Boost Immunisation Regimes," Abstract, *Immunology 101*(Supplement 1):32 (2000).

Berkner, K.L., "Development of Adenovirus Vectors for the Expression of Heterologous Genes," *BioTechniques* 6(7): 616-629 (1988).

Boulanger, D., et al., "Morphogenesis and Release of Fowlpox Virus," *J. Gen. Virol.* 81:675-687 (2000).

Boulanger, D., et al., "The 131-Amino-Acid Repeat Region of the Essential 39-Kilodalton Core Protein of Fowlpox Virus FP9, Equivilant to Vaccinia Virus A4L Protein, Is Nonessential and Highly Immunogenic," *J. Virol* 72(1):170-179 (1998).

Boursnell, M.E.G., et al., "A Fowlpox Virus Vaccine Vector with Insertion Sites in the Terminal Repeats: Demonstration of its Efficacy Using the Fusion Gene of Newcastle Disease Virus," *Vet. Microbiol.* 23:305-316 (1990).

Boursnell, M.E.G., et al., "Insertion of the Fusion Gene from Newcastle Disease Virus into a Non-essential Region in the Terminal Repeats of Fowlpox Virus and Demonstration of Protective Immunity Induced by the Recombinant," *J. Gen. Virology* 71:621-628 (1990).

Boyle, D.B. and Heine, H.G., "Recombinant Fowlpox Virus Vaccines for Poultry," *Immunol. Cell Biol.* 71:391-397 (1993).

Boyle, D.B., et al., "Comparison of Field and Vaccine Strains of Australian Fowlpox Viruses," *Arch. Virol.* 142:737-748 (1997).

Brooks, J.V., et al., "Boosting Vaccine for Tuberculosis," *Infect. Immun.* 69(4): 2714-2717 (2001).

Buge, S.L., et al., "Factors Associated with Slow Disease Progression in Macaques Immunized with an Adenovirus-Simian Immunodeficiency Virus (SIV) Envelope Priming-gp120 Boosting Regimen and Challenged Vaginally with SIVmac251," *J. Virol.* 73(9):7430-7440 (1999).

Campbell, J.I.A., et al., "Tandem Repeated Sequences Within the Terminal Region of the Fowlpox Virus Genome," *J. Gen. Virol.* 70:145-154 (1989).

Carter, B.J., et al., "Gene Therapy as Drug Development," *Mol. Therapy 1*:(3)211-212 (2000).

Carvalho, L.J.M., et al., "Malaria Vaccine: Candidate Antigens, Mechanisms, Constraints and Prospects," *Scand. J. Immunol.* 56:327-343 (2002).

Coupar, B.E.H., et al., "Restriction Endonuclease Mapping of the Fowlpox Virus Genome," *Virology* 179:159-167 (1990).

Dale, C. J., et al., "Induction of HIV-1-Specific T-Helper Responses and Type 1 Cytokine Secretion Following Therapeutic Vaccination of Macaques with a Recombinant Fowlpoxvirus Co-expressing Interferon-Gamma," *J. Med. Primatol.* 29:240-247 (2000).

Davis, H.L., et al., "DNA-Mediated Immunization to Hepatitis B Surface Antigen: Longevity of Primary Response and Effect of Boost," *Vaccine* 14(9):910-915 (1996).

Denis, O., et al., "Vaccination with Plasmid DNA Encoding Mycobacterial Antigen 85A Stimulates a CD4+ and CD8+ T-Cell Epitopic Repertoire Broader than that Stimulated by *Mycobacterium tuberculosis* H37Rv Infection," *Infect. Immun.* 66(4):1527-1533 (1998).

E-mail dated Jan. 5, 2006 from American Society for Microbiology re: Date of Disclosure of Buge's Document.

Grosenbach, D. W., et al., "Synergy of Vaccine Strategies to Amplify Antigen-specific Immune Responses and Antitumor Effects," *Cancer Res* 61:4497-4505 (2001).

Hertig, C., et al., "Field and Vaccine Strains of Fowlpox Virus Carry Integrated Sequences from the Avian Retrovirus, Reticuloendotheliosis Virus," *Virology* 35:367-376 (1997).

Holder, A., et al., "Falciparum Malaria MSP1 Workshop: Progress toward MSP1 Vaccine Development and Testing," *Malaria Vaccine Initiative at PATH*: 1-30 (2000).

Johnson, R.P., et al., "Induction of a Major Histocompatibility Complex Class I-Restricted Cytotoxic T-Lymphocyte Response to a Highly Conserved Region of Human Immunodeficiency Virus Type 1 (HIV-1) gp120 in Seronegative Humans Immunized with a Candidate HIV-1 Vaccine," *J. Virol.* 68(5):3145-3153 (1994).

Kazanji, M., et al. "Expression and Immunogenicity in Rats of Recombinant Adenovirus 5 DNA Plasmids and Vaccinia Virus Containing the HTLV-I *inv* Gene," *Int. J. Cancer* 71:300-307 (1997).

Kent, S.J., et al., "A Recombinant Avipoxvirus HIV-1 Vaccine Expressing Interferon-gamma is Safe and Immunogenic in Macaques," *Vaccine* 18:2250-2256 (1999).

Kent, S.J., et al., "Enhanced T-Cell Immunogenicity and Protective Efficacy of a Human Immunodeficiency Virus Type 1 Vaccine Regimen Consisting of Consecutive Priming with DNA and Boosting with Recombinant Fowlpox Virus," *J. Virol.* 72(12):10180-10188 (1998).

Kent, S.J., et al., "Analysis of Cytotoxic T Lymphocyte Responses to SIV Proteins in SIV-Infected Macaques Using Antigen-Specific Stimulation with Recombinant Vaccinia and Fowl Poxviruses," *AIDS Res. Hum. Retroviruses* 10(5):551-560 (1994).

Laidlaw, S.M. and Skinner, M.A., "Comparison of the Genome Sequence of FP9, an Attenuated, Tissue Culture-adapted European Strain of *Fowlpox virus*, with Those of Virulent American and European Viruses," *J. Gen. Virol.* 85:305-322 (2004).

Laidlaw, S.M., et al., "Fowlpox Virus Encodes Nonessential Homologs of Cellular Alpha-SNAP, PC-1, and an Orphan Human Homolog of a Secreted Nematode Protein," *J. Virol.* 72(8):6742-6751 (1998).

Mayr, A. and Malicki, K., "Attenuierung von virulentem Hühnerpockenvirus in Zellkulturen und Eigenschaften des attenuierten Virus," *Zbl. Vet. Med. B* B13, 1-13 (1966). (English Abstract attached.).

Meyer, H., et al., "Mapping of Deletions in the Genome of the Highly Attenuated Vaccinia Virus MVA and their Influence on Virulence," *J. Gen. Virol.* 72:1031-1038 (1991).

Moss, B., "Genetically Engineered Poxviruses for Recombinant Gene Expression, Vaccination, and Safety," *Proc. Natl. Acad. Sci. USA* 93:11341-11348 (1996).

Natuk, R.J., et al., "Immunogenicity of Recombinant Human Adenovirus-Human Immunodeficiency Virus Vaccines in Chimpanzees," *Aids Res. Hum. Retroviruses* (9):395-404 (1993).

NCBI Accession No. AF198100, "Fowlpox virus, complete genome," [online], Mar. 2000. [retrieved on Sep. 14, 2000] Retrieved from the Internet <URL:http://www.ncbi.nlm.nih.gov/entrez/viewer.fcgi?db=nucleotide&val=7271507>.

Notice of Opposition to a European Patent. Patent No. EP 1 214 416. Opponent: Transgene S.A. (English translation attached).

Notice of Opposition to a European Patent. Patent No. EP 1 214 416 B1. Opponent: Merck & Co., Inc.

Notice of Opposition to a European Patent. Patent No. EP 1 214 416 B1. Opponent: Crucell Holland B.V.

Paoletti, E., "Applications of Pox Virus Vectors to Vaccination: An Update," *Proc. Natl. Acad. Sci. USA* 93:11349-11353 (1996).

Pialoux, G., et al., "A Prime-Boost Approach to HIV Preventive Vaccine Using a Recombinant Canarypox Virus Expressing Glycoprotein 160 (MN) Followed by a Recombinant Glycoprotein 160 (MN/LAI)," *AIDS Res. Hum. Retroviruses.* 11(3):373-381 (1995).

Pollitt, E., et al., "Nucleotide Sequence of the 4.3 kbp BamHI-N Fragment of Fowlpox Virus FP9," *Virus Genes* 17(1):5-9 (1998).

Qingzhong, Y., et al., "Protection Against Turkey Rhinotracheitis Pneumovirus (TRTV) Induced by a Fowlpox Virus Recombinant Expressing the TRTV Fusion Glycoprotein (F)," *Vaccine* 12(6):569-573 (1994).

Robert-Guroff, M., et al., "Vaccine Protection Against a Heterologous, Non-Syncytium-Inducing, Primary Human Immunodeficiency Virus," *J. Virol.* 72(12):10275-10280 (1998).

Robinson, H.L., et al., "Neutralizing Antibody-independent Containment of Immunodeficiency Virus Challenges by DNA Priming and Recombinant Pox Virus Booster Immunizations," *Nature Med.* 5(5):526-534 (1999).

Rodrigues, E.G., et al., "Efficient Induction of Protective Anti-Malaria Immunity By Recombinant Adenovirus," *Vaccine* 16(19):1812-1817, (1998).

Rothel, J.S., et al., "Sequential Nucleic Acid and Recombinant Adenovirus Vaccination Induces Host-protective Immune Responses Against *Taenia ovis* infection in Sheep," *Parasite Immunology* 19:221-227 (1997).

Shah, K.V. and Howley, P.M., "Papillomaviruses." In *Fields Virology*, B.N. Fields, et al., eds. (PA: Lippincott-Raven Publishers) pp. 2077-2109 (1996).

Shaw, I. and Davison, T.F., "Protection From IBDV-Induced Bursal Damage By A Recombinant Fowlpox Vaccine, fpIBD1, Is Dependent on the Titre of Challenge Virus and Chicken Genotype," *Vaccine* 18:3230-3241 (2000).

Skinner, M.A., et al., "Fowlpox Virus as a Recombinant Vaccine Vector for use in Mammals and Poultry," *Expert Rev. Vaccines* 4(1):63-76 (2005).

Smith, C.L., et al., "Recombinant Modified Vaccinia Ankara Primes Functionally Activated CTL Specific for a Melanoma Tumor Antigen Epitope in Melanoma Patients with a High Risk of Disease Recurrence," *Int. J. Cancer* 113:259-266 (2005).

Somogyi, P., et al., "Fowlpox Virus Host Range Restriction: Gene Expression, DNA Replication, and Morphogenesis in Nonpermissive Mammalian Cells," *Virology* 197:439-444 (1993).

Sutter, G. and Moss, B., "Nonreplicating Vaccinia Vector Efficiently Expresses Recombinant Genes," *Proc. Natl. Acad. Sci. USA*, 89:10847-10851 (1992).

Tanghe, A., et al., "Improved Immunogenicity and Protective Efficacy of a Tuberculosis DNA Vaccine Encoding Ag85 by Protein Boosting," *Infect. Immun.* 69(5):3041-3047 (2001).

Taylor, J. and Paoletti, E., "Fowlpox Virus As A Vector in Non-Avian Species," *Vaccine* 6:466-468 (1988).

Taylor, J., et al., "Protective Immunity Against Avian Influenza Induced by a Fowlpox Virus Recombinant," *Vaccine* 6:504-508 (1988).

Taylor, J., et al., "Recombinant Fowlpox Virus Inducing Protective Immunity in Non-Avian Species," *Vaccine* 6(6):497-503 (1988).

Timofeev, A.V., et al., "Immunological Basis for Protection in a Murine Model of Tick-Borne Encephalitis by a Recombinant Adenovirus Carrying the Gene Encoding the NS1 Non-Structural Protein," *J. Gen. Virol.* 79:689-695 (1998).

Timofeyev, A.V., et al., "Recombinant Adenovirus Expressing the NS1 Nonstructural Protein of Tick-Borne Encephalitis Virus: Characteristics of Immunological Basis of Antiviral Effect," *Vopr. Virusol.* 42:219-222 (1997). (English Abstract attached.).

Tsukamoto, K., et al., "Dual-Viral Vector Approach Induced Strong and Long-Lasting Protective Immunity against Very Virulent Infectious Bursal Disease Virus," *Virology* 269(2):257-267 (2000).

Walker, B.D., et al., "Long-term Culture and Fine Specificity of Human Cytotoxic T-Lymphocyte Clones Reactive with Human Immunodeficiency Virus Type 1," *Proc. Natl. Acad. Sci. USA* 86:9514-9518 (1989).

Warnier, G., et al., "Induction of a Cytolytic T-cell Response in Mice with a Recombinant Adenovirus Coding for Tumor Antigen P815A" *Int. J. Cancer* 67(2):303-310 (1996). (Abstract only).

Xiang, Z.Q., et al., "Induction of Genital Immunity by DNA Priming and Intranasal Booster Immunization with a Replication-Defective Adenoviral Recombinant," *J. Immunol.* 162: 6716-6723 (1999).

Altman, J.D., and Feinberg, M.B., "HIV Escape: There and Back Again," *Nature Med.* 10(3): 229-230 (2004).

Desrosiers, R.C., "Prospects for an AIDS Vaccine," *Nature Med.* 10(3):221-223 (2004).

Fang, Z.-Y., et al., "Expression of Vaccina E3L and K3L Genes by a Novel Recombinant Canarypox HIV Vaccine Vector Enhances HIV-1 Pseudovirion Production and Inhibits Apoptosis in Human Cells," *Virology* 291:272-284 (2001).

Friedrich, T.C., et al., "Reversion of CTL Escape—Variant Immunodeficiency Viruses in vivo," *Nature Med.* 10(3):275-281 (2004).

Fuller, D.H., et al., "Enhancement of Immunodeficiency Virus-Specific Immune Responses in DNA-immunized Rhesus Macaques," *Vaccine* 15(8):924-926 (1997).

Ho, M. AIDS Vaccines Trials Dangerous. Isis News No. 11/12, Institute of Science in Society [online], Oct. 2001 [retrieved on Nov. 27, 2006]. Retrieved from the Internet <URL:www.i-sis.org.uk/isisnews/i-sisnews11-19.php>.

Hu, S.-L., "Non-Human Primate Models for AIDS Vaccine Research," *Curr. Drug Targets Infect. Disord.*, 5(2):193-201 (2005).

Koziel, M.J., "The Role of Immune Responses in the Pathogenesis of Hepatitis C Virus Infection," *J. Viral Hepatitus* 4(2):31-41 (1997). Abstract only provided.

Koziel, M.J. and Walker, B.D., "Characteristics of the Intrahepatic Cytotoxic T Lymphocyte Response in Chronic Hepatitis C Virus Infection," *Spriner Seminars in Immunopathology*, 19(1):69-83 (1997). Abstract only provided.

Leslie, A.J., et al., "HIV Evolution: CTL Escape Mutation and Reversion After Transmission," *Nature Med.* 10(3):282-289 (2004).

Letvin, N.L., "Progress Toward an HIV Vaccine," *Annu. Rev. Med.* 56:213-223 (2005).

Niewiesk, S., et al., "Measles Virus-Induced Immune Suppression in the Cotton Rat (*Sigmodon hispidus*) Model Depends on Viral Glycoproteins," *J. Virol.* 71(10):7214-7219 (1997).

Picard, O., et al., "Complication of Intramuscular/Subcutaneous Immune Therapy in Severely Immune-Compromised Individuals," *J. Acquir. Immune Defic. Syndr.*, 4(6):641-643 (1991).

Puig, M., et al., "CD4+ Immune Escape and Subsequent T-Cell Failure Following Chimpanzee Immunization Against Hepatitis C Virus," *Hepatology*, 44:736-745 (2006).

Puls, R.L. and Emery, S., "Therapeutic Vaccination against HIV: Current Progress and Future Possibilities," *Clin. Sci.*, 110(1):59-71 (2006).

Tonini, T., et al., "Current Approaches to Developing a Preventative HIV Vaccine," *Curr. Opin. Investig. Drugs*, 6(2):155-162 (2005).

Wiley, J.A., et al., "Production of Interferon-γ by Influenza Hemagglutinin-Specific CD8 Effector T Cells Influences the Development of Pulmonary Immunopathology," *Am. J. Pathol.* 158(1): 119-130 (2001).

Dose-Ranging Study to Evaluate the Safety & Immunogenicity of a HIV Vaccine 732461 in Healthy HIV Seronegative Volunteers [online], Feb. 2007 [retrieved on Mar. 7, 2007], Retrieved from the Internet <URL:http://www.clinicaltrials.gov>.

Matano, T., et al., "Administration of an Anti-CD8 Monoclonal Antibody Interferes with the Clearance of Chimeric Simian/Human Immunodeficiency Virus during Primary Infections of Rhesus Macaques," *J. Virology* 72(1): 164-169 (1998).

Riddell, S.R. and Greenberg, P.D., "Principles for Adoptive T Cell Therapy of Human Viral Diseases," *Annu. Rev. Immunol.* 13: 545-586 (1995).

Riddell, S.R., et al. "Restoration of Viral Immunity in Immunodeficient Humans by the Adoptive Transfer of T Cell Clones," *Science* 257 (1992).

Rowland-Jones, S., et al., "HIV-specific Cytotoxic T-cells in HIV-exposed but Uninfected Gambian Women," *Nature Medicine* 1(1): 59-64 (1995).

Safety of and Immune Response to a DNA HIV Vaccine (pGA2/JS7) Boosted With a Modified Vaccinia HIV Vaccine (MVA/HIV62) in Healthy Adults. National Institute of Allergy and Infectious Diseases [online], Sep. 2006 [retrieved on Mar. 7, 2007], Retrieved from the Internet <URL:http://www.clinicaltrials.gov>.

Safety of and Immune Response to a DNA HIV Vaccine Followed by an Adenoviral Vector HIV Vaccine in Healthy Adults. National Institute of Allergy and Infectious Diseases [online], Jan. 2007 [retrieved on Mar. 1, 2007], Retrieved from the Internet <URL:http://www.clinicaltrials.gov>.

Brander, C. and Walker, B.D., The HLA Class I Restricted CTL Response in HIV-1 Infection: Systematic Identification of Optimal Epitopes. HIV Molecular Immunology Database [online], Feb. 2002 [retrieved on Oct. 19, 2006], Retrieved from the Internet <URL:http://www.hiv-web.lanl.gov>.

SYFPEITHI Database, "Find Your Motif," [online], [retrieved on Sep. 1, 2006]. Retrieved from the Internet <URL:http://www.syfpeithi.de/Scripts/MHCServer.dll/FindYourMotif.htm>.

The Schlom Declaration cited in the Notice of Opposition to a European Patent. Patent No. EP0979284 [Date signed by Declarant: Sep. 24, 2003; Date signed by Opponent: Oct. 2, 2003; Date filed in EPO: Oct. 2, 2003].

The Gritz Declaration cited in the Notice of Opposition to a European Patent. Patent No. EP0979284 [Date signed by Opponent: Oct. 2, 2003; Date filed in EPO: Oct. 2, 2003].

The Chamberlain Declaration cited in the Notice of Opposition to a European Patent. Patent No. EP0979284 [Date signed by Opponent: Oct. 2, 2003; Date filed in EPO: Oct. 2, 2003].

Notice of Opposition to a European Patent. Patent No. EP 1 214 416. Opponent: Transgene S.A. (English translation attached.) [Date signed by Opponent: Feb. 3, 2006 ; Date filed in EPO: Feb. 6, 2006].

Notice of Opposition to a European Patent. Patent No. EP 1 214 416 B1. Opponent: Merck & Co., Inc. [Date signed by Opponent: Feb. 9, 2006 ; Date filed in EPO: Feb. 13, 2006].

Notice of Opposition to a European Patent. Patent No. EP 1 214 416 B1. Opponent: Crucell Holland B.V. [Date signed by Opponent: Feb. 6, 2006 ; Date filed in EPO: Feb. 13, 2006].

Borrow, P., et al., "Virus-Specific CD8+ Cytotoxic T-Lymphocyte Activity Associated with Control of Viremia in Primary Human Immunodeficiency Virus Type 1 Infection," *J. Virol.* 68(9): 6103-6110 (1994).

Chow, Y-H., et al., "Improvement of Hepatitis B Virus DNA Vaccines by Plasmids Coexpressing Hepatitis B Surface Antigen and Interleukin-2," *J. Virol.*, 71(1): 169-178 (1997).

Hutchings, C.L., et al., "Novel Protein and Poxvirus-Based Vaccine Combinations for Simultaneous Induction of Humoral and Cell-Mediated Immunity," *J. Immunol.*, 175: 599-606 (2005).

Kmieciak, D., et al., "Enhancement of Cellular and Humoral Immune Responses to Human Immunodeficiency Virus Type 1 Gag and Pol by a G/P-92 Fusion Protein Expressing Highly Immunogenic Gag p17/p24 and Pol p51 Antigens," *J. Hum. Virol.* 4(6):306-316(2001).

Lindsey, K.R., et al., "Evaluation of Prime/Boost Regimens Using Recombinant Poxvirus/Tyrosinase Vaccines for the Treatment of Patients with Metastatic Melanoma," *Clin. Cancer Res.*, 12(8): 2526-2537 (2006).

Marshall, J.L., et al., "Phase I Study in Advanced Cancer Patients of a Diversified Prime-and-Boost Vaccination Protocol using Recombinant Vaccinia Virus and Recombinant Nonreplicating Avipox Virus to Elicit Anti-Carcinoembryonic Antigen Immune Responses," *J. Clin. Oncol.*, 18(23): 3964-3973 (2000).

Rosenberg, S.A., et al., "Recombinant Fowlpox Viruses Encoding the Anchor-Modified gp100 Melanoma Antigen can Generate Antitumor Immune Responses in Patients with Metastatic Melanoma," *Clin. Cancer Res.*, 9(8): 2973-2980 (2003).

Tagawa, S.T., et al., "Phase I Study of Intranodal Delivery of a Plasmid DNA Vaccine for Patients with Stage IV Melanoma," *Cancer*, 98(1): 144-154 (2003).

Tomiyama, H., et al., "Different Effects of Nef-Mediated HLA Class I Down-Regulation on Human Immunodeficiency Virus Type 1-Specific $CD8^{30}$ T-Cell Cytolytic Activity and Cytokine Production," *J. Virol.*, 76(15): 7535-7543 (2002).

van Baren, N., et al., "Tumoral and Immunologic Response After Vaccination of Melanoma Patients with an ALVAC Virus Encoding MAGE Antigens Recognized by T Cells," *J. Clin. Oncol.*, 23(35): 9008-9021 (2005).

Vuola, J.M., et al., "Differential Immunogenicity of Various Heterologuous Prime-Boost Vaccine Regimens Using DNA and Viral Vectors in Healthy Volunteers," *J. Immunol.*, 174(1): 449-455 (2005).

Wang, X., et al., "Cellular Immune Responses to Helper-Free HSV-1 Amplicon Particles Encoding HIV-1 gp120 are Enhanced by DNA Priming," *Vaccine*, 21(19-20): 2288-2297 (2003).

Woodberry, T., et al., "Prime Boost Vaccination Strategies: CD8 T Cell Numbers, Protection, and Th1 Bias," *J. Immunol.*, 170: 2599-2604 (2003).

Zajac, P., et al., "Phase I/II Clinical Trial of a Nonreplicative Vaccinia Virus Expressing Multiple HLA-A0201-Restricted Tumor-Associated Epitopes and Costimulatory Molecules in Metastatic Melanoma Patients," *Human Gene Therapy*, 14(16): 1497-1510 (2003).

Anderson, R., "Treatment of Melanoma by Heterologous PrimeBoost Immunotherapy," Oxxon Therapeutics, TVLN Presentation given on Apr. 6, 2006 (17 pages).

Haigwood, N.L., "Predictive Value of Primate Models for AIDS," *AIDS Reviews* 6:187-198 (2004).

* cited by examiner

```
                         SEQUENCE LISTING

<160> NUMBER OF SEQ ID NOS: 78

<210> SEQ ID NO 1
<211> LENGTH: 24
<212> TYPE: DNA
<213> ORGANISM: Unknown
<220> FEATURE:
<223> OTHER INFORMATION: CTL Epitope of the Malaria String

<400> SEQUENCE: 1
aagccgaacg acaagtcctt gtat                                          24

<210> SEQ ID NO 2
<211> LENGTH: 8
<212> TYPE: PRT
<213> ORGANISM: Unknown
<220> FEATURE:
<223> OTHER INFORMATION: CTL Epitope of the Malaria String

<400> SEQUENCE: 2

Lys Pro Asn Asp Lys Ser Leu Tyr
 1               5

<210> SEQ ID NO 3
<211> LENGTH: 24
<212> TYPE: DNA
<213> ORGANISM: Unknown
<220> FEATURE:
<223> OTHER INFORMATION: CTL Epitope of the Malaria String

<400> SEQUENCE: 3
aaacctaagg acgaattgga ctac                                          24

<210> SEQ ID NO 4
<211> LENGTH: 8
<212> TYPE: PRT
<213> ORGANISM: Unknown
<220> FEATURE:
<223> OTHER INFORMATION: CTL Epitope of the Malaria String

<400> SEQUENCE: 4

Lys Pro Lys Asp Glu Leu Asp Tyr
 1               5

<210> SEQ ID NO 5
<211> LENGTH: 27
<212> TYPE: DNA
<213> ORGANISM: Unknown
<220> FEATURE:
<223> OTHER INFORMATION: CTL Epitope of the Malaria String

<400> SEQUENCE: 5
aagccaatcg ttcaatacga caacttc                                       27

<210> SEQ ID NO 6
<211> LENGTH: 9
```

-continued

<212> TYPE: PRT
<213> ORGANISM: Unknown
<220> FEATURE:
<223> OTHER INFORMATION: CTL Epitope of the Malaria String

<400> SEQUENCE: 6

Lys Pro Ile Val Gln Tyr Asp Asn Phe
1 5

<210> SEQ ID NO 7
<211> LENGTH: 33
<212> TYPE: DNA
<213> ORGANISM: Unknown
<220> FEATURE:
<223> OTHER INFORMATION: CTL Epitope of the Malaria String

<400> SEQUENCE: 7
gcctccaaga acaaggaaaa ggctttgatc atc 33

<210> SEQ ID NO 8
<211> LENGTH: 11
<212> TYPE: PRT
<213> ORGANISM: Unknown
<220> FEATURE:
<223> OTHER INFORMATION: CTL Epitope of the Malaria String

<400> SEQUENCE: 8

Ala Ser Lys Asn Lys Glu Lys Ala Leu Ile Ile
1 5 10

<210> SEQ ID NO 9
<211> LENGTH: 27
<212> TYPE: DNA
<213> ORGANISM: Unknown
<220> FEATURE:
<223> OTHER INFORMATION: CTL Epitope of the Malaria String

<400> SEQUENCE: 9
ggtatcgctg gtggtttggc cttgttg 27

<210> SEQ ID NO 10
<211> LENGTH: 9
<212> TYPE: PRT
<213> ORGANISM: Unknown
<220> FEATURE:
<223> OTHER INFORMATION: CTL Epitope of the Malaria String

<400> SEQUENCE: 10

Gly Ile Ala Gly Gly Leu Ala Leu Leu
1 5

<210> SEQ ID NO 11
<211> LENGTH: 30
<212> TYPE: DNA
<213> ORGANISM: Unknown
<220> FEATURE:
<223> OTHER INFORMATION: CTL Epitope of the Malaria String

<400> SEQUENCE: 11
atgaacccta atgacccaaa cagaaacgtc 30

<210> SEQ ID NO 12
<211> LENGTH: 10
<212> TYPE: PRT
<213> ORGANISM: Unknown
<220> FEATURE:
<223> OTHER INFORMATION: CTL Epitope of the Malaria String

```
<400> SEQUENCE: 12

Met Asn Pro Asn Asp Pro Asn Arg Asn Val
1               5                   10

<210> SEQ ID NO 13
<211> LENGTH: 27
<212> TYPE: DNA
<213> ORGANISM: Unknown
<220> FEATURE:
<223> OTHER INFORMATION: CTL Epitope of the Malaria String

<400> SEQUENCE: 13
atgatcaacg cctacttgga caagttg                                        27

<210> SEQ ID NO 14
<211> LENGTH: 9
<212> TYPE: PRT
<213> ORGANISM: Unknown
<220> FEATURE:
<223> OTHER INFORMATION: CTL Epitope of the Malaria String

<400> SEQUENCE: 14

Met Ile Asn Ala Tyr Leu Asp Lys Leu
1               5

<210> SEQ ID NO 15
<211> LENGTH: 24
<212> TYPE: DNA
<213> ORGANISM: Unknown
<220> FEATURE:
<223> OTHER INFORMATION: CTL Epitope of the Malaria String

<400> SEQUENCE: 15
atctccaagt acgaagacga aatc                                           24

<210> SEQ ID NO 16
<211> LENGTH: 8
<212> TYPE: PRT
<213> ORGANISM: Unknown
<220> FEATURE:
<223> OTHER INFORMATION: CTL Epitope of the Malaria String

<400> SEQUENCE: 16

Ile Ser Lys Tyr Glu Asp Glu Ile
1               5

<210> SEQ ID NO 17
<211> LENGTH: 27
<212> TYPE: DNA
<213> ORGANISM: Unknown
<220> FEATURE:
<223> OTHER INFORMATION: CTL Epitope of the Malaria String

<400> SEQUENCE: 17
tcctacatcc catctgccga aaagatc                                        27

<210> SEQ ID NO 18
<211> LENGTH: 9
<212> TYPE: PRT
<213> ORGANISM: Unknown
<220> FEATURE:
<223> OTHER INFORMATION: CTL Epitope of the Malaria String

<400> SEQUENCE: 18

Ser Tyr Ile Pro Ser Ala Glu Lys Ile
```

-continued

```
<210> SEQ ID NO 19
<211> LENGTH: 27
<212> TYPE: DNA
<213> ORGANISM: Unknown
<220> FEATURE:
<223> OTHER INFORMATION: CTL Epitope of the Malaria String

<400> SEQUENCE: 19
cacttgggta acgttaagta cttggtt                                         27

<210> SEQ ID NO 20
<211> LENGTH: 9
<212> TYPE: PRT
<213> ORGANISM: Unknown
<220> FEATURE:
<223> OTHER INFORMATION: CTL Epitope of the Malaria String

<400> SEQUENCE: 20

His Leu Gly Asn Val Lys Tyr Leu Val
 1               5

<210> SEQ ID NO 21
<211> LENGTH: 24
<212> TYPE: DNA
<213> ORGANISM: Unknown
<220> FEATURE:
<223> OTHER INFORMATION: CTL Epitope of the Malaria String

<400> SEQUENCE: 21
aagtctttgt acgatgaaca catc                                            24

<210> SEQ ID NO 22
<211> LENGTH: 8
<212> TYPE: PRT
<213> ORGANISM: Unknown
<220> FEATURE:
<223> OTHER INFORMATION: CTL Epitope of the Malaria String

<400> SEQUENCE: 22

Lys Ser Leu Tyr Asp Glu His Ile
 1               5

<210> SEQ ID NO 23
<211> LENGTH: 27
<212> TYPE: DNA
<213> ORGANISM: Unknown
<220> FEATURE:
<223> OTHER INFORMATION: CTL Epitope of the Malaria String

<400> SEQUENCE: 23
ttattgatgg actgttctgg ttctatt                                         27

<210> SEQ ID NO 24
<211> LENGTH: 9
<212> TYPE: PRT
<213> ORGANISM: Unknown
<220> FEATURE:
<223> OTHER INFORMATION: CTL Epitope of the Malaria String

<400> SEQUENCE: 24

Leu Leu Met Asp Cys Ser Gly Ser Ile
 1               5

<210> SEQ ID NO 25
```

-continued

<211> LENGTH: 48
<212> TYPE: DNA
<213> ORGANISM: Unknown
<220> FEATURE:
<223> OTHER INFORMATION: CTL Epitope of the Malaria String

<400> SEQUENCE: 25
aacgctaatc caaacgcaaa tccgaacgcc aatcctaacg cgaatccc 48

<210> SEQ ID NO 26
<211> LENGTH: 16
<212> TYPE: PRT
<213> ORGANISM: Unknown
<220> FEATURE:
<223> OTHER INFORMATION: CTL Epitope of the Malaria String

<400> SEQUENCE: 26

Asn Ala Asn Pro Asn Ala Asn Pro Asn Ala Asn Pro Asn Ala Asn Pro
1 5 10 15

<210> SEQ ID NO 27
<211> LENGTH: 60
<212> TYPE: DNA
<213> ORGANISM: Unknown
<220> FEATURE:
<223> OTHER INFORMATION: CTL Epitope of the Malaria String

<400> SEQUENCE: 27
gacgaatggt ctccatgttc tgtcacttgt ggtaagggta ctcgctctag aaagagagaa 60

<210> SEQ ID NO 28
<211> LENGTH: 20
<212> TYPE: PRT
<213> ORGANISM: Unknown
<220> FEATURE:
<223> OTHER INFORMATION: CTL Epitope of the Malaria String

<400> SEQUENCE: 28

Asp Glu Trp Ser Pro Cys Ser Val Thr Cys Gly Lys Gly Thr Arg Ser
1 5 10 15

Arg Lys Arg Glu
20

<210> SEQ ID NO 29
<211> LENGTH: 27
<212> TYPE: DNA
<213> ORGANISM: Unknown
<220> FEATURE:
<223> OTHER INFORMATION: CTL Epitope of the Malaria String

<400> SEQUENCE: 29
tacttgaaca aaattcaaaa ctctttg 27

<210> SEQ ID NO 30
<211> LENGTH: 9
<212> TYPE: PRT
<213> ORGANISM: Unknown
<220> FEATURE:
<223> OTHER INFORMATION: CTL Epitope of the Malaria String

<400> SEQUENCE: 30

Tyr Leu Asn Lys Ile Gln Asn Ser Leu
1 5

<210> SEQ ID NO 31
<211> LENGTH: 27

```
<212> TYPE: DNA
<213> ORGANISM: Unknown
<220> FEATURE:
<223> OTHER INFORMATION: CTL Epitope of the Malaria String

<400> SEQUENCE: 31
atggaaaagt tgaaagaatt ggaaaag                                        27

<210> SEQ ID NO 32
<211> LENGTH: 9
<212> TYPE: PRT
<213> ORGANISM: Unknown
<220> FEATURE:
<223> OTHER INFORMATION: CTL Epitope of the Malaria String

<400> SEQUENCE: 32

Met Glu Lys Leu Lys Glu Leu Glu Lys
 1               5

<210> SEQ ID NO 33
<211> LENGTH: 24
<212> TYPE: DNA
<213> ORGANISM: Unknown
<220> FEATURE:
<223> OTHER INFORMATION: CTL Epitope of the Malaria String

<400> SEQUENCE: 33
gctacttctg tcttggctgg tttg                                           24

<210> SEQ ID NO 34
<211> LENGTH: 8
<212> TYPE: PRT
<213> ORGANISM: Unknown
<220> FEATURE:
<223> OTHER INFORMATION: CTL Epitope of the Malaria String

<400> SEQUENCE: 34

Ala Thr Ser Val Leu Ala Gly Leu
 1               5

<210> SEQ ID NO 35
<211> LENGTH: 48
<212> TYPE: DNA
<213> ORGANISM: Unknown
<220> FEATURE:
<223> OTHER INFORMATION: CTL Epitope of the Malaria String

<400> SEQUENCE: 35
gacccaaacg ctaacccaaa cgttgaccca aacgccaacc caaacgtc                 48

<210> SEQ ID NO 36
<211> LENGTH: 16
<212> TYPE: PRT
<213> ORGANISM: Unknown
<220> FEATURE:
<223> OTHER INFORMATION: CTL Epitope of the Malaria String

<400> SEQUENCE: 36

Asp Pro Asn Ala Asn Pro Asn Val Asp Pro Asn Ala Asn Pro Asn Val
 1               5                   10                  15

<210> SEQ ID NO 37
<211> LENGTH: 42
<212> TYPE: DNA
<213> ORGANISM: Unknown
<220> FEATURE:
<223> OTHER INFORMATION: CTL Epitope of the Malaria String
```

-continued

<400> SEQUENCE: 37
caagttcact tccaaccatt gcctccggcc gttgtcaagt tg                42

<210> SEQ ID NO 38
<211> LENGTH: 14
<212> TYPE: PRT
<213> ORGANISM: Unknown
<220> FEATURE:
<223> OTHER INFORMATION: CTL Epitope of the Malaria String

<400> SEQUENCE: 38

Gln Val His Phe Gln Pro Leu Pro Pro Ala Val Val Lys Leu
 1               5                  10

<210> SEQ ID NO 39
<211> LENGTH: 42
<212> TYPE: DNA
<213> ORGANISM: Unknown
<220> FEATURE:
<223> OTHER INFORMATION: CTL Epitope of the Malaria String

<400> SEQUENCE: 39
caattcatca aggccaactc taagttcatc ggtatcaccg aa                42

<210> SEQ ID NO 40
<211> LENGTH: 14
<212> TYPE: PRT
<213> ORGANISM: Unknown
<220> FEATURE:
<223> OTHER INFORMATION: CTL Epitope of the Malaria String

<400> SEQUENCE: 40

Gln Phe Ile Lys Ala Asn Ser Lys Phe Ile Gly Ile Thr Glu
 1               5                  10

<210> SEQ ID NO 41
<211> LENGTH: 229
<212> TYPE: PRT
<213> ORGANISM: Unknown
<220> FEATURE:
<223> OTHER INFORMATION: Complete Epitope of Malaria String

<400> SEQUENCE: 41

Met Ile Asn Ala Tyr Leu Asp Lys Leu Ile Ser Lys Tyr Glu Asp Glu
 1               5                  10                  15

Ile Ser Tyr Ile Pro Ser Ala Glu Lys Ile Gly Ser Lys Pro Asn Asp
             20                  25                  30

Lys Ser Leu Tyr Lys Pro Lys Asp Glu Leu Asp Tyr Lys Pro Ile Val
         35                  40                  45

Gln Tyr Asp Asn Phe Gly Ser Ala Ser Lys Asn Lys Glu Lys Ala Leu
     50                  55                  60

Ile Ile Gly Ile Ala Gly Gly Leu Ala Leu Leu Met Asn Pro Asn Asp
 65                  70                  75                  80

Pro Asn Arg Asn Val Gly Ser His Leu Gly Asn Val Lys Tyr Leu Val
                 85                  90                  95

Lys Ser Leu Tyr Asp Glu His Ile Leu Leu Met Asp Cys Ser Gly Ser
            100                 105                 110

Ile Gly Ser Asp Pro Asn Ala Asn Pro Asn Val Asp Pro Asn Ala Asn
        115                 120                 125

Pro Asn Val Gln Val His Phe Gln Pro Leu Pro Pro Ala Val Val Lys
    130                 135                 140

```
Leu Gln Phe Ile Lys Ala Asn Ser Lys Phe Ile Gly Ile Thr Glu Gly
145                 150                 155                 160

Ser Tyr Leu Asn Lys Ile Gln Asn Ser Leu Met Glu Lys Leu Lys Glu
                165                 170                 175

Leu Glu Lys Ala Thr Ser Val Leu Ala Gly Leu Gly Ser Asn Ala Asn
            180                 185                 190

Pro Asn Ala Asn Pro Asn Ala Asn Pro Asn Ala Asn Pro Asp Glu Trp
        195                 200                 205

Ser Pro Cys Ser Val Thr Cys Gly Lys Gly Thr Arg Ser Arg Lys Arg
    210                 215                 220

Glu Gly Ser Gly Lys
225

<210> SEQ ID NO 42
<211> LENGTH: 8
<212> TYPE: PRT
<213> ORGANISM: Unknown
<220> FEATURE:
<223> OTHER INFORMATION: CTL Epitope of HIV-1 gp41

<400> SEQUENCE: 42

Tyr Leu Lys Asp Gln Gln Leu Leu
1               5

<210> SEQ ID NO 43
<211> LENGTH: 9
<212> TYPE: PRT
<213> ORGANISM: Unknown
<220> FEATURE:
<223> OTHER INFORMATION: CTL Epitope of HIV-1 gp41

<400> SEQUENCE: 43

Glu Arg Tyr Leu Lys Asp Gln Gln Leu
1               5

<210> SEQ ID NO 44
<211> LENGTH: 9
<212> TYPE: PRT
<213> ORGANISM: Unknown
<220> FEATURE:
<223> OTHER INFORMATION: CTL Epitope of SIV env

<400> SEQUENCE: 44

Glu Ile Thr Pro Ile Gly Leu Ala Pro
1               5

<210> SEQ ID NO 45
<211> LENGTH: 9
<212> TYPE: PRT
<213> ORGANISM: Unknown
<220> FEATURE:
<223> OTHER INFORMATION: CTL Epitope of HIV-1 p24

<400> SEQUENCE: 45

Pro Pro Ile Pro Val Gly Glu Ile Tyr
1               5

<210> SEQ ID NO 46
<211> LENGTH: 9
<212> TYPE: PRT
<213> ORGANISM: Unknown
<220> FEATURE:
<223> OTHER INFORMATION: CTL Epitope of HIV-1 p24
```

```
<400> SEQUENCE: 46

Gly Glu Ile Tyr Lys Arg Trp Ile Ile
1               5

<210> SEQ ID NO 47
<211> LENGTH: 10
<212> TYPE: PRT
<213> ORGANISM: Unknown
<220> FEATURE:
<223> OTHER INFORMATION: CTL Epitope of HIV-1 p24

<400> SEQUENCE: 47

Lys Arg Trp Ile Ile Leu Gly Leu Asn Lys
1               5                  10

<210> SEQ ID NO 48
<211> LENGTH: 10
<212> TYPE: PRT
<213> ORGANISM: Unknown
<220> FEATURE:
<223> OTHER INFORMATION: CTL Epitope of HIV-1 p24

<400> SEQUENCE: 48

Ile Ile Leu Gly Leu Asn Lys Ile Val Arg
1               5                  10

<210> SEQ ID NO 49
<211> LENGTH: 10
<212> TYPE: PRT
<213> ORGANISM: Unknown
<220> FEATURE:
<223> OTHER INFORMATION: CTL Epitope of HIV-1 p24

<400> SEQUENCE: 49

Leu Gly Leu Asn Lys Ile Val Arg Met Tyr
1               5                  10

<210> SEQ ID NO 50
<211> LENGTH: 8
<212> TYPE: PRT
<213> ORGANISM: Unknown
<220> FEATURE:
<223> OTHER INFORMATION: CTL Epitope of SIV env

<400> SEQUENCE: 50

Tyr Asn Leu Thr Met Lys Cys Arg
1               5

<210> SEQ ID NO 51
<211> LENGTH: 10
<212> TYPE: PRT
<213> ORGANISM: Unknown
<220> FEATURE:
<223> OTHER INFORMATION: CTL Epitope of HIV-1 gp120

<400> SEQUENCE: 51

Arg Gly Pro Gly Arg Ala Phe Val Thr Ile
1               5                  10

<210> SEQ ID NO 52
<211> LENGTH: 9
<212> TYPE: PRT
<213> ORGANISM: Unknown
<220> FEATURE:
<223> OTHER INFORMATION: CTL Epitope of HIV-1 gp120

<400> SEQUENCE: 52
```

```
Gly Arg Ala Phe Val Thr Ile Gly Lys
  1               5
```

```
<210> SEQ ID NO 53
<211> LENGTH: 9
<212> TYPE: PRT
<213> ORGANISM: Unknown
<220> FEATURE:
<223> OTHER INFORMATION: CTL Epitope of HIV-1 gag

<400> SEQUENCE: 53

Thr Pro Tyr Asp Ile Asn Gln Met Leu
  1               5
```

```
<210> SEQ ID NO 54
<211> LENGTH: 9
<212> TYPE: PRT
<213> ORGANISM: Unknown
<220> FEATURE:
<223> OTHER INFORMATION: CTL Epitope of SIV gag

<400> SEQUENCE: 54

Cys Thr Pro Tyr Asp Ile Asn Gln Met
  1               5
```

```
<210> SEQ ID NO 55
<211> LENGTH: 11
<212> TYPE: PRT
<213> ORGANISM: Unknown
<220> FEATURE:
<223> OTHER INFORMATION: CTL Epitope of HIV-1 nef

<400> SEQUENCE: 55

Arg Pro Gln Val Pro Leu Arg Pro Met Thr Tyr
  1               5                   10
```

```
<210> SEQ ID NO 56
<211> LENGTH: 10
<212> TYPE: PRT
<213> ORGANISM: Unknown
<220> FEATURE:
<223> OTHER INFORMATION: CTL Epitope of HIV-1 nef

<400> SEQUENCE: 56

Gln Val Pro Leu Arg Pro Met Thr Tyr Lys
  1               5                   10
```

```
<210> SEQ ID NO 57
<211> LENGTH: 8
<212> TYPE: PRT
<213> ORGANISM: Unknown
<220> FEATURE:
<223> OTHER INFORMATION: CTL Epitope of HIV-1 nef

<400> SEQUENCE: 57

Val Pro Leu Arg Pro Met Thr Tyr
  1               5
```

```
<210> SEQ ID NO 58
<211> LENGTH: 9
<212> TYPE: PRT
<213> ORGANISM: Unknown
<220> FEATURE:
<223> OTHER INFORMATION: CTL Epitope of HIV-1 nef

<400> SEQUENCE: 58
```

```
Ala Val Asp Leu Ser His Phe Leu Lys
  1               5
```

<210> SEQ ID NO 59
<211> LENGTH: 9
<212> TYPE: PRT
<213> ORGANISM: Unknown
<220> FEATURE:
<223> OTHER INFORMATION: CTL Epitope of HIV-1 nef

<400> SEQUENCE: 59

```
Asp Leu Ser His Phe Leu Lys Glu Lys
  1               5
```

<210> SEQ ID NO 60
<211> LENGTH: 8
<212> TYPE: PRT
<213> ORGANISM: Unknown
<220> FEATURE:
<223> OTHER INFORMATION: CTL Epitope of HIV-1 nef

<400> SEQUENCE: 60

```
Phe Leu Lys Glu Lys Gly Gly Leu
  1               5
```

<210> SEQ ID NO 61
<211> LENGTH: 9
<212> TYPE: PRT
<213> ORGANISM: Unknown
<220> FEATURE:
<223> OTHER INFORMATION: CTL Epitope of HIV-1 pol

<400> SEQUENCE: 61

```
Ile Leu Lys Glu Pro Val His Gly Val
  1               5
```

<210> SEQ ID NO 62
<211> LENGTH: 10
<212> TYPE: PRT
<213> ORGANISM: Unknown
<220> FEATURE:
<223> OTHER INFORMATION: CTL Epitope of HIV-1 pol

<400> SEQUENCE: 62

```
Ile Leu Lys Glu Pro Val His Gly Val Tyr
  1               5                  10
```

<210> SEQ ID NO 63
<211> LENGTH: 9
<212> TYPE: PRT
<213> ORGANISM: Unknown
<220> FEATURE:
<223> OTHER INFORMATION: CTL Epitope of HIV-1 pol

<400> SEQUENCE: 63

```
His Pro Asp Ile Val Ile Tyr Gln Tyr
  1               5
```

<210> SEQ ID NO 64
<211> LENGTH: 9
<212> TYPE: PRT
<213> ORGANISM: Unknown
<220> FEATURE:
<223> OTHER INFORMATION: CTL Epitope of HIV-1 pol

<400> SEQUENCE: 64

```
Val Ile Tyr Gln Tyr Met Asp Asp Leu
```

<210> SEQ ID NO 65
<211> LENGTH: 45
<212> TYPE: PRT
<213> ORGANISM: Unknown
<220> FEATURE:
<223> OTHER INFORMATION: Tumor Epitope String

<400> SEQUENCE: 65

Met Leu Pro Tyr Leu Gly Trp Leu Val Phe Ala Gln His Pro Asn Ala
1               5                   10                  15

Glu Leu Leu Lys His Tyr Leu Phe Arg Asn Leu Ser Pro Ser Tyr Val
            20                  25                  30

Tyr His Gln Phe Ile Pro Asn Pro Leu Leu Gly Leu Asp
        35                  40                  45

<210> SEQ ID NO 66
<211> LENGTH: 9
<212> TYPE: PRT
<213> ORGANISM: Unknown
<220> FEATURE:
<223> OTHER INFORMATION: CTL Peptide Epitope of P1 Tumour Antigen

<400> SEQUENCE: 66

Leu Pro Tyr Leu Gly Trp Leu Val Phe
1               5

<210> SEQ ID NO 67
<211> LENGTH: 9
<212> TYPE: PRT
<213> ORGANISM: Unknown
<220> FEATURE:
<223> OTHER INFORMATION: CTL Peptide Epitope of P. berghei CSP

<400> SEQUENCE: 67

Ser Tyr Ile Pro Ser Ala Glu Lys Ile
1               5

<210> SEQ ID NO 68
<211> LENGTH: 10
<212> TYPE: PRT
<213> ORGANISM: Unknown
<220> FEATURE:
<223> OTHER INFORMATION: CTL Peptide Epitope of HIV gag

<400> SEQUENCE: 68

Arg Gly Pro Gly Arg Ala Phe Val Thr Ile
1               5                   10

<210> SEQ ID NO 69
<211> LENGTH: 9
<212> TYPE: PRT
<213> ORGANISM: Unknown
<220> FEATURE:
<223> OTHER INFORMATION: CTL Peptide Epitope of E. coli b-galactosidase

<400> SEQUENCE: 69

Thr Pro His Pro Ala Arg Ile Gly Leu
1               5

<210> SEQ ID NO 70
<211> LENGTH: 9
<212> TYPE: PRT
<213> ORGANISM: Unknown
<220> FEATURE:

-continued

<223> OTHER INFORMATION: CTL Peptide Epitope of Influenza A Virus NP

<400> SEQUENCE: 70

Thr Tyr Gln Arg Thr Arg Ala Leu Val
1 5

<210> SEQ ID NO 71
<211> LENGTH: 8
<212> TYPE: PRT
<213> ORGANISM: Unknown
<220> FEATURE:
<223> OTHER INFORMATION: CTL Peptide Epitope of Influenza A Virus NP

<400> SEQUENCE: 71

Ser Asp Tyr Glu Gly Arg Leu Ile
1 5

<210> SEQ ID NO 72
<211> LENGTH: 9
<212> TYPE: PRT
<213> ORGANISM: Unknown
<220> FEATURE:
<223> OTHER INFORMATION: CTL Peptide Epitope of Influenza A Virus NP

<400> SEQUENCE: 72

Ala Ser Asn Glu Asn Met Glu Thr Met
1 5

<210> SEQ ID NO 73
<211> LENGTH: 9
<212> TYPE: PRT
<213> ORGANISM: Unknown
<220> FEATURE:
<223> OTHER INFORMATION: CTL Peptide Epitope of P. falciparum TRAP

<400> SEQUENCE: 73

Ile Asn Val Ala Phe Asn Arg Phe Leu
1 5

<210> SEQ ID NO 74
<211> LENGTH: 33
<212> TYPE: DNA
<213> ORGANISM: Unknown
<220> FEATURE:
<223> OTHER INFORMATION: 5' Primer MamuNdeI

<400> SEQUENCE: 74
cctgactcag accatatggg ctctcactcc atg 33

<210> SEQ ID NO 75
<211> LENGTH: 85
<212> TYPE: DNA
<213> ORGANISM: Unknown
<220> FEATURE:
<223> OTHER INFORMATION: 3' Primer MamuNdeI

<400> SEQUENCE: 75
gtgataagct taacgatgat tccacaccat tttctgtgca tccagaatat gatgcaggga 60
tccctcccat ctcagggtga ggggc 85

<210> SEQ ID NO 76
<211> LENGTH: 27
<212> TYPE: DNA
<213> ORGANISM: Unknown
<220> FEATURE:
<223> OTHER INFORMATION: Primer B2MBACK

```
<400> SEQUENCE: 76
tcagaccata tgtctcgctc cgtggcc                                              27

<210> SEQ ID NO 77
<211> LENGTH: 31
<212> TYPE: DNA
<213> ORGANISM: Unknown
<220> FEATURE:
<223> OTHER INFORMATION: Primer B2MFOR

<400> SEQUENCE: 77
tcagacaagc ttttacatgt ctcgatccca c                                         31

<210> SEQ ID NO 78
<211> LENGTH: 11
<212> TYPE: PRT
<213> ORGANISM: Unknown
<220> FEATURE:
<223> OTHER INFORMATION: tr57 Target Epitope from TRAP

<400> SEQUENCE: 78

Lys Thr Ala Ser Cys Gly Val Trp Asp Glu Trp
 1               5                  10
```

METHODS AND REAGENTS FOR IMMUNIZATION WHICH GENERATE A CD8 T CELL IMMUNE RESPONSE

RELATED APPLICATIONS

This application is a continuation of U.S. application Ser. No. 10/686,943, filed Oct. 16, 2003, which is a continuation of U.S. application Ser No. 09/454,204, filed Dec. 9, 1999 (which issued as U.S. Pat. No. 6,663,871 B1), which is a continuation of International Application No. PCT/GB98/01681, which designated the United States and was filed Jun. 9, 1998, published in English, which claims priority under 35 U.S.C. § 119 or 365 to Great Britain Application No. GB9711957.2 filed Jun. 9, 1997.

This application is also a continuation of U.S. application Ser. No. 10/653,624, filed Sep. 2, 2003, which is a divisional of U.S. application Ser. No. 09/454,204, filed Dec. 9, 1999 (which issued as U.S. Pat. No. 6,663,871 B1), which is a continuation of International Application No. PCT/GB98/01681, which designated the United States and was filed Jun. 9, 1998, published in English, which claims priority under 35 U.S.C. § 119 or 365 to Great Britain Application No. GB9711957.2 filed Jun. 9, 1997.

The entire teachings of the above applications are incorporated herein by reference.

BACKGROUND OF INVENTION

A general problem in vaccinology has been an inability to generate high levels of CD8 T cells by immunization. This has impeded the development of vaccines against several diseases including malaria.

*Plasmodium falciparum* malaria causes hundreds of millions of malaria infections each year and is responsible for 1-2 million deaths annually. The development of an effective vaccine against malaria is thus a major priority for global public health. A considerable body of immunological research over the last twenty years had led to the identification both of candidate vaccine antigens from the parasite and immunological mechanisms on the host that are likely to protect against infection and disease. However, despite this progress there is still no means of vaccinating against malaria infection which has been shown to be effective in field trials.

A major problem has been the identification of a means of inducing a sufficiently strong immune response in vaccinated individuals to protect against infection and disease. So, although many malaria antigens are known that might be useful in vaccinating against malaria the problem has been how to deliver such antigens or fragments of them known as epitopes, which are recognized by cells of the immune system, in a way that induces a sufficiently strong immune response of a particular type.

It has been known for many years that it is possible to protect individuals by immunizing them with very large doses of irradiated malaria sporozoite given by bites from infected mosquitoes. Although this is a wholly impractical method of mass vaccination it has provided a model for analyzing the immune responses that might be mediating protective immunity against sporozoite infection (Nardin and Nussenzweig 1993).

A considerable amount of research over the last decade or more has indicated that a major protective immune response against the early pre-erythrocytic stage of *P. falciparum* malaria is mediated by T lymphocytes of the CD8+ ve type (CD8+ T cells). Such cells have been shown to mediate protection directly in mouse models of malaria infection (Nardin and Nussenzweig 1993). Such T cells have also been identified in individuals naturally exposed to malaria and in volunteers immunized with irradiated sporozoite (Hill et al. 1991; Aidoo et al. 1995; Wizel et al. 1995). There is much indirect evidence that such CD8+ T cells are protective against malaria infection and disease in humans (Lalvani et al. 1994).

CD8+ T cells may function in more than one way. The best known function is the killing or lysis of target cells bearing peptide antigen in the context of an MHC class I molecule. Hence these cells are often termed cytotoxic T lymphocytes (CTL). However, another function, perhaps of greater protective relevance in malaria infections is the ability of CD8+ T cells to secrete interferon gamma (IFN-γ). Thus assays of lytic activity and of IFN-γ release are both of value in measuring a CD8+ T cell immune response. In malaria these CD8+ ve cells can protect by killing the parasite at the early intrahepatic stage of malaria infection before any symptoms of disease are produced (Seguin et al. 1994).

The agent of fatal human malaria, *P. falciparum* infects a restricted number of host species: humans, chimpanzees and some species of New World monkey. The best non-human model of malaria is the chimpanzee because this species is closely related to humans and liver-stage infection is observed consistently unlike in the monkey hosts (Thomas et al. 1994). Because of the expense and limited availability of chimpanzees most laboratory studies of malaria are performed in mice, using the rodent malaria species *P. berghei* or *P. yoelii*. These latter two models are well studied and it has been shown in both that CD8+ ve lymphocytes play a key role in protective immunity against sporozoite challenge.

Previous studies have assessed a large variety of means of inducing CD8+ T cell responses against malaria. Several of these have shown some level of CD8+ T cell response and partial protection against malaria infection in the rodent models (e.g. Li et al. 1993; Sedegah et al. 1994; Lanar et al. 1996). However, an effective means of immunizing with subunit vaccines by the induction of sufficiently high levels of CD8+ T lymphocytes to protect effectively against malaria sporozoite infection has not previously been demonstrated.

In recent years improved immune responses generated to potential vaccines have been sought by varying the vectors used to deliver the antigen. There is evidence that in some instances antibody responses are improved by using two different vectors administered sequentially as prime and boost. A variety of combinations of prime and boost have been tested in different potential vaccine regimes.

Leong et al. (Vaccines 1995, 327-331) describe immunizing mice firstly to DNA expressing the influenza haemagglutinin (HA) antigen and then with a recombinant fowlpox vector expressing HA. An enhanced antibody response was obtained following boosting.

Richmond et al. (Virology 1997, 230: 265-274) describe attempts to raise neutralizing antibodies against HIV-1 env using DNA priming and recombinant vaccinia virus boosting. Only low levels of antibody responses were observed with this prime boost regime and the results were considered disappointing.

Fuller et al. (Vaccine 1997, 15:924-926 and Immunol Cell Biol 1997, 75:389-396) describe an enhancement of antibody responses to DNA immunization of macaques by using a booster immunization with replicating recombinant vaccinia viruses. However, this did not translate into enhanced protective efficacy as a greater reduction in viral burden and attenuation of CD4 T cell loss was seen in the DNA primed and boosted animals.

Hodge et al. (Vaccine 1997, 15: 759-768) describe the induction of lymphoproliferative T cell responses in a mouse model for cancer using human carcinoembryonic antigen (CEA) expressed in a recombinant fowl pox virus (ALVAC). The authors primed an immune response with CEA-recombinant replication competent vaccinia viruses of the Wyeth or WR strain and boosted the response with CEA-recombinant ALVAC. This led to an increase in T cell proliferation but did not result in enhanced protective efficacy if compared to three wild type recombinant immunizations (100% protection), three recombinant ALVAC-CEA immunizations (70% protection) or WR prime followed by two ALVAC-CEA immunizations (63% protection).

Thus some studies of heterologous prime-boost combination have found some enhancement of antibody and lymphoproliferative responses but no significant effect on protective efficacy in an animal model. CD8 T cells were not measured in these studies. The limited enhancement of antibody response probably simply reflects the fact that antibodies to the priming immunogen will often reduce the immunogenicity of a second immunization with the same immunogen, while boosting with a different carrier will in part overcome this problem. This mechanism would not be expected to be significantly affected by the order of immunization.

Evidence that a heterologous prime boost immunization regime might affect CD8 T cell responses was provided by Li et al. (1993). They described partial protective efficacy induced in mice against malaria sporozoite challenge by administering two live viral vectors, a recombinant replicating influenza virus followed by a recombinant replicating vaccinia virus encoding a malaria epitope. Reversing the order of immunization led to loss of all protective efficacy and the authors suggested that this might be related to infection of liver cells by vaccinia, resulting in localization of CTLs in the liver to protect against the hepatocytic stages of malaria parasites.

Rodrigues et al. (J. Immunol. 1994, 4636-4648) describe immunizing mice with repeated doses of a recombinant influenza virus expressing an immunodominant B cell epitope of the malarial circumsporozoite (CS) protein followed by a recombinant vaccinia virus booster. The use of a wild type vaccinia strain and an attenuated but replication-competent vaccinia strain in the booster yielded very similar levels of partial protection. However the attenuated but replication competent strain was slightly less immunogenic for priming CD8 T cells than the wild type vaccinia strain.

Murata et al. (Cell. Immunol. 1996, 173: 96-107) reported enhanced CD8 T cell responses after priming with replicating recombinant influenza viruses and boosting with a replicating strain of vaccinia virus and suggested that the partial protection observed in the two earlier studies was attributable to this enhanced CD8 T cell induction.

Thus these three studies together provide evidence that a booster immunization with a replicating recombinant vaccinia virus may enhance to some degree CD8 T cell induction following priming with a replicating recombinant influenza virus. However, there are two limitations to these findings in terms of their potential usefulness. Firstly, the immunogenicity induced was only sufficient to achieve partial protection against malaria and even this was dependent on a highly immunogenic priming immunization with an unusual replicating recombinant influenza virus. Secondly, because of the potential and documented side-effects of using these replicating viruses as immunogens these recombinant vectors are not suitable for general human use as vaccines.

Modified vaccinia virus Ankara (MVA) is a strain of vaccinia virus which does not replicate in most cell types, including normal human tissues. MVA was derived by serial passage >500 times in chick embryo fibroblasts (CEF) of material derived from a pox lesion on a horse in Ankara, Turkey (Mayr et al. 1975). It was shown to be replication-impaired yet able to induce protective immunity against veterinary poxvirus infections (Mayr 1976). MVA was used as a human vaccine in the final stages of the smallpox eradication campaign, being administered by intracutaneous, subcutaneous and intramuscular routes to >120,000 subjects in southern Germany. No significant side effects were recorded, despite the deliberate targeting of vaccination to high risk groups such as those with eczema (Mayr et al. 1978; Stickl et al. 1974; Mahnel et al. 1994;). The safety of MVA reflects the avirulence of the virus in animal models, including irradiated mice and following intracranial administration to neonatal mice. The non-replication of MVA has been correlated with the production of proliferative white plaques on chick chorioallantoic membrane, abortive infection of non-avian cells, and the presence of six genomic deletions totaling approximately 30 kb (Meyer et al. 1991). The avirulence of MVA has been ascribed partially to deletions affecting host range genes K1L and C7L, although limited viral replication still occurs on human TK-143 cells and African Green Monkey CV-1 cells (Altenburger et al. 1989). Restoration of the K1L gene only partially restores MVA host range (Sutter et al. 1994). The host range restriction appears to occur during viral particle maturation, with only immature virions being observed in human HeLa cells on electron microscopy (Sutter et al. 1992). The late block in viral replication does not prevent efficient expression of recombinant genes in MVA. Recombinant MVA expressing influenza nucleoprotein, influenza haemagglutinin, and SIV proteins have proved to be immunogenic and provide varying degrees of protection in animal models, although this has never been ascribed to CD8+ T lymphocytes alone (Sutter et al. 1994, Hirsch et al. 1995; Hirsch et al. 1996). Recombinant MVA is considered a promising human vaccine candidate because of these properties of safety and immunogenicity (Moss et al. 1995). Recombinant MVA containing DNA which codes for foreign antigens is described in U.S. Pat. No. 5,185,146 (Altenburger).

Poxviruses have evolved strategies for evasion of the host immune response that include the production of secreted proteins that function as soluble receptors for tumor necrosis factor, IL-1β, interferon (IFN)-α/β and IFN-γ, which normally have sequence similarity to the extracellular domain of cellular cytokine receptors (Symons et al. 1995; Alcami et al. 1995; Alcami et al. 1992). The most recently described receptor of this nature is a chemokine receptor (Graham et al. 1997). These viral receptors generally inhibit or subvert an appropriate host immune response, and their presence is associated with increased pathogenicity. The Il-1β receptor is an exception: its presence diminishes the host febrile response and enhances host survival in the face of infection (Alcami et al. 1996). We have discovered that MVA lacks functional cytokine receptors for interferon γ, interferon αβ, Tumor Necrosis Factor and CC chemokines, but it does possess the potentially beneficial IL-1β receptor. MVA is the only known strain of vaccinia to possess this cytokine receptor profile, which theoretically renders it safer and more immunogenic than other poxviruses. Another replication-impaired and safe strain of vaccinia known as NYVAC is fully described in Tartaglia et al.(Virology 1992, 188: 217-232).

It has long been recognized that live viruses have some attractive features as recombinant vaccine vectors including a high capacity for foreign antigens and fairly good immunogenicity for cellular immune responses (Ellis 1988 new technologies for making vaccines. In: Vaccines. Editors: Plotkin S A and Mortimer E A. W B Saunders, Philadelphia, page 568; Woodrow G C 1977. In: New Generation Vaccines $2^{nd}$ Edition. Editors: Levine M M, Woodrow G C, Kaper J B, Cobon G, page 33). This has led to attempts to attenuate the virulence of such live vectors in various ways including reducing their replication capacity (Tartaglia J et al. 1992 Virology 188: 217-232). However such a reduction in replication reduces the amount of antigen produced by the virus and thereby would be expected to reduce vaccine inumunogenicity. Indeed attenuation of replicating vaccinia strains has previously been shown to lead to some substantial reductions in antibody responses (Lee M S et al, 1992 J Virology 66: 2617-2630). Similarly the non-replicating fowlpox vector was found to be less immunogenic for antibody production and less protective than a replicating wild-type vaccinia strain in a rabies study (Taylor J et al. 1991 Vaccine 9: 190-193).

SUMMARY OF INVENTION

It has now been discovered that non-replicating and replication-impaired strains of poxvirus provide vectors which give an extremely good boosting effect to a primed CTL response. Remarkably, this effect is significantly stronger than a boosting effect by wild type poxviruses. The effect is observed with malarial and other antigens such as viral and tumor antigens, and is protective as shown in mice and non-human primate challenge experiments. Complete rather than partial protection from sporozoite challenge has been observed with the novel immunization regime.

BRIEF DESCRIPTION OF THE DRAWINGS

FIG. 8A, C57BL/6, *P. falciparum* TRAP;. FIG. 8B, DBA/2, *E .coli* b-galactosidase; FIG. 8C, BALB/c, HM epitope string CTL activity against malaria peptide (pb9); FIG. 8D, DBA/2, HM epitope string CTL activity against pb9; FIG. 8E, BALB/c; HM epitope string CTL activity against HIV peptide; FIG. 8F, DBA/2, HM epitope string CTL activity against HIV peptide; FIG. 8G, BALB/c, tumour epitope string CTL activity against P1A-derived peptide; and in FIG. 8H, DBA/2, tumour epitope string CTL activity against P1A-derived peptide. Each curve shows the data for an individual mouse.

FIGS. 9A-9E show sporozoite-primed CTL responses are substantially boosted by MVA. Mice were immunised with: FIG. 9A, two low doses (50+50) of irradiated sporozoites; FIG. 9B, two high doses (300+500) of sporozoites; FIG. 9D, low-dose sporozoite priming followed by boosting with MVA.PbCSP; FIG. 9E, high dose sporozoite priming followed by boosting with MVA.PbCSP. CTL responses following immunisation with MVA.PbCSP are shown in FIG. 9C.

FIG. 11A, MVA; FIG. 11B, NYVAC; and WR inFigure C. The frequencies of peptide-specific CD8+ T cells were determined using the ELISPOT assay.

DETAILED DESCRIPTION OF THE INVENTION

Figure 1:
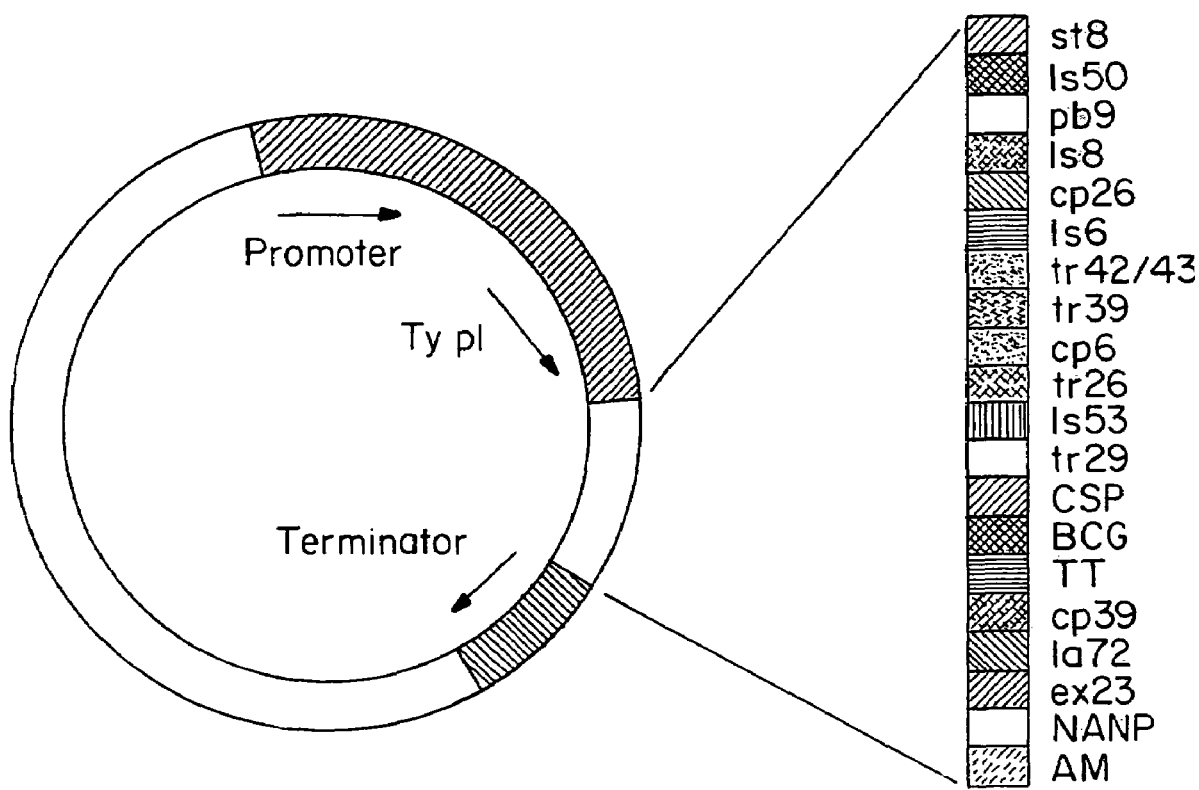
FIG. 1 shows the construct used to express Ty-VLP with the malaria epitope cassette CABDHFE. CTL epitopes are from *P. falciparum* STARP (sporozoite threonine- and asparagine-rich protein) (st), LSA-1 (liver stage antigen 1) (ls), CSP (circumsporozoite protein) (cp), TRAP (thrombospondin-related adhesive protein) (tr), LSA-3 (liver stage antigen 3) (la) and Exp-1 (exported protein 1) (ex). Helper epitopes are from the *P. falciparum* CS protein, the *M. tuberculosis* 38 Kd antigen and Tetanus Toxoid. NANP is the antibody epitope from CS and AM is the adhesion motif from *P. falciparum* TRAP (Muller et al 1993). The length of the complete string is 229 amino acids.

It is an aim of this invention to identify an effective means of immunizing against malaria. It is a further aim of this invention to identify means of immunizing against other diseases in which CD8+ T cell responses play a protective role. Such diseases include but are not limited to infection and disease caused by the viruses HIV, herpes simplex, herpes zoster, hepatitis C, hepatitis B, influenza, Epstein-Barr virus, measles, dengue and HTLV-1; by the bacteria *Mycobacterium tuberculosis* and *Listeria* sp.; and by the protozoan parasites Toxoplasma and Trypanosoma; and certain forms of cancer e.g. melanoma, cancer of the breast and cancer of the colon.

We describe here a novel method of immunizing that generated very high levels of CD8+ T cells and was found to be capable of inducing unprecedented complete protection against *P. berghei* sporozoite challenge. The same approach was tested in higher primates and found to be highly immunogenic in this species also, and was found to induce partial protection against *P. falciparum* challenge. Induction of protective immune responses has also been demonstrated in two additional mouse models of viral infection and cancer.

We show further than the novel immunization regime that is described here is also effective in generating strong CD8+ T cell responses against HIV epitopes. Considerable evidence indicates that the generation of such CD8+ T cell responses can be expected to be of value in prophylactic or therapeutic immunization against this viral infection and disease (Gallimore et al 1995; Ada 1996). We demonstrate that strong CD8+ T cell responses may be generated against epitopes from both HIV and malaria using an epitope string with sequences from both of these micro-organisms. The success in generating enhanced immunogenicity against both HIV and malaria epitopes, and also against influenza and tumor epitopes, indicates that this novel immunization regime can be effective generally against many infectious pathogens and also in non-infectious diseases where the generation of a strong CD8+ T cell response may be of value.

A surprising feature of the current invention is the finding of the very high efficacy of non-replicating agents in both priming and particularly in boosting a CD8+ T cell response. In general the immunogenicity of CD8+ T cell induction by live replicating viral vectors has previously been found to be higher than for non-replicating agents or replication-impaired vectors. This is as would be expected from the greater amount of antigen produced by agents that can replicate in the host. Here however we find that the greatest immunogenicity and protective efficacy is surprisingly observed with non-replicating vectors. The latter have an added advantage for vaccination in that they are in general safer for use in humans than replicating vectors.

The present invention provides in one aspect a kit for generating a protective CD8+ T cell immune response against at least one target antigen, which kit comprises:
  (i) a priming composition comprising a source of one or more CD8+ T cell epitopes of the target antigen, together with a pharmaceutically acceptable carrier; and
  (ii) a boosting composition comprising a source of one or more CD8+ T cell epitopes of the target antigen, including at least one CD8+ T cell epitope which is the same as a CD8+ T cell epitope of the priming composition, wherein the source of CD8+ T cell epitopes is a non-replicating or replication-impaired recombinant poxvirus vector, together with a pharmaceutically acceptable carrier; with the proviso that if the source of epitopes in (i) is a viral vector, the viral vector in (ii) is derived from a different virus.

In another aspect the invention provides a method for generating a protective CD8+ T cell immune response against at least one target antigen, which method comprises administering at least one dose of component (i), followed by at least one dose of component (ii) of the kit according to the invention.

Preferably, the source of CD8+ T cell epitopes in (i) in the method according to the invention is a non-viral vector or a non-replicating or replication-impaired viral vector, although replicating viral vectors may be used.

Preferably, the source of CD8+ T cell epitopes in (i) is not a poxvirus vector, so that there is minimal cross-reactivity between the primer and the booster.

In one preferred embodiment of the invention, the source of CD8+ T cell epitopes in the priming composition is a nucleic acid, which may be DNA or RNA, in particular a recombinant DNA plasmid. The DNA or RNA may be packaged, for example in a lysosome, or it may be in free form.

In another preferred embodiment of the invention, the source of CD8+ T cell epitopes in the priming composition is a peptide, polypeptide, protein, polyprotein or particle comprising two or more CD8+ T cell epitopes, present in a recombinant string of CD8+ T cell epitopes or in a target antigen. Polyproteins include two or more proteins which may be the same, or preferably different, linked together. Particularly preferred in this embodiment is a recombinant proteinaceous particle such as a Ty virus-like particle (VLP) (Burns et al. Molec. Biotechnol. 1994, 1: 137-145).

Preferably, the source of CD8+ T cell epitopes in the boosting composition is a vaccinia virus vector such as MVA or NYVAC. Most preferred is the vaccinia strain modified virus ankara (MVA) or a strain derived therefrom. Alternatives to vaccinia vectors include avipox vectors such as fowlpox or canarypox vectors. Particularly suitable as an avipox vector is a strain of canarypox known as ALVAC (commercially available as Kanapox), and strains derived therefrom.

Poxvirus genomes can carry a large amount of heterologous genetic information. Other requirements for viral vectors for use in vaccines include good immunogenicity and safety. MVA is a replication-impaired vaccinia strain with a good safety record. In most cell types and normal human tissues, MVA does not replicate; limited replication of MVA is observed in a few transformed cell types such as BHK21 cells. It has now been shown, by the results described herein, that recombinant MVA and other non-replicating or replication-impaired strains are surprisingly and significantly better than conventional recombinant vaccinia vectors at generating a protective CD8+ T cell response, when administered in a boosting composition following priming with a DNA plasmid, a recombinant Ty-VLP or a recombinant adenovirus.

It will be evident that vaccinia virus strains derived from MVA, or independently developed strains having the features of MVA which make MVA particularly suitable for use in a vaccine, will also be suitable for use in the invention.

MVA containing an inserted string of epitopes (MVA-HM, which is described in the Examples) has been deposited at the European Collection of Animal Cell Cultures, CAMR, Salisbury, Wiltshire SP4 0JG, UK under accession no. V97060511 on 5 Jun. 1997.

The term "non-replicating" or "replication-impaired" as used herein means not capable of replication to any significant extent in the majority of normal mammalian cells or normal human cells. Viruses which are non-replicating or replication-impaired may have become so naturally (i.e. they may be isolated as such from nature) or artificially e.g. by breeding in vitro or by genetic manipulation, for example deletion of a gene which is critical for replication. There will generally be one or a few cell types in which the viruses can be grown, such as CEF cells for MVA.

Replication of a virus is generally measured in two ways: 1) DNA synthesis and 2) viral titre. More precisely, the term "non-replicating or replication-impaired" as used herein and as it applies to poxviruses means viruses which satisfy either or both of the following criteria:
 1) exhibit a 1 log (10 fold) reduction in DNA synthesis compared to the Copenhagen strain of vaccinia virus in MRC-5 cells (a human cell line);
 2) exhibit a 2 log reduction in viral titre in HELA cells (a human cell line) compared to the Copenhagen strain of vaccinia virus.

Examples of poxviruses which fall within this definition are MVA, NYVAC and avipox viruses, while a virus which falls outside the definition is the attenuated vaccinia strain M7.

Alternative preferred viral vectors for use in the priming composition according to the invention include a variety of different viruses, genetically disabled so as to be non-replicating or replication-impaired. Such viruses include for example non-replicating adenoviruses such as E1 deletion mutants. Genetic disabling of viruses to produce non-replicating or replication-impaired vectors has been widely described in the literature (e.g. McLean et al. 1994).

Other suitable viral vectors for use in the priming composition are vectors based on herpes virus and Venezuelan equine encephalitis virus (VEE) (Davies et al. 1996). Suitable bacterial vectors for priming include recombinant BCG and recombinant Salmonella and Salmonella transformed with plasmid DNA (Daiji A et al. 1997 Cell 91: 765-775).

Alternative suitable non-viral vectors for use in the priming composition include lipid-tailed peptides known as lipopeptides, peptides fused to carrier proteins such as KLH either as fusion proteins or by chemical linkage, whole antigens with adjuvant, and other similar systems. Adjuvants such as QS21 or SBAS2 (Stoute J A et al. 1997 N Engl J Medicine 226: 86-91) may be used with proteins, peptides or nucleic acids to enhance the induction of T cell responses. These systems are sometimes referred to as "immunogens" rather than "vectors", but they are vectors herein in the sense that they carry the relevant CD8+ T cell epitopes.

There is no reason why the priming and boosting compositions should not be identical in that they may both contain the priming source of CD8+ T cell epitopes as defined in (i) above and the boosting source of CD8+ T cell epitopes as defined in (ii) above. A single formulation which can be used as a primer and as a booster will simplify administration. The important thing is that the primer contains at least the priming source of epitopes as defined in (i) above and the booster contains at least the boosting source of epitopes as defined in (ii) above.

The CD8+ T cell epitopes either present in, or encoded by the priming and boosting compositions, may be provided in a variety of different forms, such as a recombinant string of one or two or more epitopes, or in the context of the native target antigen, or a combination of both of these. CD8+ T cell epitopes have been identified and can be found in the literature, for many different diseases. It is possible to design epitope strings to generate a CD8+ T cell response against any chosen antigen that contains such epitopes. Advantageously, the epitopes in a string of multiple epitopes are linked together without intervening sequences so that unnecessary nucleic acid and/or amino acid material is avoided. In addition to the CD8+ T cell epitopes, it may be preferable to include one or more epitopes recognized by T helper cells, to augment the immune response generated by the epitope string. Particularly suitable T helper cell epitopes are ones which are active in individuals of different HLA types, for example T helper epitopes from tetanus (against which most individuals will already be primed). A useful combination of three T helper epitopes is employed in the examples described herein. It may also be useful to include B cell epitopes for stimulating B cell responses and antibody production.

The priming and boosting compositions described may advantageously comprise an adjuvant. In particular, a priming composition comprising a DNA plasmid vector may also comprise granulocyte macrophage-colony stimulating factor (GM-CSF), or a plasmid encoding it, to act as an adjuvant; beneficial effects are seen using GM-CSF in polypeptide form.

The compositions described herein may be employed as therapeutic or prophylactic vaccines. Whether prophylactic or therapeutic immunization is the more appropriate will usually depend upon the nature of the disease. For example, it is anticipated that cancer will be immunized against therapeutically rather than before it has been diagnosed, while anti-malaria vaccines will preferably, though not necessarily be used as a prophylactic.

The compositions according to the invention may be administered via a variety of different routes. Certain routes may be favoured for certain compositions, as resulting in the generation of a more effective response, or as being less likely to induce side effects, or as being easier for administration. The present invention has been shown to be effective with gene gun delivery, either on gold beads or as a powder.

In further aspects, the invention provides:
 a method for generating a protective CD8+ T cell immune response against a pathogen or tumor, which method comprises administering at least one dose of a recombinant DNA plasmid encoding at least one CD8+ T cell epitope or antigen of the pathogen or cancer, followed by at least one dose of a non-replicating or replication-impaired recombinant pox virus encoding the same epitope or antigen;
 a method for generating a protective CD8+ T cell immune response against a pathogen or tumor, which method comprises administering at least one dose of a recombinant protein or particle comprising at least one epitope or antigen of the pathogen or cancer, followed by at least one dose of a recombinant MVA vector encoding the same epitope or antigen;

the use of a recombinant non-replicating or replication-impaired pox virus vector in the manufacture of a medicament for boosting a CD8+ T cell immune response;

the use of an MVA vector in the manufacture of a medicament for boosting a CD8+ T cell immune response;

a medicament for boosting a primed CD8+ T cell response against at least one target antigen or epitope, comprising a source of one or more CD8+ T cell epitopes of the target antigen, wherein the source of CD8+ T cell epitopes is a non-replicating or a replication-impaired recombinant poxvirus vector, together with a pharmaceutically acceptable carrier; and the priming and/or boosting compositions described herein, in particulate form suitable for delivery by a gene gun; and methods of immunization comprising delivering the compositions by means of a gene gun.

Also provided by the invention are: the epitope strings described herein, including epitope strings comprising the amino acid sequences listed in table 1 and table 2; recombinant DNA plasmids encoding the epitope strings; recombinant Ty-VLPs comprising the epitope strings; a recombinant DNA plasmid or non-replicating or replication impaired recombinant pox virus encoding the *P. falciparum* antigen TRAP; and a recombinant polypeptide comprising a whole or substantially whole protein antigen such as TRAP and a string of two or more epitopes in sequence such as CTL epitopes from malaria.

Example Formulations and Immunization Protocols

| Formulation 1 | |
|---|---|
| Priming Composition: | DNA plasmid 1 mg/ml in PBS |
| Boosting Composition: | Recombinant MVA, $10^8$ ffu in PBS |

Protocol: Administer two doses of 1 mg of priming composition, i.m., at 0 and 3 weeks followed by two doses of booster intradermally at 6 and 9 weeks.

| Formulation 2 | |
|---|---|
| Priming Composition: | Ty-VLP 500 µg in PBS |
| Boosting Composition: | MVA, $10^8$ ffu in PBS |

Protocol: Administer two doses of priming composition, i.m., at 0 and 3 weeks, then 2 doses of booster at 6 and 9 weeks. For tumor treatment, MVA is given i.v. as one of most effective routes.

| Formulation 3 | |
|---|---|
| Priming Composition: | Protein 500 µg + adjuvant (QS-21) |
| Boosting Composition: | Recombinant MVA, $10^8$ ffu in PBS |

Protocol: Administer two doses of priming composition at 0 and 3 weeks and 2 doses of booster i.d. at 6 and 9 weeks.

| Formulation 4 | |
|---|---|
| Priming Composition: | Adenovirus vector, $10^9$ pfu in PBS |
| Boosting Composition: | Recombinant MVA, $10^8$ ffu in PBS |

Protocol: Administer one or two doses of priming composition intradermally at 0 and 3 weeks and two doses of booster i.d. at 6 and 9 weeks.

The above doses and protocols may be varied to optimise protection. Doses may be given between for example, 1 to 8 weeks apart rather than 2 weeks apart.

The invention will now be further described in the examples which follow.

EXAMPLES

Example 1

Materials and Methods

Generation of the Epitope Strings

The malaria epitope string was made up of a series of cassettes each encoding three epitopes as shown in Table 1, with restriction enzyme sites at each end of the cassette. Each cassette was constructed from four synthetic oligonucleotides which were annealed together, ligated into a cloning vector and then sequenced to check that no errors had been introduced. Individual cassettes were then joined together as required. The BamHI site at the 3' end of cassette C was fused to the BglII site at the 5' end of cassette A, destroying both restriction enzyme sites and encoding a two amino acid spacer (GS) between the two cassettes. Cassettes B, D and H were then joined to the string in the same manner. A longer string containing CABDHFE was also constructed in the same way.

TABLE 1

CTL Epitopes of the Malaria (M) String

| Cassette | Epitope | Amino acid Sequence | | DNA sequence | | Type | HLA restriction |
|---|---|---|---|---|---|---|---|
| A | Ls8 | KPNDKSLY | SEQ ID NO.: 2 | AAGCCGAACGACAAGTCCTTGTAT | SEQ ID NO.: 1 | CTL | B35 |
| | Cp26 | KPKDELDY | SEQ ID NO.: 4 | AAACCTAAGGACGAATTGGACTAC | SEQ ID NO.: 3 | CTL | B35 |
| | Ls6 | KPIVQYDNF | SEQ ID NO.: 6 | AAGCCAATCGTTCAATACGACAACTTC | SEQ ID NO.: 5 | CTL | B53 |
| B | Tr42/43 | ASKNKEKALII | SEQ ID NO.: 8 | GCCTCCAAGAACAAGGAAAAGGCTTTGATCATC | SEQ ID NO.: 7 | CTL | B8 |

TABLE 1-continued

CTL Epitopes of the Malaria (M) String

| Cassette | Epitope | Amino acid Sequence | | DNA sequence | | Type | HLA restriction |
|---|---|---|---|---|---|---|---|
| | Tr39 | GIAGGLALL | SEQ ID NO.: 10 | GGTATCGCTGGTGGTTTGGCCTTGTTG | SEQ ID NO.: 9 | CTL | A2.1 |
| | Cp6 | MNPNDPNRNV | SEQ ID NO.: 12 | ATGAACCCTAATGACCCAAACAGAAACGTC | SEQ ID NO.: 11 | CTL | B7 |
| C | St8 | MINAYLDKL | SEQ ID NO.: 14 | ATGATCAACGCCTACTTGGACAAGTTG | SEQ ID NO.: 13 | CTL | A2.2 |
| | Ls50 | ISKYEDEI | SEQ ID NO.: 16 | ATCTCCAAGTACGAAGACGAAATC | SEQ ID NO.: 15 | CTL | B17 |
| | Pb9 | SYIPSAEKI | SEQ ID NO.: 18 | TCCTACATCCCATCTGCCGAAAAGATC | SEQ ID NO.: 17 | CTL | mouse H2-$K^d$ |
| D | Tr26 | HLGNVKYLV | SEQ ID NO.: 20 | CACTTGGGTAACGTTAAGTACTTGGTT | SEQ ID NO.: 19 | CTL | A2.1 |
| | Ls53 | KSLYDEHI | SEQ ID NO.: 22 | AAGTCTTTGTACGATGAACACATC | SEQ ID NO.: 21 | CTL | B58 |
| | Tr29 | LLMDCSGSI | SEQ ID NO.: 24 | TTATTGATGGACTGTTCTGGTTCTATT | SEQ ID NO.: 23 | CTL | A2.2 |
| E | NANP | NANPNANPNANPNANP | SEQ ID NO.: 26 | AACGCTAATCCAAACGCAAATCCGAACGCCAATCCTAACGCGAATCCC | SEQ ID NO.: 25 | B cell | |
| | TRAP AM | DEWSPCSVTCGKGTRSRKRE | SEQ ID NO.: 28 | GACGAATGGTCTCCATGTTCTGTCACTTGTGGTAAGGGTACTCGCTCTAGAAAGAGAGAA | SEQ ID NO.: 27 | Heparin binding motif | |
| F | Cp39 | YLNKIQNSL | SEQ ID NO.: 30 | TACTTGAACAAAATTCAAAACTCTTTG | SEQ ID NO.: 29 | CTL | A2.1 |
| | La72 | MEKLKELEK | SEQ ID NO.: 32 | ATGGAAAAGTTGAAAGAATTGGAAAAG | SEQ ID NO.: 31 | CTL | B8 |
| | ex23 | ATSVLAGL | SEQ ID NO.: 34 | GCTACTTCTGTCTTGGCTGGTTTG | SEQ ID NO.: 33 | CTL | B58 |
| H | CSP | DPNANPNVDPNANPNV | SEQ ID NO.: 36 | GACCCAAACGCTAACCCAAACGTTGACCCAAACGCCAACCCAAACGTC | SEQ ID NO.: 35 | T helper | Universal epitopes |
| | BCG | QVHFQPLPPAVVKL | SEQ ID NO.: 38 | CAAGTTCACTTCCAACCATTGCCTCCGGCCGTTGTCAAGTTG | SEQ ID NO.: 37 | T helper | |
| | TT | QFIKANSKFIGITE | SEQ ID NO.: 40 | CAATTCATCAAGGCCAACTCTAAGTTCATCGGTATCACCGAA | SEQ ID NO.: 39 | T helper | |

Table 1

Sequences included in the malaria epitope string. Each cassette consists of the epitopes shown above, in the order shown, with no additional sequence between epitopes within a cassette. A BglII site was added at the 5' end and a BamHI site at the 3' end, such that between cassettes in an epitope string the BamHI/BglII junction encodes GS. All epitopes are from *P. falciparum* antigens except for pb9 (*P. berghei*), BCG (*M. tuberculosis*) and TT (Tetanus). The amino acid and DNA sequences shown in the table have SEQ ID NOS. 1 to 40 in the order in which they appear.

FIG. 1 shows the construct used to express Ty-VLP with the malaria epitope cassette CABDHFE. CTL epitopes are from *P. falciparum* STARP (sporozoite threonine- and asparagine-rich protein) (st), LSA-1 (liver stage antigen 1) (ls), CSP (circumsporozoite protein) (cp), TRAP (thrombospondin-related adhesive protein) (tr), LSA-3 (liver stage antigen 3) (la) and Exp-1 (exported protein 1) (ex). Helper epitopes are from the *P. falciparum* CS protein, the *M. tuberculosis* 38 Kd antigen and Tetanus Toxoid. NANP is the antibody epitope from CS and AM is the adhesion motif from *P. falciparum* TRAP (Muller et al 1993). The length of the complete string is 229 amino acids as shown in the table 1 legend, with the amino acid sequence:

MINAYLDKLISKYEDEISYIPSAEKIGSKPNDKSLYKPKDELDYKPIVQYDNFGS [SEQ ID NO: 41]
ASKNKEKALIIGIAGGLALLMNPNDPNRNVGSHLGNVKYLVKSLYDEHILLMDCS
GSIGSDPNANPNVDPNANPNVQVHFQPLPPAVVKLQFIKANSKFIGITEGSYLNK
IQNSLMEKLKELEKATSVLAGLGSNANPNANPNANPNANPDEWSPCSVTCGKGTR
SRKREGSGK.

The HIV epitope string was also synthesised by annealing oligonucleotides. Finally the HIV and malaria epitope strings were fused by joining the BamHI site at the 3' end of the HIV epitopes to the BglII site at the 5' end of cassettes CAB to form the HM string (Table 2).

TABLE 2

CTL Epitopes of the HIV/SIV Epitope String

| Epitope | | Restriction | Origin |
|---|---|---|---|
| YLKDQQLL | (SEQ ID NO.: 42) | A24, B8 | HIV-1 gp41 |
| ERYLKDQQL | (SEQ ID NO.: 43) | B14 | HIV-1 gp41 |
| EITPIGLAP | (SEQ ID NO.: 44) | Mamu-B*01 | SIV env |
| PPIPVGEIY | (SEQ ID NO.: 45) | B35 | HIV-1 p24 |
| GEIYKRWII | (SEQ ID NO.: 46) | B8 | HIV-1 p24 |
| KRWIILGLNK | (SEQ ID NO.: 47) | B*2705 | HIV-1 p24 |
| IILGLNKIVR | (SEQ ID NO.: 48) | A33 | HIV-1 p24 |
| LGLNKIVRMY | (SEQ ID NO.: 49) | Bw62 | HIV-1 p24 |
| YNLTMKCR | (SEQ ID NO.: 50) | Mamu-A*02 | SIV env |
| RGPGRAFVTI | (SEQ ID NO.: 51) | A2, H-2Dd | HIV-1 gp120 |
| GRAFVTIGK | (SEQ ID NO.: 52) | B*2705 | HIV-1 gp120 |
| TPYDINQML | (SEQ ID NO.: 53) | B53 | HIV-2 gag |
| CTPYDINQM | (SEQ ID NO.: 54) | Mamu-A*01 | SIV gag |
| RPQVPLRPMTY | (SEQ ID NO.: 55) | B51 | HIV-1 nef |
| QVPLRPMTYK | (SEQ ID NO.: 56) | A*0301, A11 | HIV-1 nef |
| VPLRPMTY | (SEQ ID NO.: 57) | B35 | HIV-1 nef |
| AVDLSHFLK | (SEQ ID NO.: 58) | A11 | HIV-1 nef |
| DLSHFLKEK | (SEQ ID NO.: 59) | A*0301 | HIV-1 nef |
| FLKEKGGL | (SEQ ID NO.: 60) | B8 | HIV-1 nef |
| ILKEPVHGV | (SEQ ID NO.: 61) | A*0201 | HIV-1 pol |
| ILKEPVHGVY | (SEQ ID NO.: 62) | Bw62 | HIV-1 pol |
| HPDIVIYQY | (SEQ ID NO.: 63) | B35 | HIV-1 pol |
| VIYQYMDDL | (SEQ ID NO.: 64) | A*0201 | HIV-1 pol |

Table 2

Figure 2:
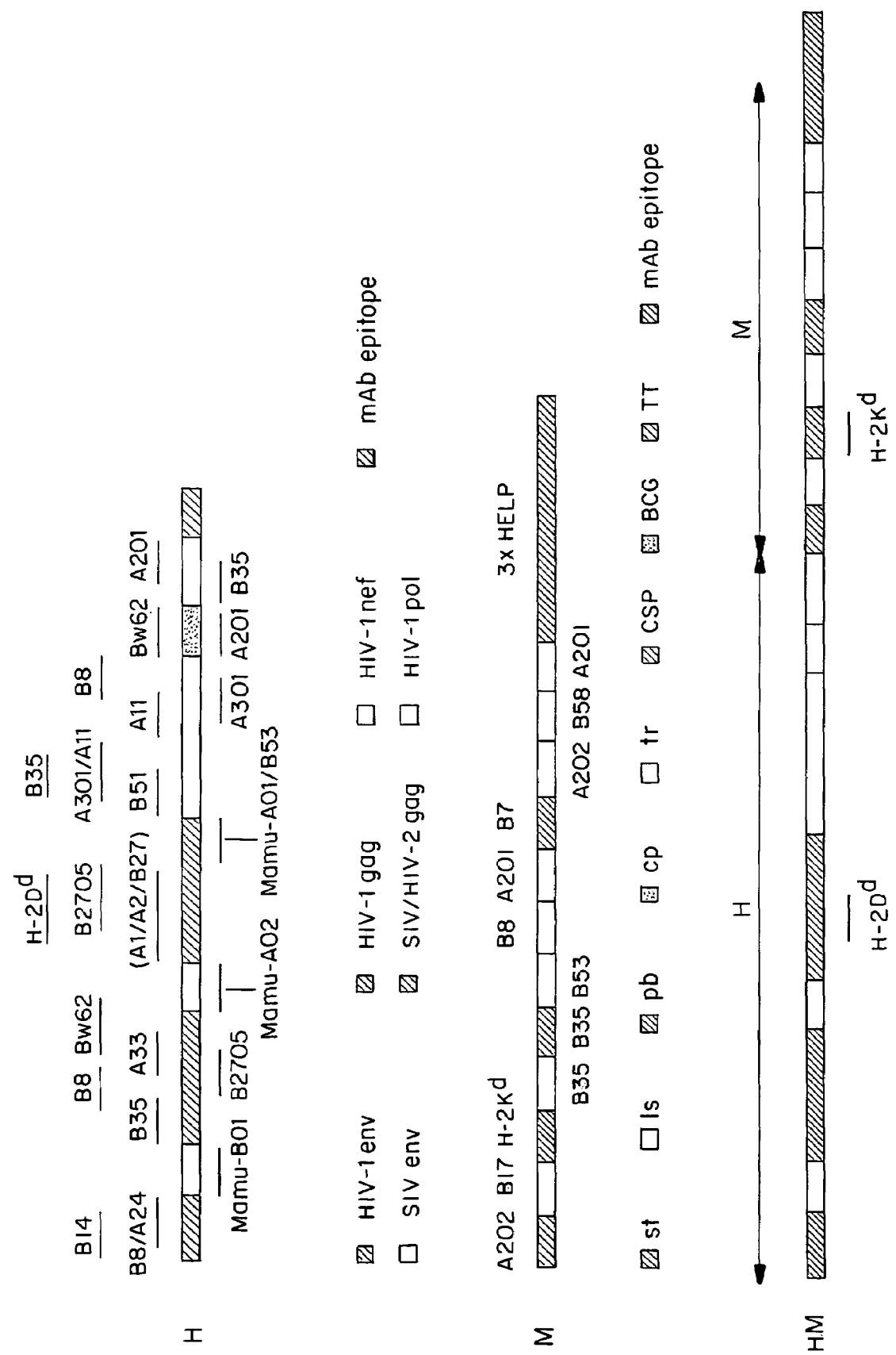
FIG. 2 shows a schematic outline of the H, M and HM proteins. The bar patterns on the schematic representations of the polyepitope proteins indicate the origin of the sequences. The positions of individual epitopes and their MHC restrictions are depicted above and below the proteins. Pb is the only epitope derived from the protein of *P. berghei*. All other epitopes in the M protein originate from proteins of *P. falciparum:* cs—circumsporozoite protein, st—STARP, ls—LSA-1 and tr—TRAP. BCG—38 kDa protein of M tuberculosis; TT—tetanus toxin.

Sequences of epitopes from HIV or SIV contained in the H epitope string and assembled as shown in FIG. 2. The amino acids in the table have SEQ ID NOS: 42 to 64 in the order in which they appear.

FIG. 2 shows a schematic outline of the H, M and HM proteins. The bar patterns on the schematic representations of the polyepitope proteins indicate the origin of the sequences (see tables 1 and 2). The positions of individual epitopes and their MHC restrictions are depicted above and below the proteins. Pb is the only epitope derived from the protein of *P. berghei*. All other epitopes in the M protein originate from proteins of *P. falciparum*: cs—circumsporozoite protein, st—STARP, ls—LSA-1 and tr—TRAP. BCG—38 kDa protein of *M. tuberculosis*; TT—tetanus toxin.

For the anti-tumour vaccine an epitope string containing CTL epitopes was generated, similar to the malaria and HIV epitope string. In this tumour epitope string published murine CTL epitopes were fused together to create the tumour epitope string with the amino acid sequence: MLPYLG-WLVF-AQHPNAELL-KHYLFRNL-SPSYVYHQF-IPN-PLLGLD [SEQ ID NO: 65]. CTL epitopes shown here were fused together. The first amino acid methionine was introduced to initiate translation.

Ty Virus-Like Particles (Vlps)

The epitope string containing cassette CABDH was introduced into a yeast expression vector to make a C-terminal in-frame fusion to the TyA protein. When TyA or TyA fusion proteins are expressed in yeast from this vector, the protein spontaneously forms virus like particles which can be purified from the cytoplasm of the yeast by sucrose gradient centrifugation. Recombinant Ty-VLPs were prepared in this manner and dialysed against PBS to remove the sucrose before injection (c.f. Layton et al. 1996).

Adenoviruses

Replication-defective recombinant Adenovirus with a deletion of the E1 genes was used in this study (McGrory et al, 1988). The Adenovirus expressed *E. coli* β-galactosidase under the control of a CMV IE promoter. For immunisations, $10^7$ pfu of virus were administered intradermally into the ear lobe.

Peptides

Peptides were purchased from Research Genetics (USA), dissolved at 10 mg/ml in DMSO (Sigma) and further diluted in PBS to 1 mg/ml. Peptides comprising CTL epitopes that were used in the experiments described herein are listed in table 3.

TABLE 3

Sequence of CTL Peptide Epitopes

| sequence | | Antigen | MHC restriction |
|---|---|---|---|
| LPYLGWLVF | (SEQ ID NO.: 66) | P1A tumour antigen | $L^d$ |
| SYIPSAEKI | (SEQ ID NO.: 67) | *P. berghei* CSP | $K^d$ |
| RGPGRAFVTI | (SEQ ID NO.: 68) | HIV gag | $D^d$ |
| TPHPARIGL | (SEQ ID NO.: 69) | *E. coli* b-galactosidase | $L^d$ |
| TYQRTRALV | (SEQ ID NO.: 70) | Influenza A virus NP | $K^d$ |
| SDYEGRLI | (SEQ ID NO.: 71) | Influenza A virus NP | $K^k$ |
| ASNENMETM | (SEQ ID NO.: 72) | Influenza A virus NP | $D^b$ |
| INVAFNRFL | (SEQ ID NO.: 73) | *P. falciparum* TRAP | $K^b$ |

The amino acid sequences in Table 3 have SEQ ID NOS: 66 to 73, in the order in which they appear in the Table.

Plasmid DNA Constructs

A number of different vectors were used for constructing DNA vaccines. Plasmid pTH contains the CMV IE promoter with intron A, followed by a polylinker to allow the introduction of antigen coding sequences and the bovine growth hormone transcription termination sequence. The plasmid carries the ampicillin resistance gene and is capable of replication in *E. coli* but not mammalian cells. This was used to make DNA vaccines expressing each of the following antigens: *P. berghei* TRAP, *P. berghei* CS, *P. falciparum* TRAP, *P. falciparum* LSA-1 (278 amino acids of the C terminus only), the epitope string containing cassettes CABDH and the HM epitope string (HIV epitopes followed by cassettes CAB). Plasmid pSG2 is similar to pTH except for the antibiotic resistance gene. In pSG2 the ampicillin resistance gene of pTH has been replaced by a kanamycin resistance gene. pSG2 was used to to make DNA vaccines expressing the following antigens: *P. berghei* PbCSP, a mouse tumour epitope string, the epitope string containing cassettes CABDH and the HM epitope string. Plasmid V1J-NP expresses influenza nucleoprotein under the control of a CMV IE promoter. Plasmids CMV-TRAP and CMV-LSA-1 are similar to pTH.TRAP and pTH. LSA-1 but do not contain intron A of the CMV promoter. Plasmids RSV.TRAP and RSV.LSA-1 contain the RSV promoter, SV40 transcription termination sequence and are tetracycline resistant. For induction of β-Galactosidase-specific CTL plasmid pcDNA3/His/LacZ (Invitrogen) was used. All DNA vaccines were prepared from *E. coli* strain DH5α using Qiagen plasmid purification columns.

Generation of Recombinant Vaccinia Viruses

Recombinant MVAs were made by first cloning the antigen sequence into a shuttle vector with a viral promoter such as the plasmid pSC11(Chakrabarti et al. 1985; Morrison et al. 1989). *P. berghei* CS and *P. falciparum* TRAP, influenza nucleoprotein and the HM and mouse tumour epitope polyepitope string were each expressed using the P7.5 promoter (Mackett et al. 1984), and *P. berghei* TRAP was expressed using the strong synthetic promoter (SSP; Carroll et al. 1995). The shuttle vectors, pSC11 or pMCO3 were then used to transform cells infected with wild-type MVA so that viral sequences flanking the promoter, antigen coding sequence and marker gene could recombine with the MVA and produce recombinants. Recombinant viruses express the marker gene (β glucuronidase or β galactosidase) allowing identification of plaques containing recombinant virus. Recombinants were repeatedly plaque purified before use in immunisations. The recombinant NYVAC-PbCSP vaccinia was previously described (Lanar et al. 1996). The wild type or Western Reserve (WR) strain of recombinant vaccinia encoding PbCSP was described previously (Satchidanandam et al. 1991).

Cells and Culture Medium

Murine cells and Epstein-Barr virus transformed chimpanzee and macaque B cells (BCL) were cultured in RPMI supplemented with 10% heat inactivated fetal calf serum (FCS). Splenocytes were restimulated with the peptides indicated (final concentration 1 µg/ml) in MEM medium with 10% FCS, 2 mM glutamine, 50 U/ml penicillin, 50 µM 2-mercaptoethanol and 10 mM Hepes pH7.2 (Gibco, UK).

Animals

Mice of the strains indicated, 6-8 weeks old were purchased from Harlan Olac (Shaws Farm, Blackthorn, UK). Chimpanzees H1 and H2 were studied at the Biomedical Primate Research Centre at Rijswick, The Netherlands. Macaques were studied at the University of Oxford.

Immunisations

Plasmid DNA immunisations of mice were performed by intramuscular immunisation of the DNA into the musculus tibialis under anaesthesia. Mouse muscle was sometimes pretreated with 50 µl of 1 mM cardiotoxin (Latoxan, France) 5-9 days prior to immunisation as described by Davis et al (1993), but the presence or absence of such pre-treatment was not found to have any significant effect on immunogenicity or protective efficacy. MVA immunisation of mice was performed by either intramuscular (i.m.), intravenous (into the lateral tail vein) (i.v.), intradermal (i.d.), intraperitoneal (i.p.) or subcutaneous (s.c.) immunisation. Plasmid DNA and MVA immunisation of the chimpanzees H1 and H2 was performed under anaesthesia by intramuscular immunisation of leg muscles. For these chimpanzee immunisations the plasmid DNA was co-administered with 15 micrograms of human GM-CSF as an adjuvant. Recombinant MVA administration to the chimpanzees was by intramuscular immunisation under veterinary supervision. Recombinant human GM-CSF was purchased from Sandoz (Camberley, UK). For plasmid DNA immunisations using a gene gun, DNA was precipitated onto gold particles. For intradermal delivery, two different types of gene guns were used, the Acell and the Oxford Bioscience device (PowderJect Pharmaceuticals, Oxford, UK).

Elispot Assays

CD8+ T cells were quantified in the spleens of immunised mice without in vitro restimulation using the peptide epitopes indicated and the ELISPOT assay as described by Miyahara et al (1993). Briefly, 96-well nitrocellulose plates (Miliscreen MAHA, Millipore, Bedford UK) were coated with 15 µg/ml of the anti-mouse interferon-γ monoclonal antibody R4 (EACC) in 50 µl of phosphate-buffered saline (PBS). After overnight incubation at 4° C. the wells were washed once with PBS and blocked for 1 hour at room temperature with 100 µl RPMI with 10% FCS. Splenocytes from immunised mice were resuspended to $1 \times 10^7$ cells/ml and placed in duplicate in the antibody coated wells and serially diluted. Peptide was added to each well to a final concentration of 1 µg/ml. Additional wells without peptide were used as a control for peptide-dependence of interferon-γ secretion. After incubation at 37° C. in 5% $CO_2$ for 12-18 hours the plates were washed 6 times with PBS and water. The wells were then incubated for 3 hours at room temperature with a solution of 1 µg/ml of biotinylated anti-mouse interferon-γ monoclonal antibody XMG1.2 (Pharmingen, CA, USA) in PBS. After further washes with PBS, 50 µl of a 1 µg/ml solution of streptavidin-alkaline-phosphatase polymer (Sigma) was added for 2 hours at room temperature. The spots were developed by adding 50 µl of an alkaline phosphatase conjugate substrate solution (Biorad, Hercules, Calif., USA). After the appearance of spots the reaction was stopped by washing with water. The number of spots was determined with the aid of a stereomicroscope.

ELISPOT assays on the chimpanzee peripheral blood lymphocytes were performed using a very similar method employing the assay and reagents developed to detect human CD8 T cells (Mabtech, Stockholm).

CTL Assays

CTL assays were performed using chromium labelled target cells as indicated and cultured mouse spleen cells as effector cells as described by Allsopp et al. (1996). CTL assays using chimpanzee or macaque cells were performed as described for the detection of human CTL by Hill et aL (1992) using EBV-transformed autologous chimpanzee chimpanzee or macaque B cell lines as target cells.

*P. Berghei* Challenge

Mice were challenged with 2000 (BALB/c) or 200 (C57BL/6) sporozoites of the *P. berghei* ANKA strain in 200 ml RPMI by intravenous inoculation as described (Lanar et al. 1996). These sporozoites were dissected from the salivary glands of *Anopheles stephensi* mosquitoes maintained at 18°

C. for 20-25 days after feeding on infected mice. Blood-stage malaria infection, indicating a failure of the immunisation, was detected by observing the appearance of ring forms of *P. berghei* in Giemsa-stained blood smears taken at 5-12 days post-challenge.

P. Falciparum Challenge

The chimpanzees were challenged with 20,000 *P. falciparum* sporozoites of the NF54 strain dissected from the salivary glands of *Anopheles gambiae* mosquitoes, by intravenous inoculation under anaesthesia. Blood samples from these chimpanzees were examined daily from day 5 after challenge by microscopy and parasite culture, in order to detect the appearance of low levels of *P. falciparum* parasites in the peripheral blood.

P815 Tumour Challenges

Mice were challenged with $1 \times 10^5$ P815 cells in 200 μl of PBS by intravenous inoculation. Animals were monitored for survival.

Influenza Virus Challenges

Mice were challenged with 100 haemagglutinating units (HA) of influenza virus A/PR/8/34 by intranasal inoculation. Following challenge the animals were weighed daily and monitored for survival.

Determining Peptide Specific CTL Using Tetramers

Tetrameric complexes consisting of Mamu-A*01-heavy chain and $\beta_2$-microglobulin were made as described by Ogg et al (1998). DNA coding for the leaderless extracellular portion of the Mamu-A*01 MHC class I heavy chain was PCR-amplified from cDNA using 5'primer MamuNdeI: 5'-CCT GAC TCA GAC CAT ATG GGC TCT CAC TCC ATG [SEQ ID NO: 74] and 3' primer: 5'-GTG ATA AGC TTA ACG ATG ATT CCA CAC CAT TTT CTG TGC ATC CAG AAT ATG ATG CAG GGA TCC CTC CCA TCT CAG GGT GAG GGG C [SEQ ID NO: 75]. The former primer contained a NdeI restriction site, the latter included a HindIII site and encoded for the bioinylation enzyme BirA substrate peptide. PCR products were digested with NdeI and HindIII and ligated into the same sites of the polylinker of bacterial expression vector pGMT7. The rhesus monkey gene encoding a leaderless $\beta_2$-microglobulin was PCR amplifed from a cDNA clone using primers B2MBACK: 5'-TCA GAC CAT ATG TCT CGC TCC GTG GCC [SEQ ID NO: 76] and B2MFOR: 5'-TCA GAC AAG CTT TTA CAT GTC TCG ATC CCA C [SEQ ID NO: 77] and likewise cloned into the NdeI and HindIII sites of pGMT7. Both chains were expressed in *E. coli* strain BL-2 1, purified from inclusion bodies, refolded in the presence of peptide CTPYDINQM [SEQ ID NO: 54], biotinylated using the BirA enzyme (Avidity) and purified with FPLC and monoQ ion exchange columns. The amount of biotinylated refolded MHC-peptide complexes was estimated in an ELISA assay, whereby monomeric complexes were first captured by conformation sensitive monoclonal antibody W6/32 and detected by alkaline phosphatase (AP)-conjugated streptavidin (Sigma) followed by colorimetric substrate for AP. The formation of tetrameric complexes was induced by addition of phycoerythrin (PE)-conjugated streptavidin (ExtrAvidin; Sigma) to the refolded biotinylated monomers at a molar ratio of MHC-peptide:PE-streptavidin of 4:1. The complexes were stored in the dark at 4° C. These tetramers were used to analyse the frequency of Mamu-A*01/gag-specific CD8+ T cells in peripherial blood lymphocytes (PBL) of immunised macaques.

Example 2

Immunogenicity Studies in Mice

Previous studies of the induction of CTL against epitopes in the circumsporozoite (CS) protein of *Plasmodium berghei* and *Plasmodium yoelii* have shown variable levels of CTL induction with different delivery systems. Partial protection has been reported with plasmid DNA (Sedegah et al. 1994), influenza virus boosted by replicating vaccinia virus (Li et al. 1991), adenovirus (Rodrigues et al 1997) and particle delivery systems (Schodel et al. 1994). Immunisation of mice intramuscularly with 50 micrograms of a plasmid encoding the CS protein produced moderate levels of CD8+ cells and CTL activity in the spleens of these mice after a single injection (FIGS. 3, 4A-4D).

Figure 3:
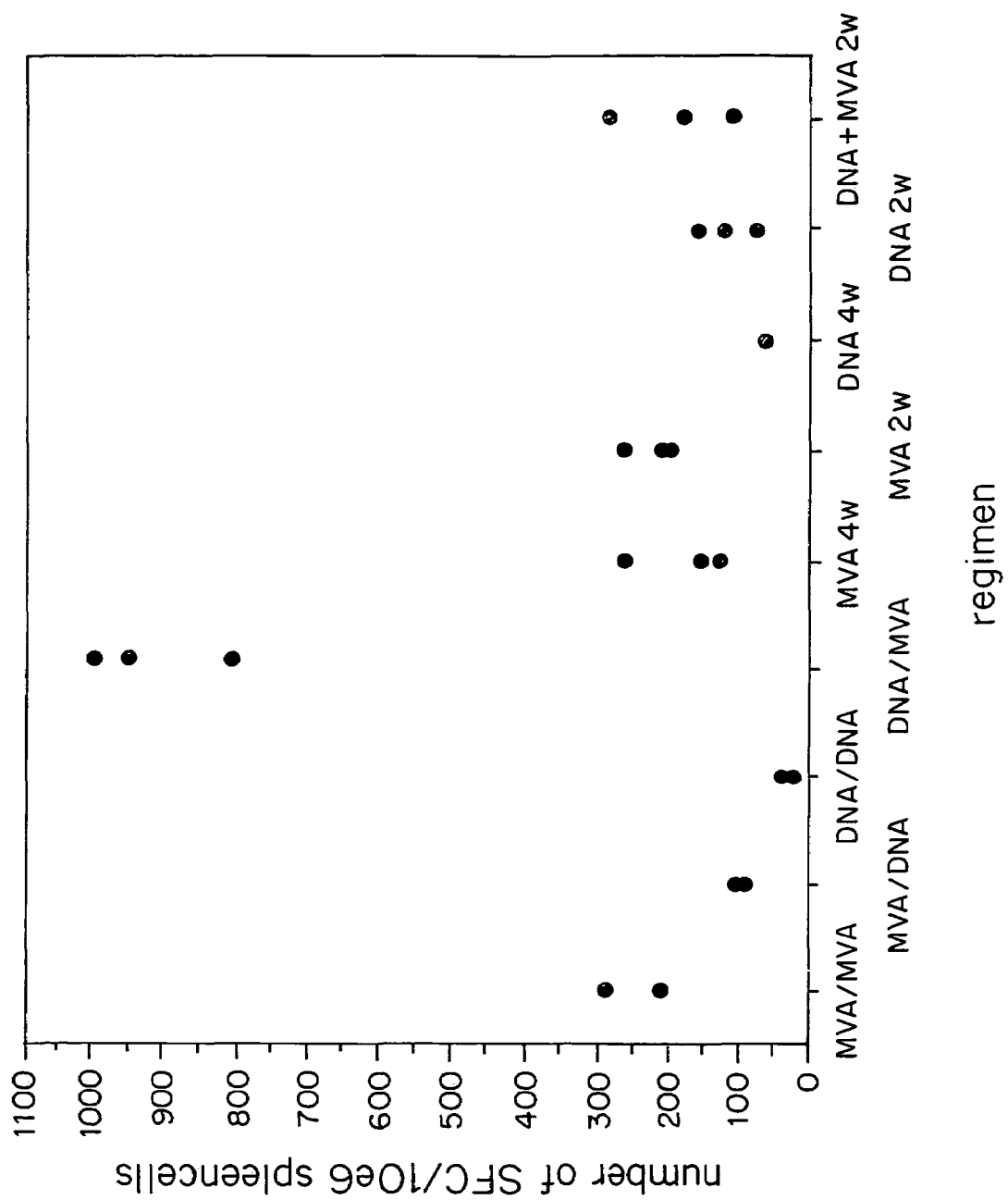
FIG. 3 shows malaria CD8 T cell ELISPOT data following different immunisation regimes. Results are shown as the number of peptide-specific T cells per million splenocytes.
Figure 4A:
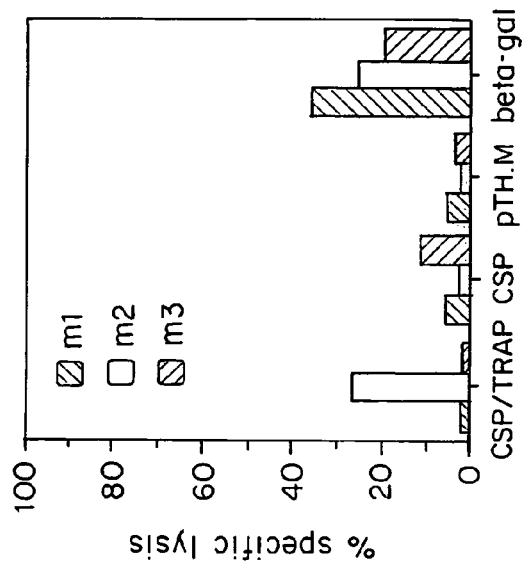
FIGS. 4A-4D show that malaria CD8 T cell ELISPOT (FIGS. 4A and 4C) and CTL levels (FIGS. 4B and 4D) are substantially boosted by a recombinant MVA immunisation following priming with a plasmid DNA encoding the same antigen. The ELISPOT counts are presented on a logarithmic scale.
Figure 4B:
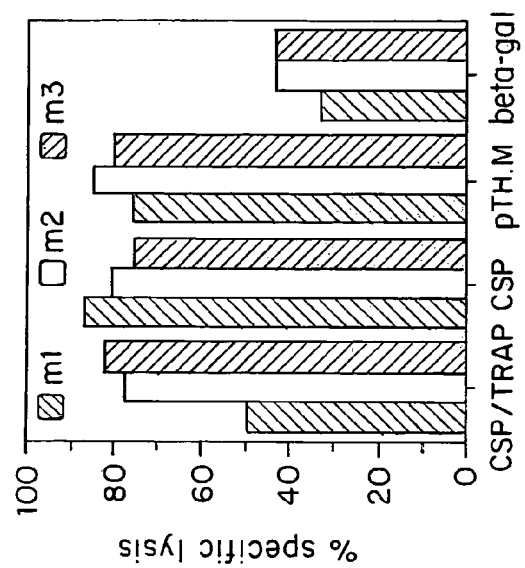
Figure 4C:
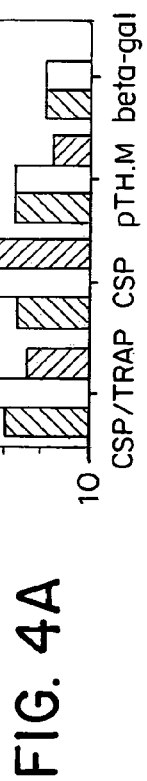
Figure 4D:
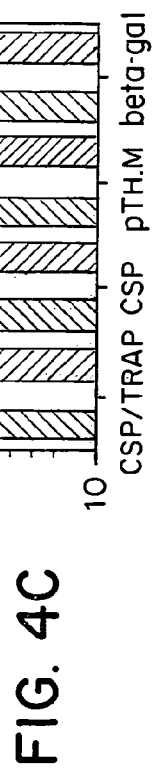

For comparison groups of BALB/c mice (n=5) were injected intravenously with $10^6$ ffu/pfu of recombinant vaccinia viruses of different strains (WR, NYVAC and MVA) all expressing *P. berghei* CSP. The frequencies of peptide-specific CD8+ T cells were measured 10 days later in an ELISPOT assay. MVA.PbCSP induced 181±48, NYVAC 221±27 and WR 94±19 (mean±standard deviation) peptide-specific CD8+ T cells per million splenocytes. These results show that surprisingly replication-impaired vaccinia viruses are superior to replicating strains in priming a CD8+ T cell response. We then attempted to boost these moderate CD8+ T cell responses induced by priming with either plasmid DNA or MVA using homologous or heterologous vectors. A low level of CD8+ T cells was observed after two immunisations with CS recombinant DNA vaccine alone, the recombinant MVA vaccine alone or the recombinant MVA followed by recombinant DNA (FIG. 3). A very much higher level of CD8+ T cells was observed by boosting the DNA-primed immune response with recombinant MVA. In a second experiment using ten mice per group the enhanced immunogenicity of the DNA/MVA sequence was confirmed: DNA/MVA 856±201; MVA/DNA 168±72; MVA/MVA 345±90; DNA/DNA 92±46. Therefore the sequence of a first immunisation with a recombinant plasmid encoding the CS protein followed by a second immunisation with the recombinant MVA virus yielded the highest levels of CD8+ T lymphocyte response after immunisation.

FIG. 3 shows malaria CD8 T cell ELISPOT data following different immunisation regimes. Results are shown as the number of peptide-specific T cells per million splenocytes. Mice were immunised either with the PbCSP-plasmid DNA or the PbCSP-MVA virus or combinations of the two as shown on the X axis, at two week intervals and the number of splenocytes specific for the pb9 malaria epitope assayed two weeks after the last immunisation. Each point represents the number of spot-forming cells (SFCs) measured in an individual mouse. The highest level of CD8+ T cells was induced by priming with the plasmid DNA and boosting with the recombinant MVA virus. This was more immunogenic than the reverse order of immunisation (MVA/DNA), two DNA immunisations (DNA/DNA) or two MVA immunisations (MVA/MVA). It was also more immunogenic than the DNA and MVA immunisations given simultaneously (DNA+MVA 2 w), than one DNA immunisation (DNA 4 w) or one MVA immunisation given at the earlier or later time point (MVA 2 w and MVA 4 w).

FIGS. 4A-4D shows that malaria CD8 T cell ELISPOT and CTL levels are substantially boosted by a recombinant MVA immunisation following priming with a plasmid DNA encoding the same antigen. A AND C. CD8+ T cell responses were measured in BALB/c mice using the g-interferon ELISPOT assay on fresh splenocytes incubated for 18 h with the $K^d$ restricted peptide SYIPSAEKI [SEQ ID NO: 67] from *P. berghei* CSP and the $L^d$ restricted peptide TPHPARIGL [SEQ ID NO: 69] from *E. coli* β-Galactosidase. Note that the ELISPOT counts are presented on a logarithmic scale. B and D. Splenocytes from the same mice were also assayed in conventional $^{51}$Cr-release assays at an effector: target ration of 100:1 after 6 days of in vitro restimulation with the same peptides (1 μg/ml).

The mice were immunised with plasmid DNA expressing either *P. berghei* CSP and TRAP, PbCSP alone, the malaria epitope cassette including the *P. berghei* CTL epitope (labelled pTH.M), or β-Galactosidase. ELISPOT and CTL levels measured in mice 23 days after one DNA immunisation are shown in A and B respectively. The same assays were performed with animals that received additionally 1×10$^7$ ffu of recombinant MVA expressing the same antigen(s) two weeks after the primary immunisation. The ELISPOT and CTL levels in these animals are shown in C and D respectively. Each bar represents data from an individual animal.

Studies were also undertaken of the immunogenicity of the epitope string HM comprising both HIV and malaria epitopes in tandem. Using this epitope string again the highest levels of CD8+ T cells and CTL were generated in the spleen when using an immunisation with DNA vaccine followed by an immunisation with a recombinant MVA vaccine (Table 4, FIG. 5).

TABLE 4

Immunogenicity of Various DNA/MVA Combinations as Determined by Elispot Assays

| Immunisation 1 | Immunisation 2 | HIV epitope | Malaria epitope |
|---|---|---|---|
| DNA-HM | DNA-HM | 56 ± 26 | 4 ± 4 |
| MVA-HM | MVA-HM | 786 ± 334 | 238 ± 106 |
| MVA-HM | DNA-HM | 306 ± 78 | 58 ± 18 |
| DNA-HM | MVA-HM | 1000 ± 487 | 748 ± 446 |
| None | DNA-HM | 70 ± 60 | 100 ± 10 |
| None | MVA-HM | 422 ± 128 | 212 ± 94 |

Table 4 shows the results of ELISPOT assays performed to measure the levels of specific CD8+ T cells to HIV and malaria epitopes following different immunisation regimes of plasmid DNA and MVA as indicated. The numbers are spot-forming cells per million splenocytes. The HM epitope string is illustrated in FIG. 2. BALB/c mice were used in all cases. The malaria epitope was pb9 as in FIGS. 2 and 3. The HIV epitope was RGPGRAFVTI [SEQ ID NO: 51]. The immunisation doses were 50 μg of plasmid DNA or 10$^7$ focus-forming units (ffu) of recombinant MVA. All immunisations were intramuscular. The interval between immunisations 1 and 2 was from 14-21 days in all cases.

Figure 5:
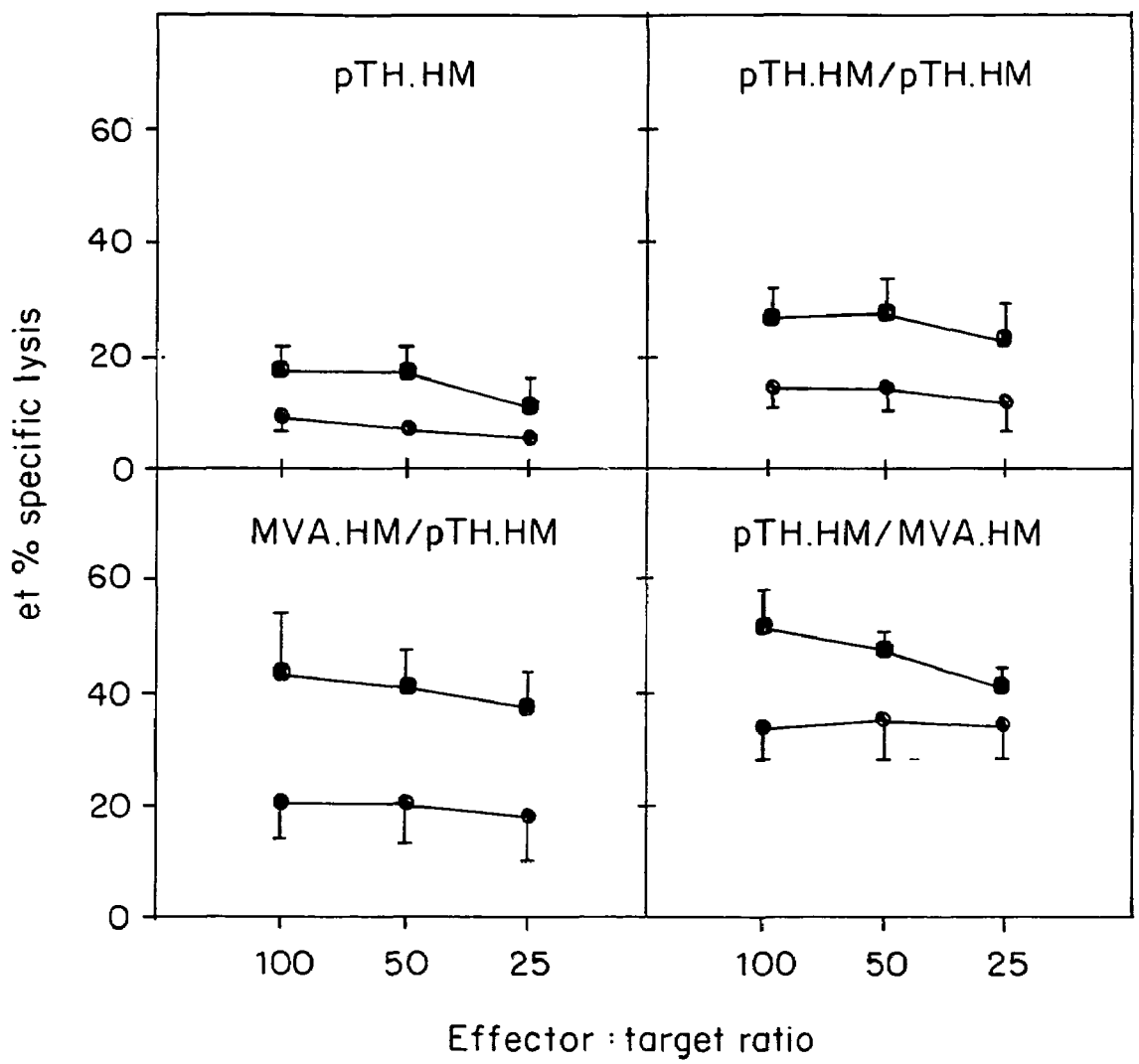
FIG. 5 shows the CTL responses induced in BALB/c mice to malaria and HIV epitopes by various immunisation regimes employing plasmid DNA and recombinant MVA. Levels of specific lysis at various effector to target ratios are shown.

FIG. 5 shows the CTL responses induced in BALB/c mice to malaria and HIV epitopes by various immunisation regimes employing plasmid DNA and recombinant MVA. Mice were immunised intramuscularly as described in the legend to table 3 and in methods. High levels of CTL (>30% specific lysis at effector/target ration of 25:1) were observed to both the malaria and HIV epitopes only after priming with plasmid DNA and boosting with the recombinant MVA. The antigen used in this experiment is the HIV-malaria epitope string. The recombinant MVA is denoted MVA.HM and the plasmid DNA expressing this epitope string is denoted pTH.HM. Levels of specific lysis at various effector to target ratios are shown. These were determined after 5 days in vitro restimulation of splenocytes with the two peptides pb9 and RGPGRAFVTI [SEQ ID NO: 51].

Comparison of numerous delivery systems for the induction of CTL was reported by Allsopp et al. (1996). Recombinant Ty-virus like particles (Ty-VLPs) and lipid-tailed malaria peptides both gave good CTL induction but Ty-VLPs were better in that they required only a single immunising dose for good CTL induction. However, as shown here even two doses of Ty particles fail to induce significant protection against sporozoite challenge (Table 7, line 1). Immunisation with a recombinant modified vaccinia Ankara virus encoding the circumsporozoite protein of *P. berghei* also generates good levels of CTL. However, a much higher level of CD8+ T cell response is achieved by a first immunisation with the Ty-VLP followed by a second immunisation with the MVA CS vaccine (Table 5).

TABLE 5

Immunogenicity of Various Ty-VLP/MVA Combinations as Determined by ELISPOT and CTL Assays

| Immunisation 1 | Immunisation 2 | ELISPOT No | % Specific Lysis |
|---|---|---|---|
| Ty-CABDH | Ty-CABDH | 75 | 15 |
| MVA.PbCSP | MVA.PbCSP | 38 | 35 |
| Ty-CABDH | MVA.PbCSP | 225 | 42 |
| Ty-CABDH | MVA.HM | 1930 | nd |

Table 5 Results of ELISPOT and CTL assays performed to measure the levels of specific CD8+ T cells to the malaria epitope pb9 following different immunisation regimes of Ty-VLPs and recombinant MVA virus as indicated. The CTL and ELISPOT data are from different experiments. The ELISPOT levels (spots per million splenocytes) are measured on un-restimulated cells and the CTL activity, indicated as specific lysis at an effector to target ratio of 40:1, on cells restimulated with pb9 peptide in vitro for 5-7 days. Both represent mean levels of three mice. BALB/c mice were used in all cases. The immunisation doses were 50 μg of Ty-VLP or 10$^7$ ffu (foci forming units) of recombinant MVA. All immunisations were intramuscular. The interval between immunisations 1 and 2 was from 14-21 days. MVA.HM includes cassettes CAB.

Priming of an Immune Response with DNA Delivered by a Gene Gun and Boosting with Recombinant MVA Immunogenicity and Challenge The use of a gene gun to deliver plasmid DNA intradermally and thereby prime an immune response that could be boosted with recombinant MVA was investigated. Groups of BALB/c mice were immunised with the following regimen:

I) Three gene gun immunisations with pTH.PbCSP (4 mg per immunisation) at two week intervals II) Two gene gun immunisations followed by MVA i.v. two weeks later III) One intramuscular DNA immunisation followed by MVA i.v. two weeks later.

The immunogenicity of the three immunisation regimens was analysed using ELISPOT assays. The highest frequency of specific T cells was observed with two gene gun immunisations followed by an MVA i.v. boost and the intramuscular DNA injection followed an MVA i.v. boost (FIG. 6).

Figure 6:
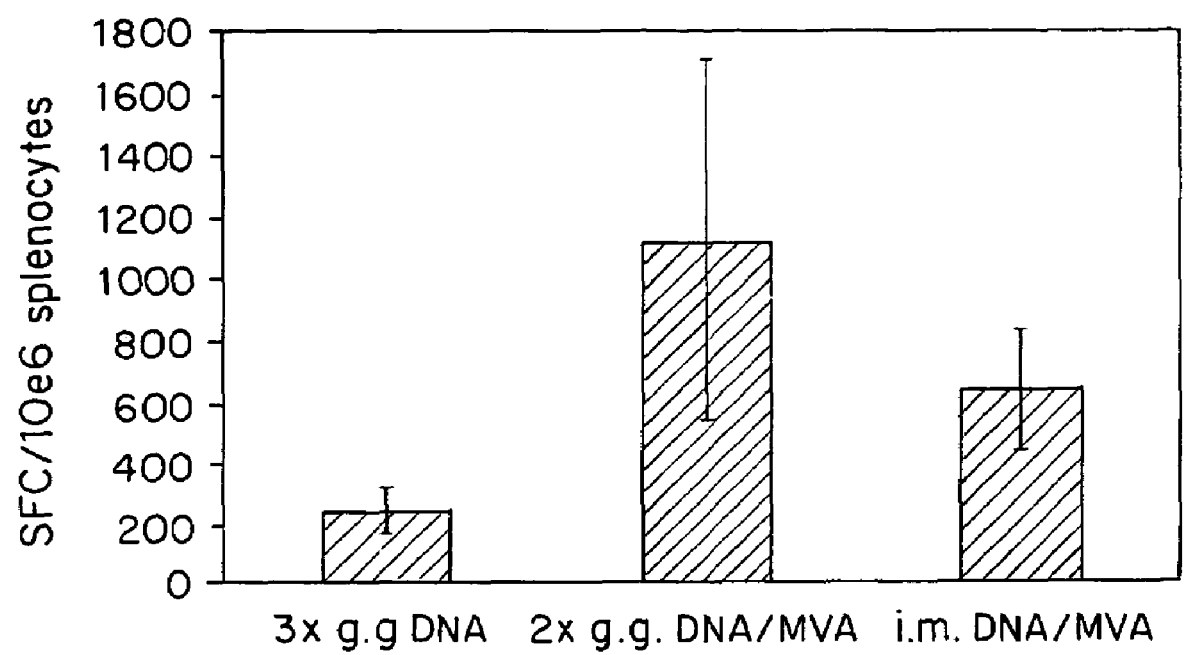
FIG. 6 shows the results of ELISPOT assays performed to measure the levels of specific CD8+ T cells to the malaria epitope pb9 following different immunisation regimes. Groups of BALB/c mice (n=3) were immunised as indicated (g.g.=gene gun). The time between all immunisations was 14 days. ELISPOT assays were done two weeks after the last immunisation.
Figure 7A:
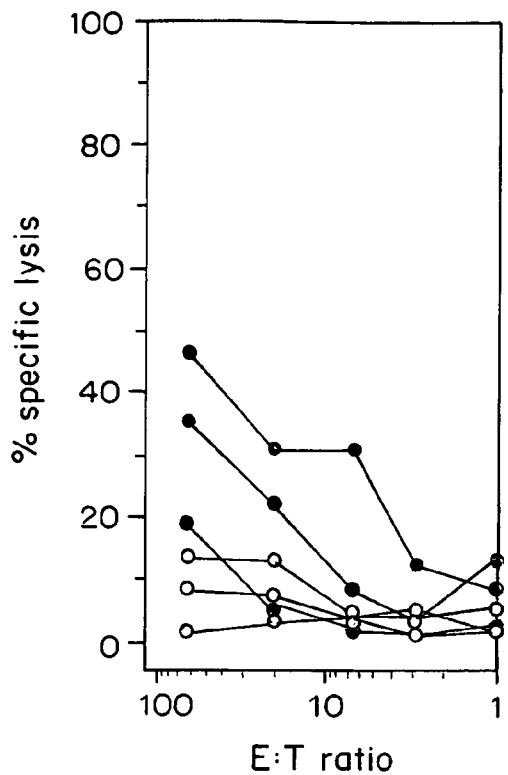
FIGS. 7A-7E show the CTL responses against influenza NP in different mouse strains. Mice of different strains were immunised twice two weeks apart with a DNA vaccine V1J-NP encoding for the influenza nucleoprotein (open circles) or primed with the same DNA vaccine and two weeks later boosted with recombinant MVA expressing influenza virus nucleoprotein (closed circles). The CTL activity was determined in a standard $^{51}$Cr-release assay with MHC class I-matched target cells.
Figure 7B:
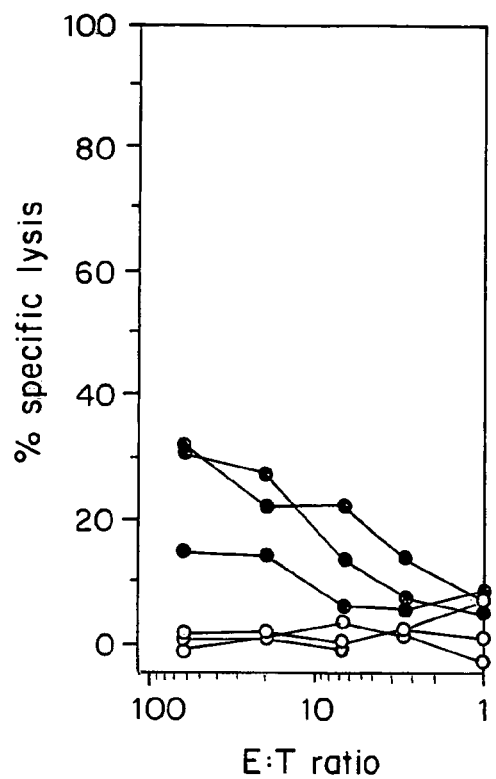
Figure 7C:
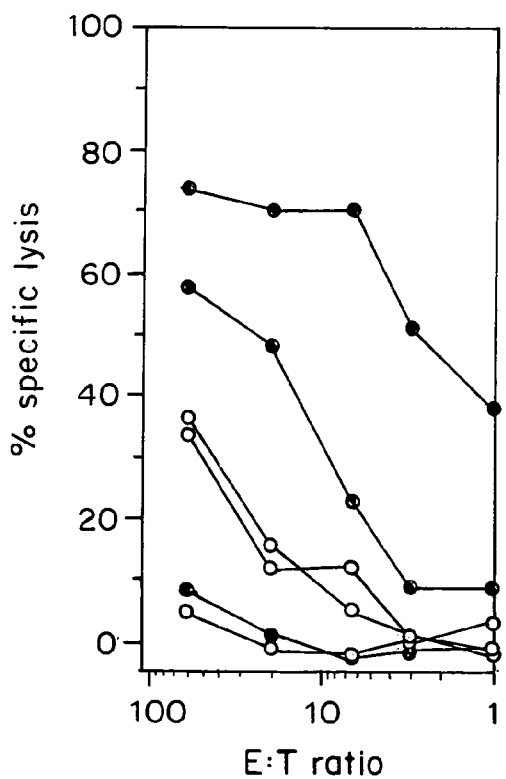
Figure 7D:
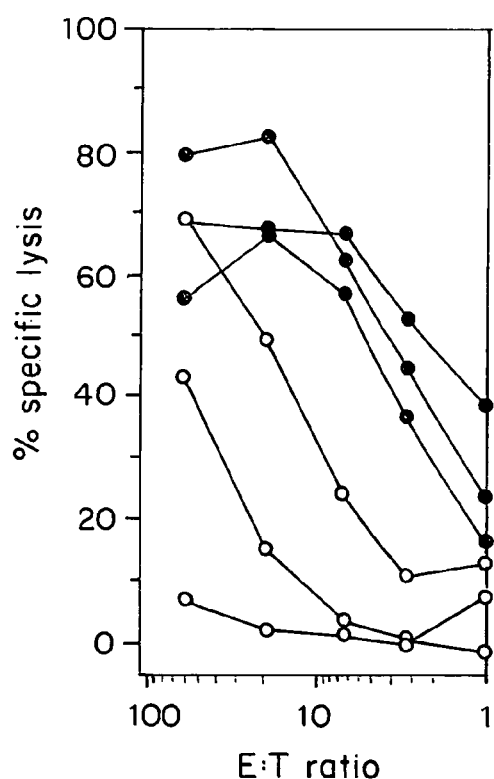
Figure 7E:
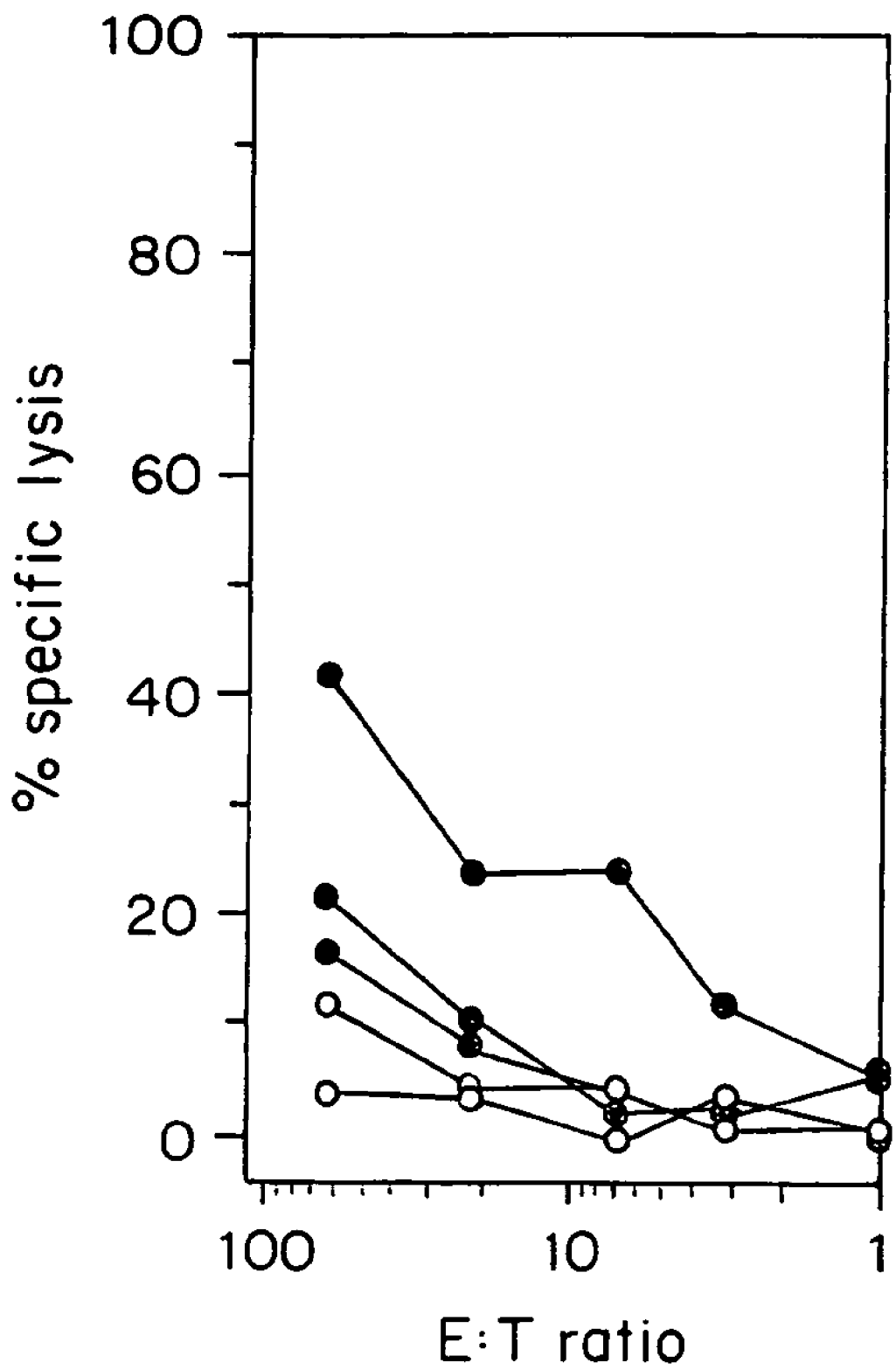
Figure 8A:
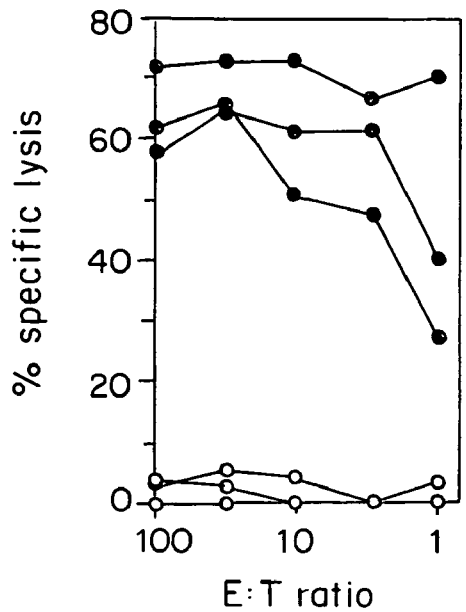
FIGS. 8A-8H show CTL responses against different antigens induced in different inbred mouse strains. Mice were immunised with two DNA vaccine immunisations two weeks apart (open circles) or primed with a DNA vaccine and two weeks later boosted with a recombinant MVA expressing the same antigen (closed circles). The strains and antigens were.
Figure 8B:
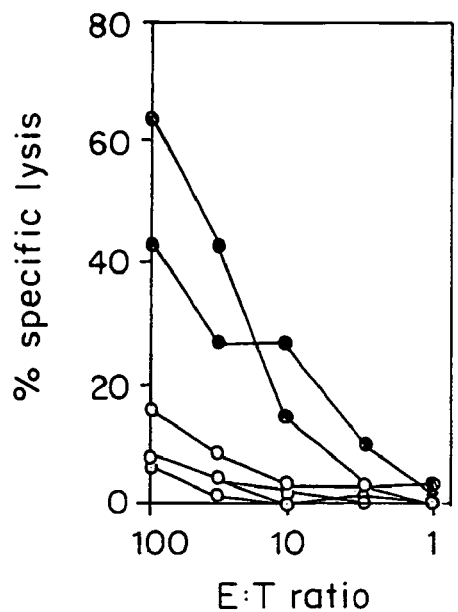
Figure 8C:
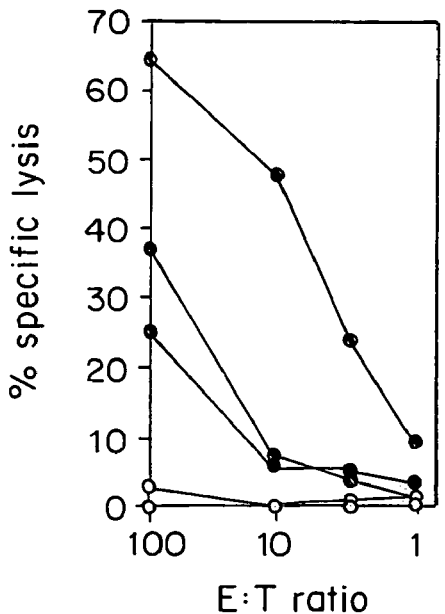
Figure 8D:
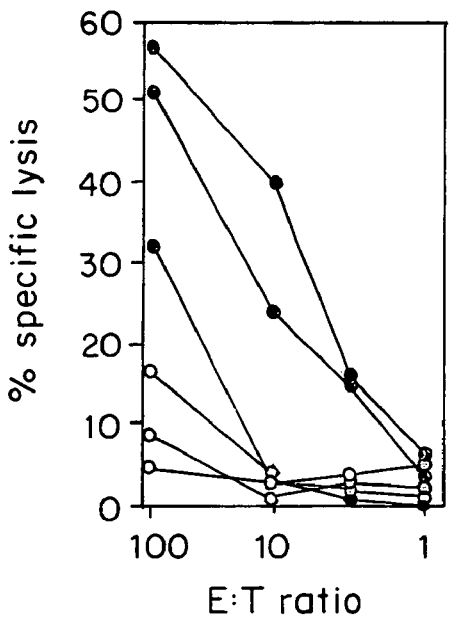
Figure 8E:
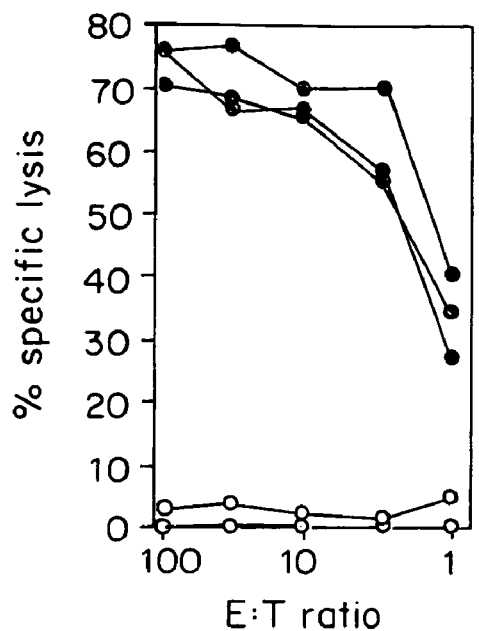
Figure 8F:
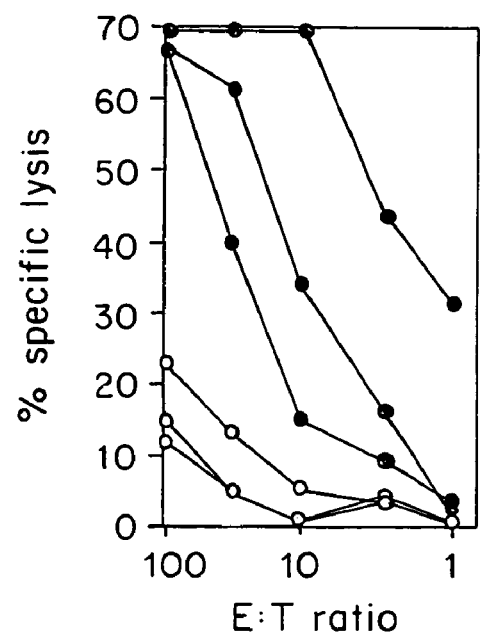
Figure 8G:
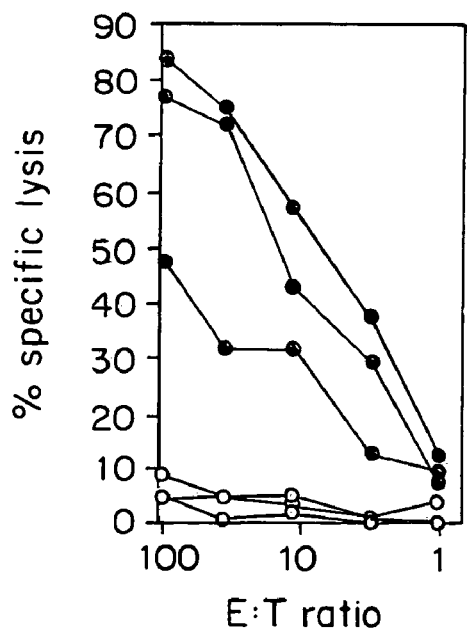
Figure 8H:
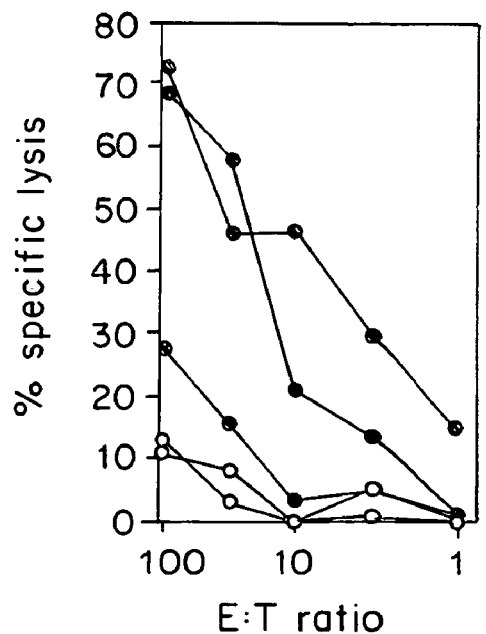

FIG. 6 shows the results of ELISPOT assays performed to measure the levels of specific CD8+ T cells to the malaria epitope pb9 following different immunisation regimes. Groups of BALB/c mice (n=3) were immunised as indicated (g.g.=gene gun). The time between all immunisations was 14 days. ELISPOT assays were done two weeks after the last immunisation.

CTL Induction to the Same Antigen in Different Mouse Strains

To address the question whether the boosting effect described above in BALB/c mice with two CTL epitopes SYIPSAEKI [SEQ ID NO: 67] derived from P. berghei CSP and RGPGRAFVTI [SEQ ID NO: 68] derived from HIV is a universal phenomenon, two sets of experiments were carried out. CTL responses to the influenza nucleoprotein were studied in five inbred mouse strains. In a first experiment three published murine CTL epitopes derived from the influenza nucleoprotein were studied (see Table 3). Mice of three different H-2 haplotypes, BALB/c and DBA/2 (H-$2^d$), C57BL/6 and 129 (H-$2^b$); CBA/J (H-$2^k$), were used. One set of animals was immunised twice at two week intervals with the plasmid V1J-NP encoding the influenza nucleoprotein. Another set of identical animals was primed with V1J-NP and two weeks later boosted intravenously with $10^6$ ffu of MVA.NP, expressing influenza virus NP. The levels of CTL in individual mice were determined in a $^{51}$Cr-release assay with peptide re-stimulated splenocytes. As shown in FIGS. 7A-7E, the DNA priming/MVA boosting immunisation regimen induced higher levels of lysis in all the mouse strains analysed and is superior to two DNA injections.

FIGS. 7A-7E show the CTL responses against influenza NP in different mouse strains. Mice of different strains were immunised twice two weeks apart with a DNA vaccine V1J-NP encoding for the influenza nucleoprotein (open circles) or primed with the same DNA vaccine and two weeks later boosted with recombinant MVA expressing influenza virus nucleoprotein (closed circles). Two weeks after the last immunisation splenocytes were restimulated in vitro with the respective peptides (Table 3). The CTL activity was determined in a standard $^{51}$Cr-release assay with MHC class I-matched target cells.

CTL Induction to Different Antigens in Different Mouse Strains

The effect of MVA boosting on plasmid DNA-primed immune responses was further investigated using different antigens and different inbred mouse strains. Mice of different strains were immunised with different antigens using two DNA immunisations and compared with DNA/MVA immunisations. The antigens used were E. coli β-galactosidase, the malaria/HIV epitope string, a murine tumour epitope string and P. falciparum TRAP. Compared with two DNA immunisations the DNA-priming/MVA-boosting regimen induced higher levels of CTL in all the different mouse strains and antigen combinations tested (FIGS. 8A-8H).

FIGS. 8A-8H show CTL responses against different antigens induced in different inbred mouse strains. Mice were immunised with two DNA vaccine immunisations two weeks apart (open circles) or primed with a DNA vaccine and two weeks later boosted with a recombinant MVA expressing the same antigen (closed circles). The strains and antigens were: C57BL/6; P. falciparum TRAP in A. DBA/2; E. coli b-galactosidase in B. BALB/c; HM epitope string CTL activity against malaria peptide (pb9) in C. DBA/2; HM epitope string CTL activity against pb9 in D. BALB/c; HM epitope string CTL activity against HIV peptide in E. DBA/2; HM epitope string CTL activity against HIV peptide in F. BALB/c; tumour epitope string CTL activity against P1A-derived peptide in G. DBA/2; tumour epitope string CTL activity against P1A-derived peptide in H. Sequences of peptide epitopes are shown in table 3. Each curve shows the data for an individual mouse.

Sporozoites can Efficiently Prime an Immune Response that is Boostable by MVA

Humans living in malaria endemic areas are continuously exposed to sporozoite inoculations. Malaria-specific CTL are found in these naturally exposed individuals at low levels. To address the question whether low levels of sporozoite induced CTL responses can be boosted by MVA, BALB/c mice were immunised with irradiated (to prevent malaria infection) P. berghei sporozoites and boosted with MVA. Two weeks after the last immunisation splenocytes were re-stimulated and tested for lytic activity. Two injections with 50 or 300+500 sporozoites induced very low or undetectable levels of lysis. Boosting with MVA induced high levels of peptide specific CTL. MVA alone induced only moderate levels of lysis (FIGS. 9A-9E).

Figure 9A:
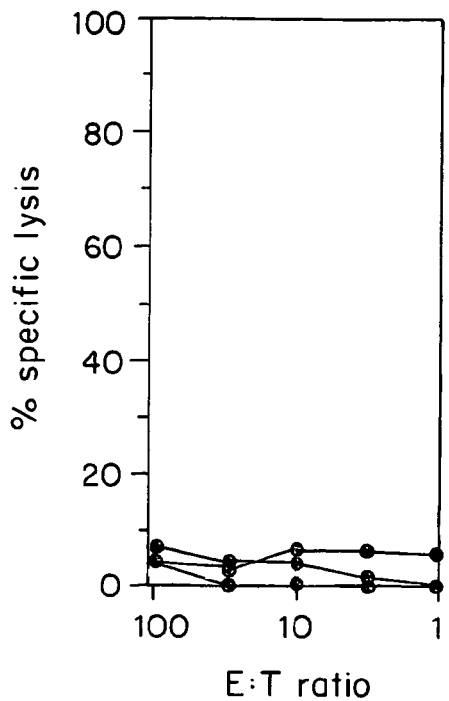
Figure 9B:
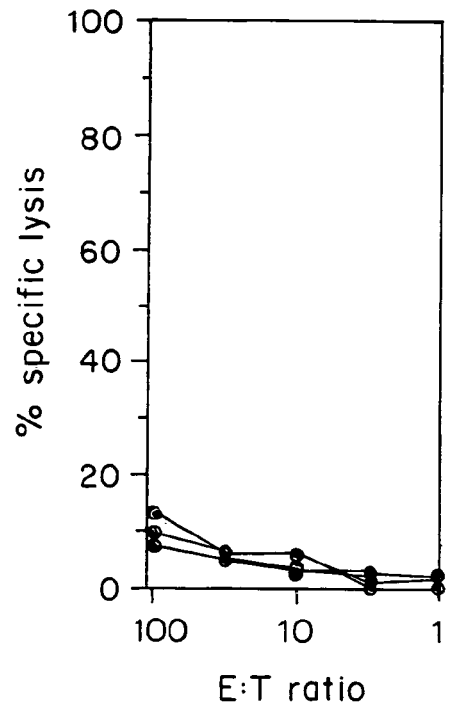
Figure 9C:
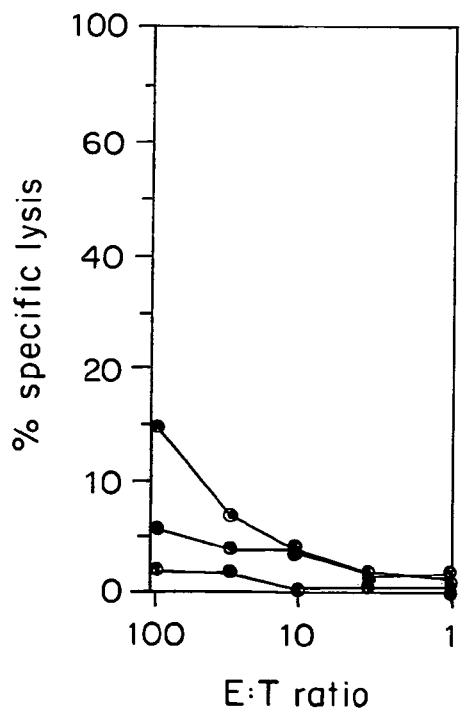
Figure 9D:
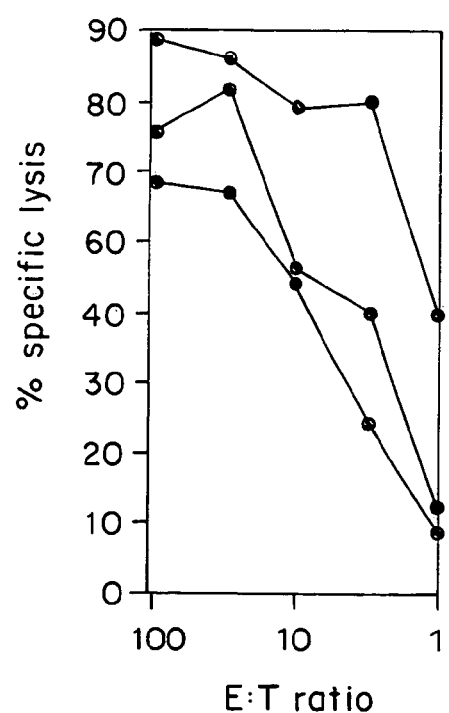
Figure 9E:
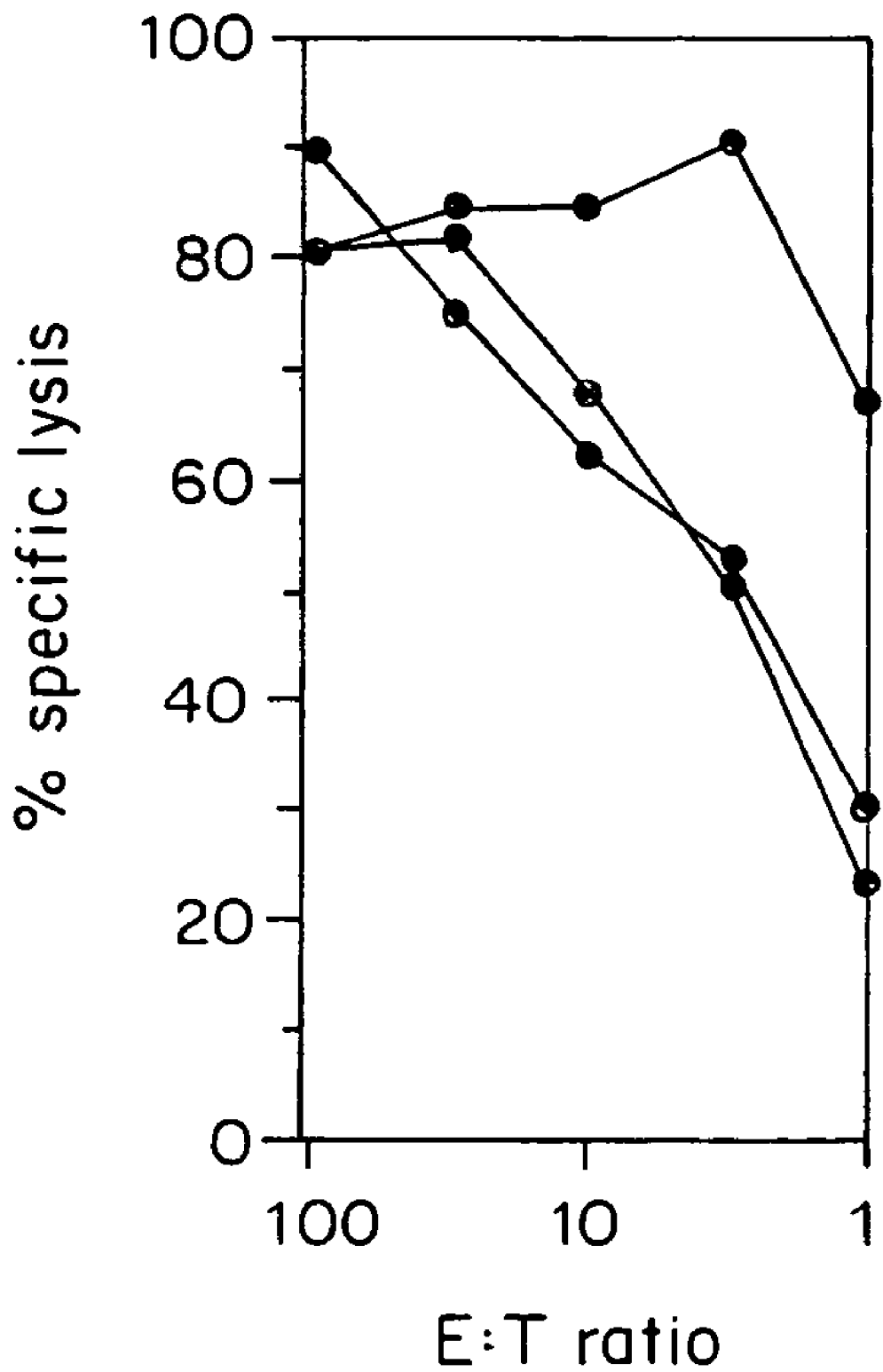

FIGS. 9A-9E show sporozoite-primed CTL responses are substantially boosted by MVA. Mice were immunised with two low doses (50+50) of irradiated sporozoites in FIG. 9A; two high doses (300+500) of sporozoites in FIG. 9B; mice were boosted with MVA.PbCSP following low-dose sporozoite priming in FIG. 9D; high dose sporozoite priming in FIG. 9E. CTL responses following immunisation with MVA.PbCSP are shown in FIG. 9C.

Recombinant Adenoviruses as Priming Agent

The prime-boost immunisation regimen has been exemplified using plasmid DNA and recombinant Ty-VLP as priming agent. Here an example using non-replicating adenoviruses as the priming agent is provided. Replication-deficient recombinant Adenovirus expressing E. coli β-Galactosidase (Adeno-GAL) was used. Groups of BALB/c mice were immunised with plasmid DNA followed by MVA or with Adenovirus followed by MVA. All antigen delivery systems used encoded E. coli β-galactosidase. Priming a CTL response with plasmid DNA or Adenovirus and boosting with MVA induces similar levels of CTL (FIGS. 10A-10B).

Figure 10A:
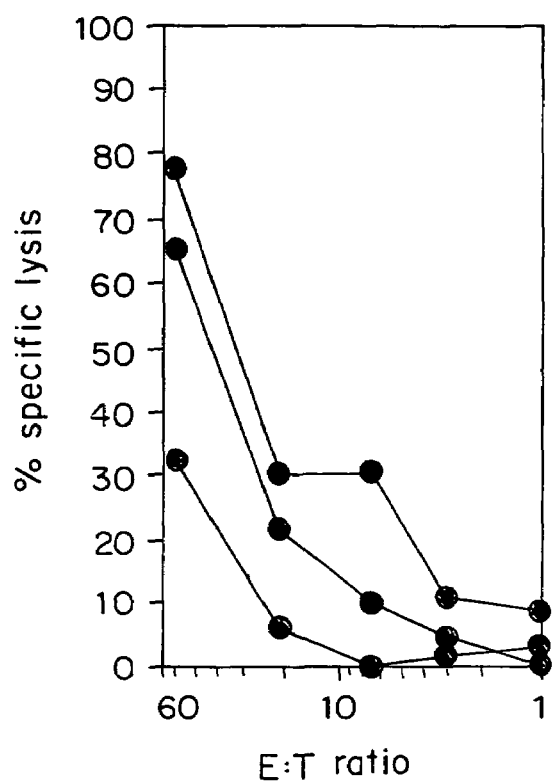
FIGS. 10A and 10B show CTL responses primed by plasmid DNA or recombinant Adenovirus and boosted with MVA. Groups of BALB/c mice (n=3) were primed with plasmid DNA(FIG. 10A) or recombinant Adenovirus expressing β-galactosidase (FIG. 10B). Plasmid DNA was administered intramuscularly, MVA intravenously and Adenovirus intradermally. Splenocytes were restimulated with peptide TPH-PARIGL [SEQ ID NO: 69] two weeks after the last immunisation. CTL activity was tested with peptide-pulsed P815 cells.
Figure 10B:
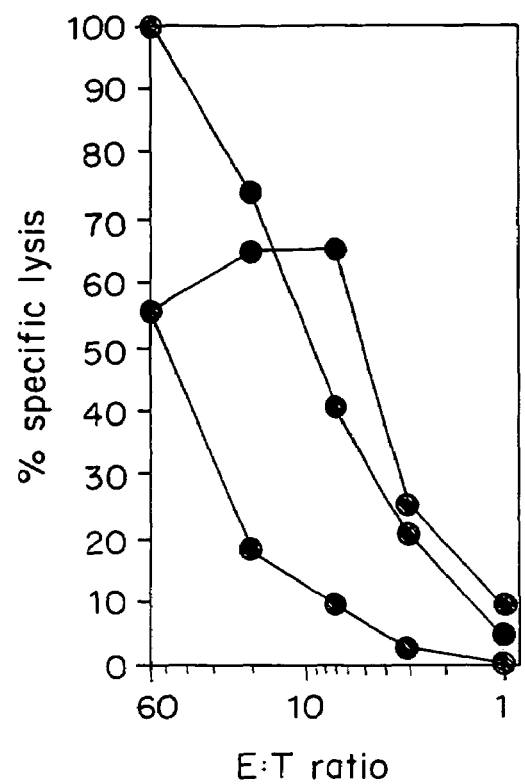

FIGS. 10A-10B show CTL responses primed by plasmid DNA or recombinant Adenovirus and boosted with MVA. Groups of BALB/c mice (n=3) were primed with plasmid DNA (FIG. 10A); or recombinant Adenovirus expressing β-Galactosidase (FIG. 10B). Plasmid DNA was administered intramuscularly, MVA intravenously and Adenovirus intradermally. Splenocytes were restimulated with peptide TPH-PARIGL [SEQ ID NO: 69] two weeks after the last immunisation. CTL activity was tested with peptide-pulsed P815 cells.

Immunogenicity of the DNA Prime Vaccinia Boost Regimen Depends on the Replication Competence of the Strain of Vaccinia Virus Used The prime boosting strategy was tested using different strains of recombinant vaccina viruses to determine whether the different strains with strains differing in their replication competence may differ in their ability to boost a DNA-primed CTL response. Boosting with replication-defective recombinant vaccinia viruses such as MVA and NYVAC resulted in the induction of stronger CTL responses compared to CTL responses following boosting with the same dose of replication competent WR vaccinia virus (FIGS. 11A-11C).

Figure 11C:
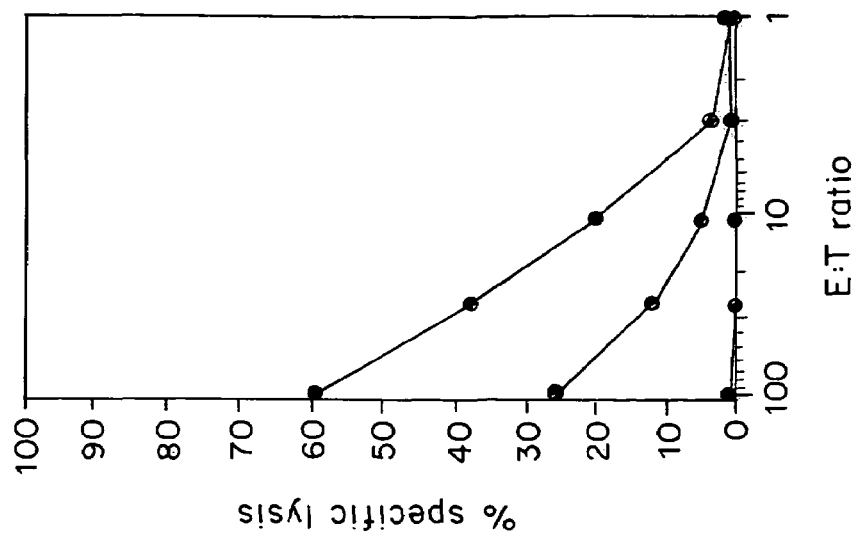
FIGS. 11A-11C show CTL responses in BALB/c mice primed with plasmid DNA followed by boosting with different recombinant vaccinia viruses. Animals were primed with pTH.PbCSP 50 μg/mouse i.m. and two weeks later boosted with different strains of recombinant vaccina viruses ($10^6$ pfu per mouse i.v.) expressing PbCSP. The different recombinant vaccinia virus strains were.
Figure 11B:
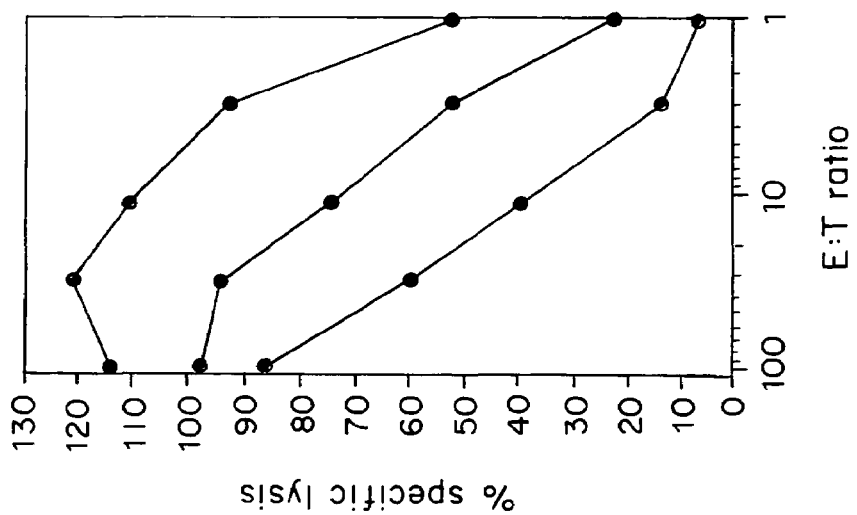
Figure 11A:
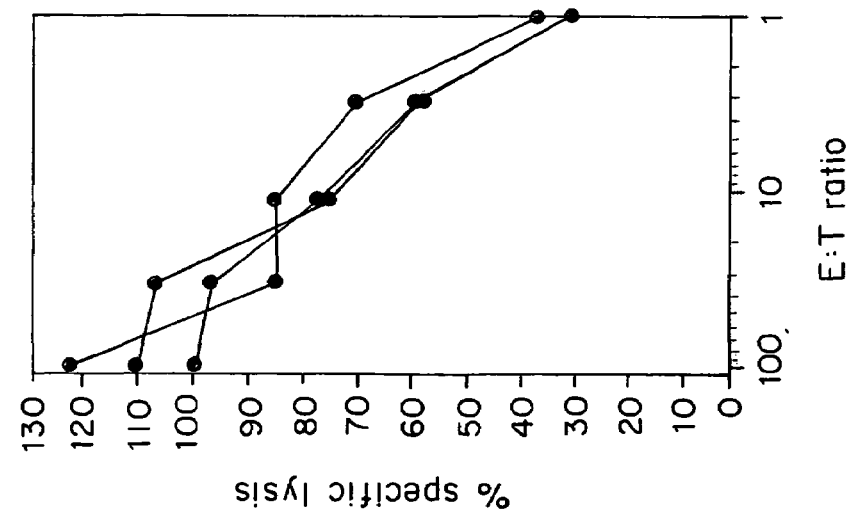

FIGS. 11A-11C show CTL responses in BALB/c mice primed with plasmid DNA followed by boosting with different recombinant vaccinia viruses. Animals were primed with pTH.PbCSP 50 µg/mouse i.m. and two weeks later boosted with different strains of recombinant vaccinia viruses ($10^6$ pfu per mouse i.v.) expressing PbCSP. The different recombinant vaccinia virus strains were MVA in FIG. 11A; NYVAC in FIG. 11B and WR in FIG. 11C. The superiority of replication-impaired vaccinia strains over replicating strains was found in a further experiment. Groups of BALB/c mice (n=6) were primed with 50 μg/animal of pSG2.PbCSP (i.m.) and 10 days later boosted i.v. with $10^6$ ffu/pfu of recombinant MVA, NYVAC and WR expressing PbCSP. The frequencies of peptide-specific CD8+ T cells were determined using the ELISPOT assay. The frequencies were: MVA 1103±438, NYVAC 826±249 and WR 468±135. Thus using both CTL assays and ELISPOT assays as a measure of CD8 T cell immunogenicity a surprising substantially greater immunogenicity of the replication-impaired vaccinia strains was observed compared to the replication competent strain.

The use of Recombinant Canary or Fowl Pox Viruses for Boosting Cd8+ T Cell Responses Recombinant canary pox virus (rCPV) or fowl pox virus (rFVP) are made using shuttle vectors described previously (Taylor et al. Virology 1992, 187: 321-328 and Taylor et al. Vaccine 1988, 6: 504-508). The strategy for these shuttle vectors is to insert the gene encoding the protein of interest preceded by a vaccinia-specific promoter between two flanking regions comprised of sequences derived from the CPV or FPV genome. These flanking sequences are chosen to avoid insertion into essential viral genes. Recombinant CPV or FPV are generated by in vivo recombination in permissive avian cell lines i.e. primary chicken embryo fibroblasts. Any protein sequence of antigens or epitope strings can be expressed using fowl pox or canary pox virus. Recombinant CPV or FPV is characterised for expression of the protein of interest using antigen-specific antibodies or including an antibody epitope into the recombinant gene. Recombinant viruses are grown on primary CEF. An immune response is primed using plasmid DNA as described in Materials and Methods. This plasmid DNA primed immune response is boosted using 10 ffu/pfu of rCPV or rFPV inoculated intravenously, intradermally or intramuscularly. CD8+ T cell responses are monitored and challenges are performed as described herein.

Example 3

Malaria Challenge Studies in Mice

To assess the protective efficacy of the induced levels of CD8+ T cell response immunised BALB/c or C57BL/6 mice were challenged by intravenous injection with 2000 or 200 *P. berghei* sporozoites. This leads to infection of liver cells by the sporozoites. However, in the presence of a sufficiently strong T lymphocyte response against the intrahepatic parasite no viable parasite will leave the liver and no blood-stage parasites will be detectable. Blood films from challenged mice were therefore assessed for parasites by microscopy 5-12 days following challenge.

BALB/c mice immunised twice with a mixture of two plasmid DNAs encoding the CS protein and the TRAP antigen, respectively, of *P. berghei* were not protected against sporozoite challenge. Mice immunised twice with a mixture of recombinant MVA viruses encoding the same two antigens were not protected against sporozoite challenge. Mice immunised first with the two recombinant MvAs and secondly with the two recombinant plasmids were also not protected against sporozoite challenge. However, all 15 mice immunised first with the two plasmid DNAs and secondly with the two recombinant MVA viruses were completely resistant to sporozoite challenge (Table 6 A and B).

To assess whether the observed protection was due to an immune response to the CS antigen or to TRAP or to both, groups of mice were then immunised with each antigen separately (Table 6 B). All 10 mice immunised first with the CS plasmid DNA and secondly with the CS MVA virus were completely protected against sporozoite challenge. Fourteen out of 16 mice immunised first with the TRAP plasmid DNA vaccine and secondly with the TRAP MVA virus were protected against sporozoite challenge. Therefore the CS antigen alone is fully protective when the above immunisation regime is employed and the TRAP antigen is substantially protective with the same regime.

The good correlation between the induced level of CD8+ T lymphocyte response and the degree of protection observed strongly suggests that the CD8+ response is responsible for the observed protection. In previous adoptive transfer experiments it has been demonstrated that CD8+ T lymphocyte clones against the major CD8+ T cell epitope in the *P. berghei* CS protein can protect against sporozoite challenge. To determine whether the induced protection was indeed mediated by CD8+ T cells to this epitope we then employed a plasmid DNA and a recombinant MVA encoding only this nine amino acid sequence from *P. berghei* as a part of a string of epitopes (Table 6 B). (All the other epitopes were from micro-organisms other than *P. berghei*). Immunisation of 10 mice first with a plasmid encoding such an epitope string and secondly with a recombinant MVA also encoding an epitope string with the *P. berghei* CTL epitope led to complete protection from sporozoite challenge (Table 6 B). Hence the induced protective immune response must be the CTL response that targets this nonamer peptide sequence.

TABLE 6

Results of Mouse Challenge Experiments Using Different Combinations of DNA and MVA Vaccine

| Immunisation 1 | Immunisation 2 | No. Infected/ No. challenged | % Protection |
|---|---|---|---|
| A. Antigens used: PbCSP + PbTRAP | | | |
| DNA | DNA | 5/5 | 0% |
| MVA | MVA | 9/10 | 10% |
| DNA | MVA | 0/5 | 100% |
| MVA | DNA | 5/5 | 0% |
| Control mice immunised with β-galactosidase | | | |
| DNA | DNA | 5/5 | 0% |
| MVA | MVA | 5/5 | 0% |
| DNA | MVA | 5/5 | 0% |
| MVA | DNA | 5/5 | 0% |
| B. | | | |
| DNA (CSP + TRAP) | MVA (CSP + TRAP) | 0/10 | 100% |
| DNA (CSP) | MVA (CSP) | 0/10 | 100% |
| DNA (TRAP) | MVA (TRAP) | 2/16 | 88% |
| DNA (epitope) | MVA (epitope) | 0/11 | 100% |
| DNA (beta-gal) | MVA (beta-gal) | 6/7 | 14% |
| none | none | 9/10 | 10% |

Table 6 Results of Two Challenge Experiments (A and B) Using Different Immunisation regimes of plasmid DNA and MVA as indicated. BALB/c mice were used in all cases. The immunisation doses were 50 μg of plasmid DNA or $10^6$ ffu of recombinant MVA. The interval between immunisations 1 and 2 was from 14-21 days in all cases. Challenges were performed at 18-29 days after the last immunisation by i.v. injection of 2000 *P. berghei* sporozoites and blood films assessed at 5, 8 and 10 days post challenge. CSP and TRAP indicate the entire *P. berghei* antigen and 'epitope' indicates the cassettes of epitopes shown in table 1 containing only a single *P. berghei* $K^d$-restricted nonamer CTL epitope. Note that in experiment B immunisation with the epitope string alone yields 100% protection.

Mice immunised twice with recombinant Ty-VLPs encoding pb9 were fully susceptible to infection. Similarly mice immunised twice with the recombinant MVA encoding the full CS protein were fully susceptible to infection. However, the mice immunised once with the Ty-VLP and subsequently once with the recombinant MVA showed an 85% reduction in malaria incidence when boosted with MVA expressing the full length CS protein, and 95% when MVA expressing the HM epitope string which includes pb9 was used to boost (Table 7).

TABLE 7

Results of Challenge Experiments Using Different Immunisation Regimes of Ty-VLPs and MVA

| Immunisation 1 | Immunisation 2 | No. Infected/ No. challenged | % Protection |
|---|---|---|---|
| Ty-CABDHFE | Ty-CABDHFE | 7/8 | 13% |
| Ty-CABDH | MVA.PbCSP | 2/13 | 85% |
| Ty-CABDHFE | MVA-NP | 5/5 | 0% |
| MVA.PbCSP | MVA.PbCSP | 6/6 | 0% |
| MVA.HM | Ty-CABDHFE | 14/14 | 0% |
| Ty-CABDHFE | MVA.HM | 1/21 | 95% |
| none | MVA.HM | 8/8 | 0% |
| none | none | 11/12 | 9% |

Table 7 Results of Challenge Experiments Using Different Immunisation Regimes of Ty-VLPs and MVA as Indicated. BALb/c Mice were used in all Cases.

Immunisations were of 50 μg of Ty-VLP or $10^7$ ffu of recombinant MVA administered intravenously. The interval between imrunisations 1 and 2 was from 14-21 days in all cases. Challenges were performed at 18-29 days after the last immunisation by i.v. injection of 2000 *P. berghei* sporozoites and blood films assessed at 5, 8 and 10 days post challenge. CSP indicates the entire *P. berghei* antigen. Ty-VLPs carried epitope cassettes CABDH or CABDHFE as described in table 1. MVA.HM includes cassettes CAB.

To determine whether the enhanced immunogenicity and protective efficacy observed by boosting with a recombinant MVA is unique to this particular vaccinia virus strain or is shared by other recombinant vaccinias the following experiment was performed. Mice were immunised with the DNA vaccine encoding *P. berghei* CS protein and boosted with either (i) recombinant MVA encoding this antigen; (ii) recombinant wild-type vaccinia virus (Western Reserve strain) encoding the same antigen (Satchidanandam et al. 1991), or (iii) recombinant NYVAC (COPAK) virus (Lanar et al. 1996) encoding the same malaria antigen. The highest degree of protection was observed with boosting by the MVA recombinant, 80% (Table 8). A very low level of protection (10%) was observed by boosting with the wild-type recombinant vaccinia virus and a significant level of protection, 60%, by boosting with the NYVAC recombinant. Hence the prime-boost regime we describe induces protective efficacy with any non-replicating vaccinia virus strain. Both the MVA recombinant and NYVAC were significantly (P<0.05 for each) better than the WR strain recombinant.

TABLE 8

Challenge Data Results for DNA Boosted with Various Vaccinia Strain Recombinants.

| Immunisation 1 | Immunisation 2 | No. Infected/ No. challenged | % Protection |
|---|---|---|---|
| DNA-beta gal. | MVA.NP | 8/8 | 0% |
| DNA-CSP | MVA-CSP | 2/10 | 80% |
| DNA-CSP | WR-CSP | 9/10 | 10% |
| DNA-CSP | NYVAC-CSP | 4/10 | 60% |

Table 8 Results of a challenge experiment using different immunisation regimes of plasmid DNA and various vaccinia recombinants as indicated. BALB/c mice were used in all cases. The immunisation doses were 50 μg of plasmid DNA or $10^6$ ffu/pfu of recombinant MVA or $10^4$ ffu/pfu of recombinant wild type (WR) vaccinia or $10^6$ ffu/pfu of recombinant NYVAC. Because the WR strain will replicate in the host and the other strains will not, in this experiment a lower dose of WR was used. The interval between immunisations 1 and 2 was 23 days. Challenges were performed at 28 days after the last immunisation by i.v. injection of 2000 *P. berghei* sporozoites and blood films assessed at 7, 9 and 11 days post challenge. pbCSP indicates the entire *P. berghei* antigen and NP the nucleoprotein antigen of influenza virus (used as a control antigen). The first immunisation of group A mice was with the plasmid DNA vector expressing beta galactosidase but no malaria antigen.

In a further experiment shown in Table 8, mice were immunised with the DNA vaccine encoding *P. berghei* CS protein and boosted with either (i) recombinant MVA encoding this antigen; (ii) recombinant WR vaccinia virus encoding the same antigen or (iii) recombinant NYVAC (COPAK) virus encoding the same malaria antigen, all at $10^6$ ffu/pfu. A high and statistically significant degree of protection was observed with boosting with recombinant NYVAC (80%) or recombinant MVA (66%). A low and non-significant level of protection (26%) was observed by boosting with the WR recombinant vaccinia virus (Table 9). MVA and NYVAC boosting each gave significantly more protection than WR boosting (P=0.03 and P=0.001 respectively). These data reemphasise that non-replicating pox virus strains are better boosting agents for inducing high levels of protection.

TABLE 9

Influence of Different Recombinant Vaccinia Strains on Protection.

| Immunisation 1 DNA | Immunisation 2 | No. inf./ No. chall. | % protection |
|---|---|---|---|
| CSP | MVA.PbCSP | 5/15 | 66 |
| CSP | NYVAC.PbCSP | 2/15 | 80 |
| CSP | WR.PbCSP | 11/15 | 26 |
| β-galactosidase | MVA.NP | 8/8 | 0 |

Table 9 Results of challenge experiments using different immunisation regimes of plasmid DNA and replication incompetent vaccinia recombinants as boosting immunisation. BALB/c mice were used in all cases. The immunisation doses were 50 μg of plasmid DNA or $10^6$ ffu/pfu of recombinant MVA or recombinant wild type (WR) vaccinia or recombinant NYVAC. The interval between immunisations 1 and 2 was 23 days. Challenges were performed at 28 days after the last immunisation by i.v. injection of 2000 *P. berghei* sporozoites and blood films assessed at 7, 9 and 11 days post challenge. PbCSP indicates the entire *P. berghei* antigen and NP the nucleoprotein antigen of influenza virus (used as a control antigen). The control immunisation was with a plasmid DNA vector expressing β-Galactosidase followed by MVA.NP.

Alternative Routes for Boosting Immune Responses with Recombinant MVA

Intravenous injection of recombinant MVA is not a preferred route for immunising humans and not feasible in mass immunisations. Therefore different routes of MVA boosting were tested for their immunogenicity and protective efficacy.

Mice were primed with plasmid DNA i.m. Two weeks later they were boosted with MVA administered via the following routes: intravenous (i.v.), subcutaneous (s.c.), intraperitoneal (i.p.), intramuscular (i.p.) and intradermal (i.d.). Two weeks after this boost peptide-specific CD8+ T cells were determined in an ELISPOT assay. The most effective route which induced the highest levels were i.v. and i.d inoculation of MVA. The other routes gave moderate to poor responses (FIG. 12).

Figure 12:
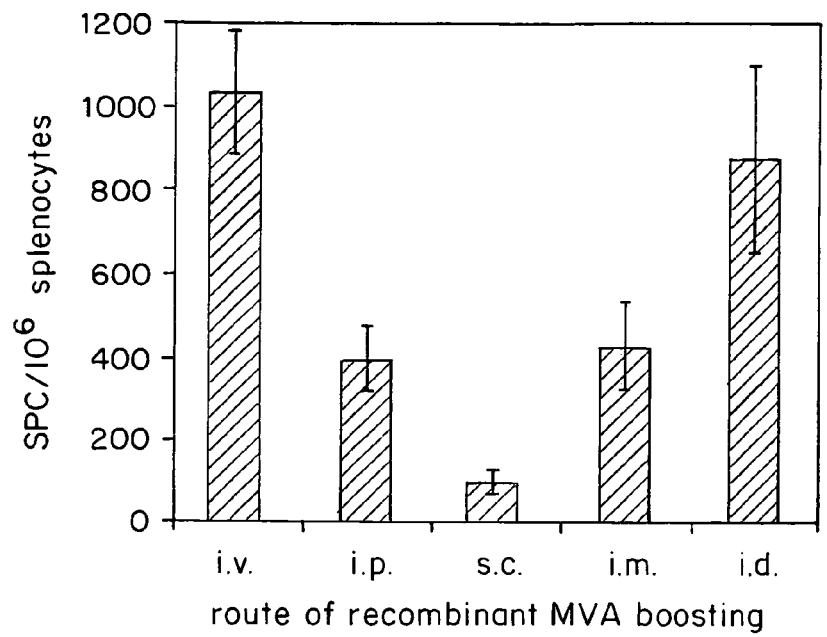
FIG. 12 shows frequencies of peptide-specific CD8+ T cells following different routes of MVA boosting. Results are shown as the number of spot-forming cells (SFC) per one million splenocytes. Each bar represents the mean number of SFCs from three mice assayed individually.

FIG. 12 shows frequencies of peptide-specific CD8+ T cells following different routes of MVA boosting. Results are shown as the number of spot-forming cells (SFC) per one million splenocytes. Mice were primed with plasmid DNA and two weeks later boosted with MVA via the indicated routes. The number of splenocytes specific for the SYIP-SAEKI [SEQ ID NO: 67] peptide was determined in INF-γ ELISPOT assays two weeks after the last immunisation. Each bar represents the mean number of SFCs from three mice assayed individually.

Boosting via the i.v. route was compared with the i.d. and i.m route in a challenge experiment. The i.d route gave high levels of protection (80% protection). In the group of animals that were boosted via the i.m. route, 50% of the animals were protected. Complete protection was achieved with MVA boost administered i.v. (Table 10)

TABLE 10

Influence of the Route of MVA Administration on Protective Efficacy

| Immunisation 1 DNA | Immunisation 2 MVA | No. infected/ No. challenged | % protection |
|---|---|---|---|
| CSP | CSP i.v. | *0/20 | 100 |
| CSP | CSP i.d | 2/10 | 80 |
| CSP | CSP i.m. | 5/10 | 50 |
| Epitope | epitope i.v. | 1/10 | 90 |
| NP | NP i.v. | 10/10 | 0 |

*culminative data from two independent experiments

Table 10 Results from challenge experiments using different routes of MVA boosting immunisation. Animals were primed by intramuscular plasmid DNA injection and two weeks later boosted with the indicated recombinant MVA ($10^6$ ffu/mouse) administered via the routes indicated. The mice were challenged 16 days after the last immunisation with 2000 *P. berghei* sporozoites and screened for blood stage parasitemia at day 8 and 10 post challenge. Epitope indicates the polypeptide string HM.

Alternative Routes of DNA Priming: The use of a Gene Gun to Prime Peptide Specific Cd8+ T Cells Gene gun delivery is described in detail in for example in Eisenbraun et al. DNA Cell Biol. 1993, 12: 791-797 and Degano et al. Vaccine 1998, 16: 394-398.

The mouse malaria challenge experiments described so far using plasmid DNA to prime an immune response used intramuscular injection of plasmid DNA. Intradermal delivery of plasmid DNA using a biolistic device is another route to prime specific CTL responses. Plasmid DNA is coated onto gold particles and delivered intradermally with a gene gun. Groups of mice (n=10) were immunised three times at two weeks intervals with the gene gun alone (4 µg/immunisation), immunised two times with the gene gun followed by an intravenous MVA.PbCSP boost or immunised intramuscularly with 50 µg of pTH.PbCSP and two weeks later boosted with MVA.PbCSP intravenously. Two weeks after the last immunisation the animals were challenged with 2000 sporozoites to assess protective efficacy of each immunisation regimen. In the group that received the intravenous MVA boost following two gene gun immunisations one out of ten animals developed blood stage parasitemia (90% protection). Complete protection was observed with intramuscular DNA priming followed by MVA i.v boosting. Seven out of 10 animals that were immunised three times with the gene gun were infected. (30% protection) (Table 11).

TABLE 11

Results of challenge experiments comparing different routes of DNA priming (intradermally by gene gun versus intramuscular needle injection). Groups of BALB/c mice (n = 10) were immunised as indicated. Each gene gun immunisation delivered 4 µg of plasmid DNA intraepidermally. For i.m. inimunisations 50 mg of plasmid DNA were injected. Twenty days after the last immunisation mice were challenged as described previously.

| Immunisation 1 DNA | Immunisation 2 | Immunisation 3 | No. inf./ No. chall. | % protection |
|---|---|---|---|---|
| gene gun DNA | gene gun DNA | gene gun DNA | 7/10 | 30 |
| gene gun DNA | gene gun DNA | MVA.PbCSP | 1/10 | 90 |
| — | DNA i.m | MVA.PbCSP | 0/10 | 100 |
| Naïve | | | 10/10 | 0 |

Highly Susceptible C57BL/6 Mice are Protected

C57BL/6 mice are very susceptible to *P. berghei* sporozoite challenge. C57BL/6 mice were immunised using the DNA-MVA prime boost regime with both pre-erythrocytic antigens PbCSP and PbTRAP, and challenged with either 200 or 1000 infectious sporozoites per mouse. (Two hundred sporozoites corresponds to more than twice the dose required to induce infection in this strain). All ten mice challenged with 200 sporozoites showed sterile immunity. Even the group challenged with 1000 sporozoites, 60% of the mice were protected (Table 12). All the naive C57BL/6 mice were infected after challenge.

TABLE 12

Protection of C57BL/6 Mice from Sporozoite Challenge

| | No. animals inf./ No. challenged | % protection |
|---|---|---|
| 1000 sporozoites | | |
| DNA followed by MVA | 4/10 | 60 |
| Naïve | 5/5 | 0 |

TABLE 12-continued

Protection of C57BL/6 Mice from Sporozoite Challenge

| | No. animals inf./ No. challenged | % protection |
|---|---|---|
| 200 sporozoites | | |
| DNA followed by MVA | 0/10 | 100 |
| Naïve | 5/5 | 0 |

Table 12 Results of a challenge experiment using C57BL/6 mice. Animals were immunised with PbCSP and PbTRAP using the DNA followed by MVA prime boost regime. Fourteen days later the mice were challenged with *P. berghei* sporozoites as indicated.

Example 4

Protective Efficacy of the DNA-priming/MVA-Boosting Regimen in Two Further Disease Models in Mice Following immunogenicity studies, the protective efficacy of the DNA-priming MVA-boosting regimen was tested in two additional murine challenge models. The two challenge models were the P815 tumour model and the influenza A virus challenge model. In both model systems CTL have been shown to mediate protection.

P815 Tumour Challenges:

Groups (n=10) of DBA/2 mice were immunised with a combination of DNA followed by MVA expressing a tumour epitope string or the HM epitope string. Two weeks after the last immunisation the mice were challenged intravenously with $10^5$ P815 cells. Following this challenge the mice were monitored regularly for the development of tumour-related signs and survival.

Figure 13:
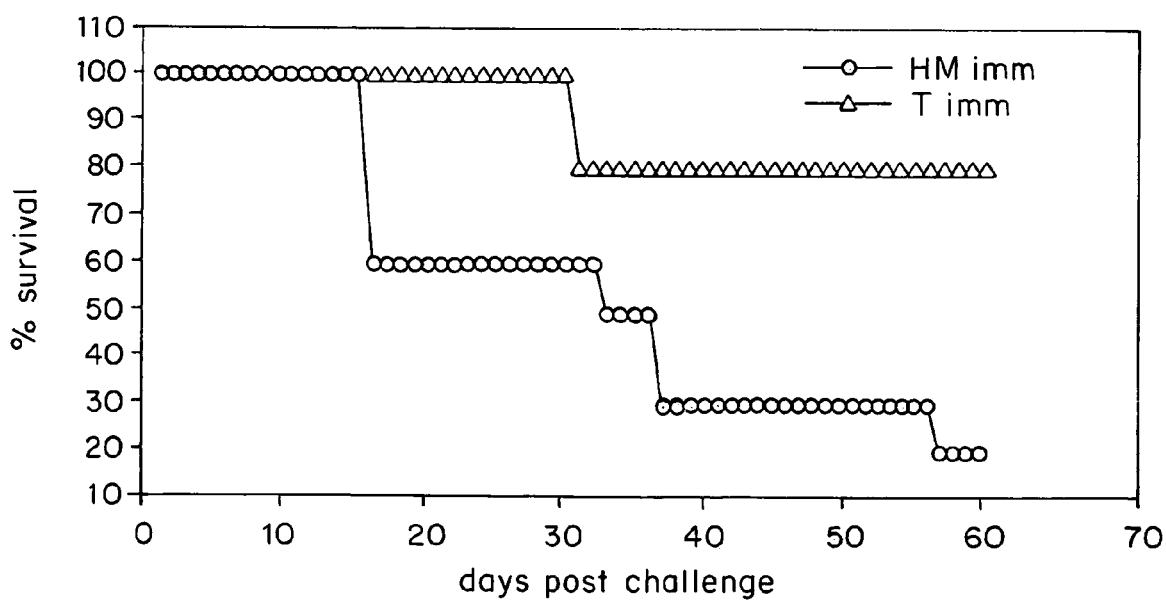
FIG. 13 shows the survival rate of the two groups of mice. Sixty days after challenge eight out of ten mice were alive in the group immunised with the tumour epitopes string.

FIG. 13 shows the survival rate of the two groups of mice. Sixty days after challenge eight out of ten mice were alive in the group immunised with the tumour epitopes string. In the group immunised with the HM epitope string only 2 animals survived. This result is statistically significant: 2/10 vs 8/10 chi-squared=7.2. P=0.007. The onset of death in the groups of animals immunised with the tumour epitope string is delayed compared to the groups immunised with the HM epitope string.

Influenza Virus Challenges:

Groups of BALB/c mice were immunised with three gene gun immunisations with plasmid DNA, two intramuscular plasmid DNA injections, one i.m. DNA injection followed by one MVA.NP boost i.v. or two gene gun immunisations followed by one MVA.NP boost i.v. Plasmid DNA and recombinant MVA expressed the influenza virus nucleoprotein. Two weeks after the last immunisation the mice were challenged intranasally with 100 HA of influenza A/PR/8/34 virus. The animals were monitored for survival daily after challenge.

Complete protection was observed in the following groups of animals:
two DNA gene gun immunisations followed by one MVA.NP boost i.v.;
one i.m. DNA injection followed by one MVA.NP boost i.v.; and
two i.m. DNA injections.

In the group of animals immunised three times with the gene gun 71% of the animals survived (5/7) and this difference from the control group was not significant statistically (P>0.05). In the naive group 25% of the animals survived (FIG. 14) and this group differed significantly (P<0.05) for the two completely protected groups.

Figure 14:
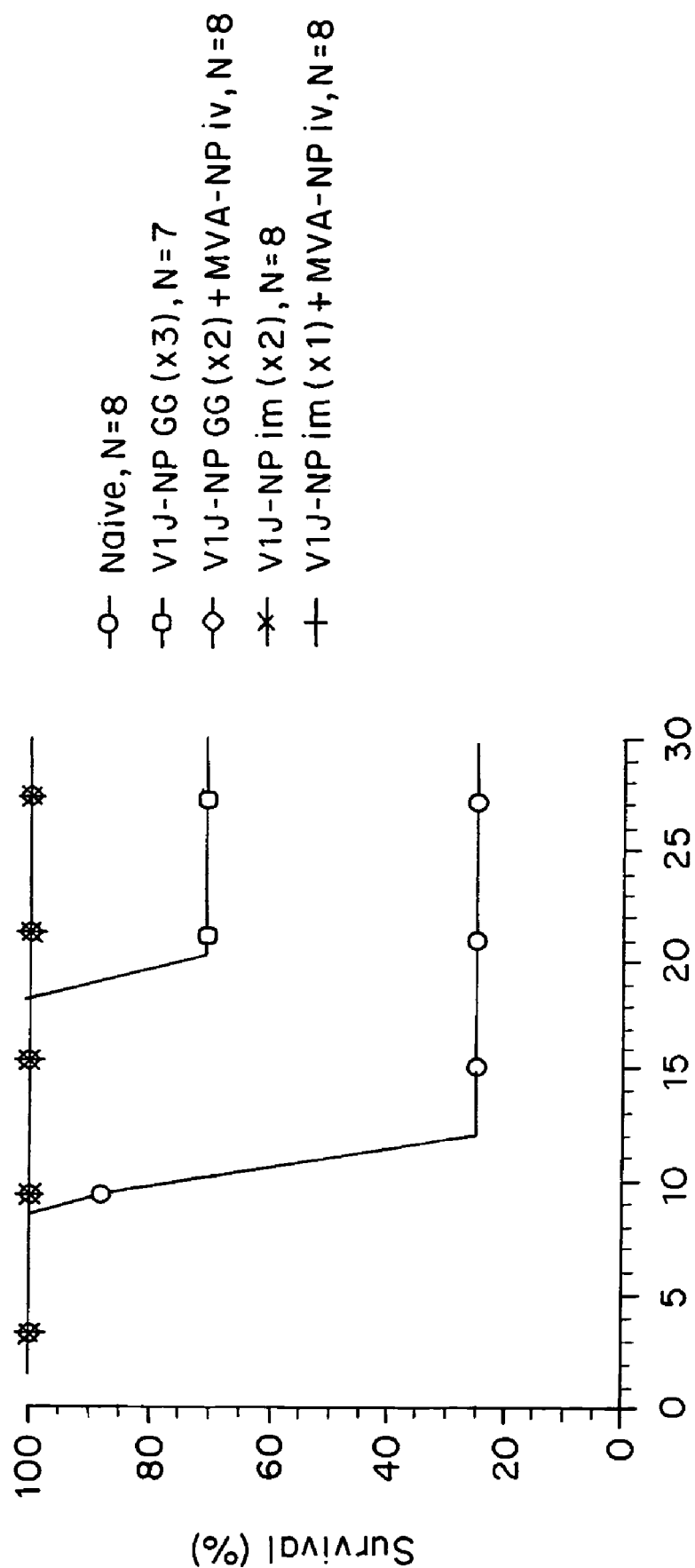
FIG. 14 shows results of an influenza virus challenge experiment. BALB/c mice were immunised as indicated. GG=gene gun immunisations, im=intramuscular injection, iv=intravenous injection. Survival of the animals was monitored daily after challenge.

FIG. 14 shows results of an influenza virus challenge experiment. BALB/c mice were immunised as indicated. GG=gene gun immunisations, im=intramuscular injection, iv=intravenous injection. Survival of the animals was monitored daily after challenge. In a second experiment groups of 10 BALB/c mice were immunised with MVA.NP i.v. alone, three times with the gene gun, two times with the gene gun followed by one MVA.NP boost i.v. and two i.m injections of V1J-NP followed by one MVA.NP boost. Two weeks after the last immunisation the mice were challenged with 100 HA units of influenza A/PR/8/34 virus.

Complete and statistically significant protection was observed in the following groups of animals:
two gene gun immunisations followed by one MVA.NP boost; and
two i.m injections of V1J-NP followed by one MVA.NP boost. In the group receiving one MVA.NP i.v., 30% (3 out of 10) of animals survived. In the group immunised with a DNA vaccine delivered by the gene gun three times, 70% of the animals were protected but this protection was not significantly different from the naive controls. In this challenge experiment 40% (4 out of 10) of the naive animals survived the challenge.

Example 5

Immunogenicity Studies in Non-human Primates

Immunogenicity and Protective Efficacy of the Prime Boost Regimen in Non-Human Primates.

In order to show that the strong immunogenicity of the DNA priming/MVA boosting regime observed in mice translates into strong immunogenicity in primates, the regimen was tested in macaques. The vaccine consisted of a string of CTL epitopes derived from HIV and SIV sequences (FIG. 2), in plasmid DNA or MVA, denoted DNA.H and MVA.H respectively. The use of defined CTL epitopes in a polyepitope string allows testing for SIV specific CTL in macaques. Due to the MHC class I restriction of the antigenic peptides, macaques were screened for their MHC class I haplotype and Mamu-A*01-positive animals were selected for the experiments described.

Three animals (CYD, DI and DORIS) were immunised following this immunisation regimen:

| week 0 | DNA (8 μg, i.d., gene gun) |
|---|---|
| week 8 | DNA (8 μg, i.d., gene gun) |
| week 17 | MVA (5 × $10^8$ pfu, i.d.) |
| week 22 | MVA (5 × $10^8$ pfu, i.d.) |

Blood from each animal was drawn at weeks 0, 2, 5, 8, 10, 11, 17, 18, 19, 21, 22, 23, 24 and 25 of the experiment. The animals were monitored for induction of CTL using two different methods. PBMC isolated from each bleed were re-stimulated in vitro with a peptide encoded in the epitope string and tested for their ability to recognise autologous peptide-loaded target cells in a chromium release cytotoxicity assay. Additionally, freshly isolated PBMC were stained for antigen specific CD8+ T cells using tetramers.

Figure 15A:
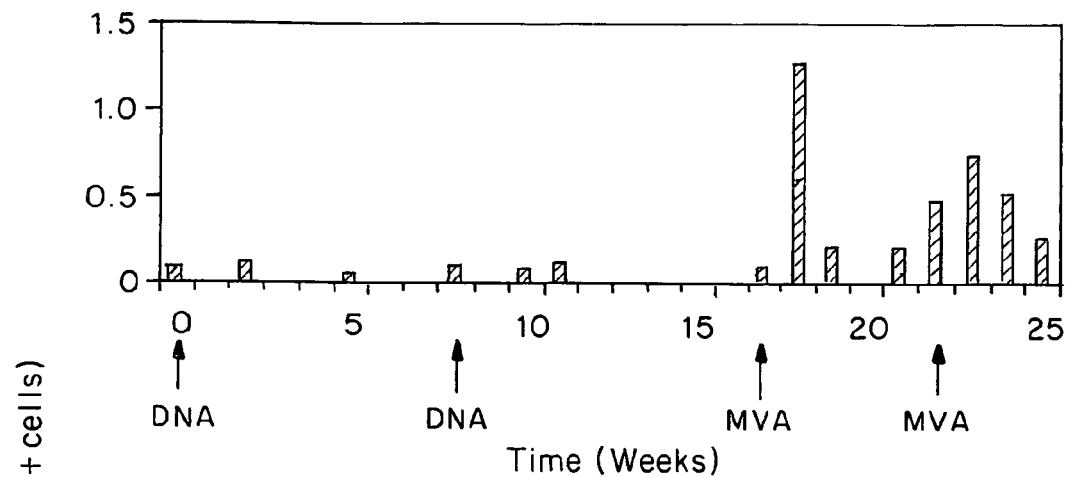
FIGS. 15A-15C show detection of SIV-specific MHC class I-restricted CD8+ T cells using tetramers. Each bar represents the percentage of CD8+ T cells specific for the Mamu-A*01/gag epitope at the indicated time point. One percent of CD8 T cells corresponds to about $5000/10^6$ peripheral blood lymphocytes.
Figure 15B:
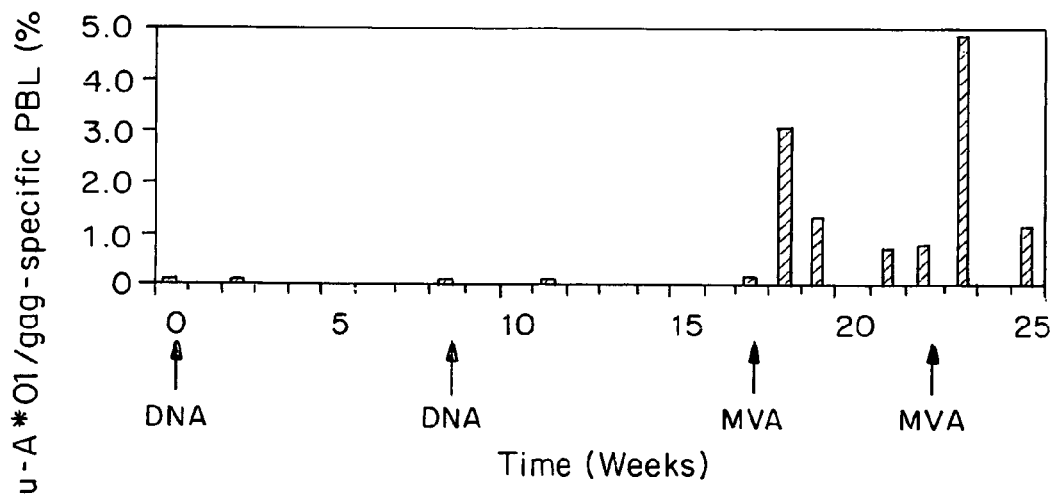
Figure 15C:
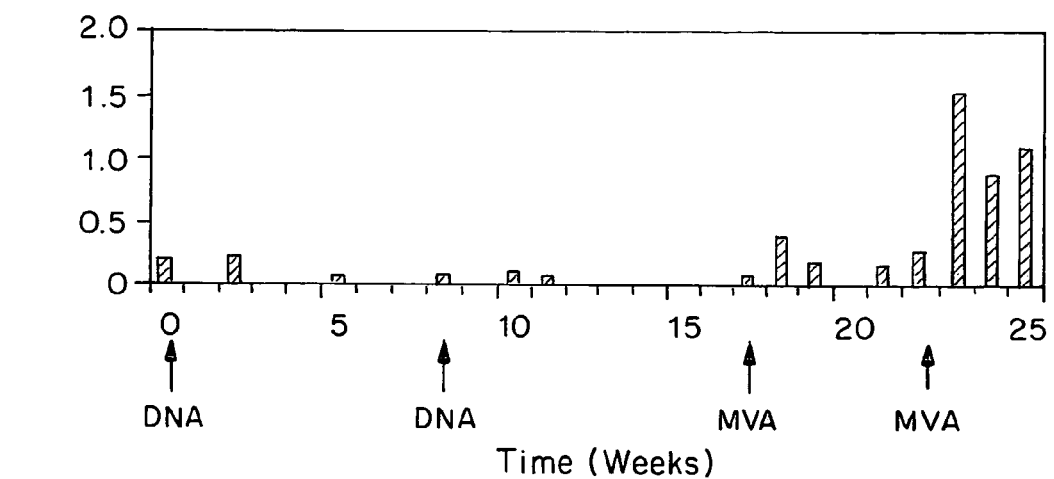

Following two gene gun immunisations very low levels of CTL were detected using tetramer staining (FIGS. 15A-15C).

Two weeks after the first MVA boosting, all three animals developed peptide specific CTL as detected by tetramer staining (FIGS. 15A-15C). This was reflected by the detection of moderate CTL responses following in vitro restimulation (FIG. 16B, week 19). The second boost with MVA.H induced very high levels of CD8+, antigen specific T cells (FIGS. 15A-15C) and also very high levels of peptide specific cytotoxic T cells (FIG. 16C, week 23).

FIGS. 15A-15C show detection of SIV-specific MHC class I-restricted CD8+ T cells using tetramers. Three Mamu-A*A01-positive macaques were immunised with plasmid DNA (gene gun) followed by MVA boosting as indicated. Frequencies of Mamu-A*A01/CD8 double-positive T cells were identified following FACS analysis. Each bar represents the percentage of CD8+ T cells specific for the Mamu-A*01/gag epitope at the indicated time point. One percent of CD8 T cells corresponds to about 5000/10$^6$ peripheral blood lymphocytes. Thus the levels of epitope-specific CD8 T cells in the peripheral blood of these macaques are at least as high as the levels obvserved in the spleens of immunised and protected mice in the malaria studies.

Figure 16A:
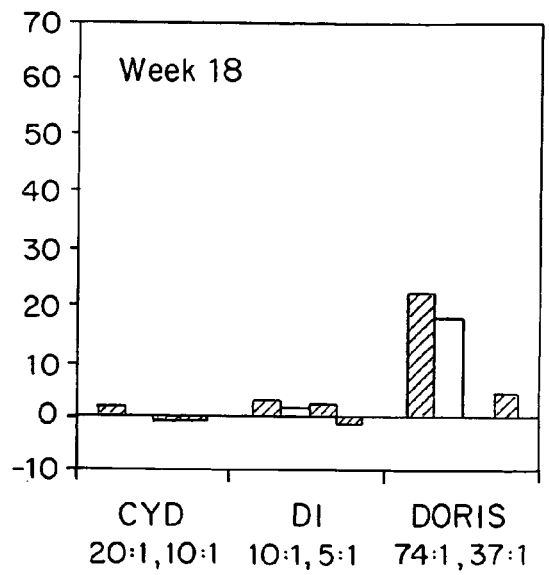
FIGS. 16A-16C show CTL induction in macaques following DNA/MVA immunisation. PBMC from three different macaques (CYD, DI and DORIS) were isolated at week 18, 19 and 23 and were restimulated with peptide CTPYDINQM [SEQ ID NO: 54] in vitro. After two restimulations with peptide CTPYDINQM [SEQ ID NO: 54] the cultures were tested for their lytic activity on peptide-pulsed autologous target cells.
Figure 16B:
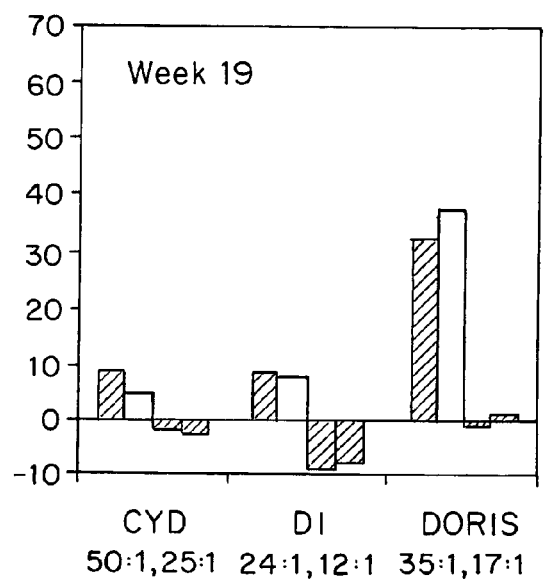
Figure 16C:
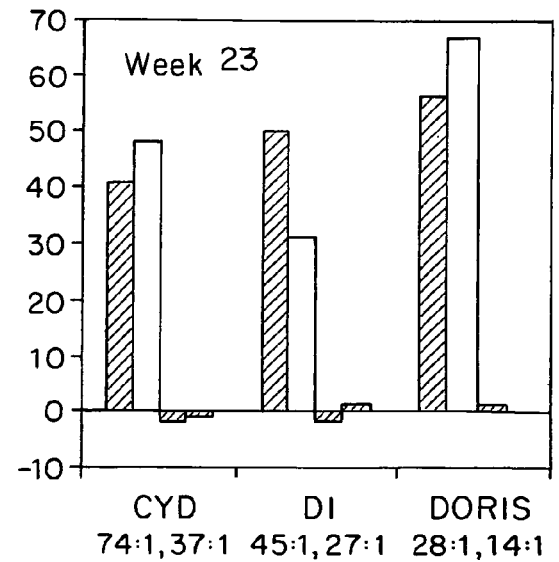

FIGS. 16A-16C shows CTL induction in macaques following DNA/MVA immunisation. PBMC from three different macaques (CYD, DI and DORIS) were isolated at week 18, 19 and 23 and were restimulated with peptide CTPYDINQM [SEQ ID NO: 54] in vitro. After two restjmulations with peptide CTPYDINQM [SEQ ID NO: 54] the cultures were tested for their lytic activity on peptide-pulsed autologous target cells. Strong CTL activity was observed.

Example 6

Immunogenicity and Challenge Studies in Chimpanzees

To show that a similar regime of initial immunisation with plasmid DNA and subsequent immunisation with recombinant MVA can be effective against *Plasmodium falciparum* malaria in higher primates an immunisation and challenge study was performed with two chimpanzees. Chimp H1 received an initial immunisation with 500 μg of a plasmid expressing *Plasmodium falciparum* TRAP from the CMV promoter without intron A, CMV-TRAP. Chimp H2 received the same dose of CMV-LSA-1, which expresses the C-terminal portion of the LSA-1 gene of *P. falciparum*. Both chimps received three more immunisations over the next 2 months, but with three plasmids at each immunisation. H1 received CMV-TRAP as before, plus pTH-TRAP, which expresses TRAP using the CMV promoter with intron A, leading to a higher expression level. H1 also received RSV-LSA-1, which expresses the C-terminal portion of LSA-1 from the RSV promoter. H2 received CMV-LSA-1, pTH-LSA-1 and RSV-TRAP at the second, third and fourth immunisations. The dose was always 500 μg of each plasmid.

It was subsequently discovered that the RSV plasmids did not express the antigens contained within them, so H1 was only immunised with plasmids expressing TRAP, and H2 with plasmids expressing LSA-1.

Between and following these DNA immunisations assays of cellular immune responses were performed at several time points, the last assay being performed at three months following the fourth DNA immunisation, but no malaria-specific T cells were detectable in either ELISPOT assays or CTL assays for CD8+ T cells.

Both animals were subsequently immunised with three doses of 10$^8$ ffu of a recombinant MVA virus encoding the *P. falciparum* TRAP antigen over a 6 week period. Just before and also following the third recombinant MVA immunisation T cell responses to the TRAP antigen were detectable in both chimpanzees using an ELISPOT assay to whole TRAP protein bound to latex beads. This assay detects both CD4+ and CD8+ T cell responses. Specific CD8+ T responses were searched for with a series of short 8-11 amino acid peptides in both immunised chimpanzees. Such analysis for CD8+ T cell responses indicated that CD8+ T cells were detectable only in the chimpanzee H1. The target epitope of these CD8+ T lymphocytes was an 11 amino acid peptide from TRAP, tr57, of sequence KTASCGVWDEW [SEQ ID NO: 78]. These CD8+ T cells from H1 had lytic activity against autologous target cells pulsed with the tr57 peptide and against autologous target cells infected with the recombinant PfTRAP-MVA virus. A high precursor frequency of these specific CD8+ T cells of about 1 per 500 lymphocytes was detected in the peripheral blood of this chimpanzee H1 using an ELISPOT assay two months following the final MVA immunisation. No specific CD8+ T cell response was clearly detected in the chimpanzee H2, which was not primed with a plasmid DNA expressing TRAP.

Two months after the third PfTRAP-MVA immunisation challenge of H1 and H2 was performed with 20,000 sporozoites, a number that has previously been found to yield reliably detectable blood stage infection in chimpanzees 7 days after challenge (Thomas et al. 1994 and unpublished data). The challenge was performed with the NF54 strain of *Plasmodium falciparum*. This is of importance because the TRAP sequence in the plasmid DNA and in the recombinant MVA is from the T9/96 strain of *P. falciparum* which has numerous amino acid differences to the NF54 TRAP allele (Robson et al. 1990). Thus, this sporozoite challenge was performed with a heterologous rather than homologous strain of parasite. In the chimpanzee H2 parasites were detectable in peripheral blood as expected 7 days after sporozoite challenge using in vitro parasite culture detection. However, in H1 the appearance of blood stage parasites in culture from the day 7 blood samples was delayed by three days consistent with some immune protective effect against the liver-stage infection. In studies of previous candidate malaria vaccines in humans a delay in the appearance of parasites in the peripheral blood has been estimated to correspond to a substantial reduction in parasite density in the liver (Davis et al. 1989). Thus the chimpanzee H1, immunised first with *P. falciparum* TRAP plasmid DNA and subsequently with the same antigen expressed by a recombinant MVA virus showed a strong CD8+ T lymphocyte response and evidence of some protection from heterologous sporozoite challenge.

Discussion

These examples demonstrate a novel regime for immunisation against malaria which induces high levels of protective CD8+ T cells in rodent models of human malaria infection. Also demonstrated is an unprecedented complete protection against sporozoite challenge using subunit vaccines (36 out of 36 mice protected in Table 6 using DNA priming and MVA boosting with the CS epitope containing vaccines). Induction of protective immune responses using the DNA priming/MVA boosting regimen was demonstrated in two additional mouse models of viral infection influenza A model and cancer (P815 tumour model). More importantly for vaccines for use in humans this immunisation regimen is also highly immunogenic for CD8+ T cells in primates. Strong SIV-gag-specific CTL were induced in 3 out of 3 macaques with plasmid DNA and MVA expressing epitope strings. The levels induced are comparable to those found in SWV-infected animals. The data from the chimpanzee studies indicate that the same immunisation regime can induce a strong CD8+ T lymphocyte response against *P. falciparum* in higher primates with some evidence of protection against *P. falciparum* sporozoite challenge.

Ty-VLPs have previously been reported to induce good levels of CD8+ T cell responses against the *P. berghei* rodent malaria (Allsopp et al. 1995) but alone this construct is not protective. It has now been found that subsequent immunisation with recombinant MVA boosts the CD8+ T cell response very substantially and generates a high level of protection (Table 7).

Recombinant MVA viruses have not been assessed for efficacy as malaria vaccines previously. Recombinant MVA alone was not significantly protective, nor was priming with recombinant MVA followed by a second immunisation with recombinant plasmid DNA. However, a second immunisation with the recombinant MVA following an initial immunisation with either Ty-VLPs or plasmid DNA yielded impressive levels of protection. Non-recombinant MVA virus has been safely used to vaccinate thousands of human against smallpox and appears to have an excellent safety profile. The molecular basis of the increased safety and immunogenicity of this strain of vaccinia virus is being elucidated by detailed molecular studies (Meyer et al. 1991; Sutter at al. 1994).

Plasmid DNA has previously been tested as a malaria vaccine for the *P. yoelii* rodent malaria. High levels of, but not complete, protection is seen in some strains but in other strains of mice little or no protection was observed even after multiple immunisations (Doolan et al. 1996). Although plasmid DNA has been proposed as a method of immunisation against *P. falciparum*, success has not previously been achieved. The evidence provided here is the first evidence to show that plasmid DNA may be used in an immunisation regime to induce protective immunity against the human malaria parasite *P. falciparum*.

A similar regime of immunisation to the regime demonstrated herein can be expected to induce useful protective immunity against *P. falciparum* in humans. It should be noted that five of the vaccine constructs employed in these studies to induce protective immunity in rodents or chimpanzees contain *P. falciparum* sequences and could therefore be used for human immunisation against *P. falciparum*. These are: 1. The *P. falciparum* TRAP plasmid DNA vaccine. 2. The *P. falciparum* TRAP recombinant MVA virus. 3. The Ty-VLP encoding an epitope string of numerous *P falciparum* epitopes, as well as the single *P. berghei* CTL epitope. 4. The plasmid DNA encoding the same epitope string as 3. 5. The recombinant MVA encoding the longer HM epitope string including many of the malaria epitopes in 3 and 4. Similarly the plasmid DNAs and MVA encoding HIV epitopes for human class I molecules could be used in either prophylactic or therapeutic immunisation against HIV infection.

These studies have provided clear evidence that a novel sequential immunisation regime employing a non-replicating or replication-impaired pox virus as a boost is capable of inducing a strong protective CD8+ T cell response against the malaria parasite. The examples demonstrate clearly a surprising and substantial enhancement of CD8+ T cell responses and protection compared to replicating strains of pox viruses. Because there is no reason to believe that the immunogenicity of CD8+ T cell epitopes from the malaria parasite should differ substantially from CD8+ T cell epitopes in other antigens it is expected that the immunisation regime described herein will prove effective at generating CD8+ T cell responses of value against other diseases. The critical step in this immunisation regimen is the use of non-replicating or replication-impaired recombinant poxviruses to boost a pre-existing CTL response. We have shown that CTL responses can be primed using different antigen delivery systems such as a DNA vaccine i.d. and i.m, a recombinant Ty-VLP, a recombinant adenovirus and irradiated sporozoites. This is supported by the data presented on the generation of a CD8+ T cell response against HIV, influenza virus and tumours. Amongst several known examples of other diseases against which a CD8+ T cell immune response is important are the following: infection and disease caused by the viruses HIV, herpes simplex, herpes zoster, hepatitis C, hepatitis B, influenza, Epstein-Barr virus, measles, dengue and HTLV-1; by the bacteria *Mycobacterium tuberculosis* and Listeria sp.; and by the protozoan parasites Toxoplasma and Trypanosoma. Induction of protective CTL responses against influenza A virus has been demonstrated in FIG. 14. Furthermore, the immunisation regime described herein is expected to be of value in immunising against forms of cancer where CD8+ T cell responses plays a protective role. The induction of protective CTL responses using the DNA prime MVA boost regime against tumours is shown in FIG. 13. Specific examples in humans include melanoma, cancer of the breast and cancer of the colon.

While this invention has been particularly shown and described with references to preferred embodiments thereof, it will be understood by those skilled in the art that various changes in form and details may be made therein without departing from the scope of the invention encompassed by the appended claims.

REFERENCES

1. Nardin E H & Nussenzweig R S. T cell responses to pre-erythrocytic stages of malaria: role in protection and vaccine development against pre-erythrocytic stages. *Annual Review of Immunology* (1993) 11: 687-727.
2. Hill A V S, Allsopp, C E M, Kwiatkowski D, Anstey N M, Twumasi P, Rowe P A, Bennett S, Brewster D, McMichael A J, Greenwood B M. (1991) Common West African HLA antigens are associated with protection from severe malaria. *Nature* 352: 595-600.
3. Aidoo M, Lalvani A, Allsopp C E M, et al. Identification of conserved antigenic components for a cytotoxic T lymphocyte-inducing vaccine against malaria. *The Lancet.* (1995) 345: 1003-1007.
4. Wizel B, Houghten R A, Parker K C, Coligan J E, Church P, Gordon D M, Ballou W R, Hoffman S L. Irradiated sporozoite vaccine induces HLA-B8-restricted cytotoxic T lymphocyte responses against two overlapping epitopes of the *Plasmodium falciparum* sporozoite surface protein 2. *J. Exp Med.* (1995) 182: 1435-45.
5. Lalvani A, Aidoo M, Allsopp C E, Plebanski M, Whittle H C, Hill A V. An HLA-based approach to the design of a CTL-inducing vaccine against *Plasmodium falciparum*. *Research in Immunology* (1994) 145: 461-8.
6. Seguin M C, Klotz F W, Schneider I, Weir J P, Goodbary M, Slayter M, Raney J J, Aniagolu J U, Green S J. Induction of nitric oxide synthase protects against malaria in mice exposed to irradiated *Plasmodium berghei* infected mosquitoes: involvement of interferon gamma and CD8+ T cells. *J. Exp. Med. (*1994) 180: 353-8.
7. Thomas A W, Slierendregt B, Mons B, Druilhe P. Chimpanzees and supporting models in the study of malaria pre-erythrocytic stages. *Mem. Inst. Oswaldo Cruz.* (1994) 89 Suppl 2: 111-4.
8. Sedegah M, Hedstrom R, Hobart P, Hoffman S L. Protection against malaria by immunization with plasmid DNA encoding circumsporozoite protein. *Proc. Natl. Acad. Sci USA.* (1994) 91: 9866-70.

9. Li S, Rodrigues M, Rodriguez D, Rodriguez J R, Esteban M, Palese P, Nussenzweig R S, Zavala F. Priming with recombinant influenza virus followed by administration of recombinant vaccinia virus induces CD8+ T-cell-mediated protective immunity against malaria. *Proc. Natl. Acad. Sci. USA.* (1993) 90: 5214-8.
10. Lanar D E, Tine J A, de-Taisne C, Seguin M C, Cox W I, Winslow J P, Ware L A, Kauffman E B, Gordon D, Ballou W R, Paoletti E, Sadoff J C. Attenuated vaccinia virus-circumsporozoite protein recombinants confer protection against rodent malaria. *Infection and Immunity* (1996) 64: 1666-71.
11. Ogg G S, Jin X, Bonhoeffer S, Dunbar P R, Nowak M A, Monard S, Segal J P, Cao Y, Rowland-Jones S L, Cerundolo et al. Quantitation of HIV-1-specific cytotoxic T lymphocytes and plasma load of viral RNA. *Science* (1998) 279: 2103-6.
12. Ada G. Do cytotoxic T lymphocytes clear some HIV/SIV infections? *Journal of Medical Primatology* (1996) 25: 158-62.
13. Gallimore A, Cranage M, Cook N, Almond N, Bootman J, Rud E, Silvera P, Dennis M, Corcoran T, Stott J et-al Early suppression of SIV replication by CD8+ nef-specific cytotoxic T cells in vaccinated macaques. *Nature Medicine* (1995) 1: 1167-73.
14. Mayr A, Hochstein-Mintzel V, Stickl H. *Infection* (1975) 33: 6-14.
15. Mayr A, *Zentralbl Veterinarmed B* (1976) 23: 417-30.
16. Mayr A, Stickl H., Muller H K, Danner K, Singer H. *Zentralbl Bakteriol B.* (1978)167: 375-90.
17. Stickl H, Hochstein-Mintzel V, Mayr A, Huber H C, Schafer H, Holzner A. *Dtsch Med Wochenschr.* (1974) 99: 23866-922.
18. Mahnel H, Mayr A. *Berl Munch Tierarztl Wochenschr* (1994) 107: 253-6.
19. Meyer H, Sutter G, Mayr A. *J Gen Virol.* (1991) 72: 1031-8.
20. Altenburger W, Suter C P, Altenburger J. *Arch Virol.* (1989) 105: 15-27.
21. Sutter G, Ramsey-Ewing A, Rosales R, Moss B. *J. Virol.* (1994) 68: 4109-16.
22. Sutter G, Moss B. *Proc Natl Acad Sci USA* (1992) 89: 10847-51.
23. Sutter G W, Wyatt L S, Foley P L, Bennink J R, Moss B. *Vaccine* (1994). 12: 1032-40.
24. Hirsch V M, Goldstein S, Channock R, et al. *Channock R. ed Vaccines* 95. Cold Spring Harbor Laboratory Press, (1995) 195-200.
25. Hirsch V M, Fuerst T R, Sutter G, et al. *J. Virol.* (1996) 70: 3741-52.
26. Moss B, Carroll M W, Wyatt L, et al. *In: Anonymous, ed. Vaccines: Novel strategies in design and production.* Plenum Pres (1995).
27. Symons J A, Alcami A, Smith G L. *Cell.* (1995) 81: 551-60.
28. Alcami A, Smith G L. *J. Virol.* (1995) 69: 4633-9.
29. Alcami A, Smith G L. *Cell.* (1992) 71: 153-67.
30. Graham K A et al. *Virology* (1997) 229: 12-24.
31. Alcami A, Smith G L. *Proc. Natl. Acad. Sci. USA* (1996) 93:11029-34.
32. Blanchard T J, Rowland-Jones S, Gotch F, McMichael A J, Smith G L. *Lancet* (1997) 348:1741.
33. McLean C S, Erturk M, Jennings R, Challanain D N, Minson A C, Duncan I, Boursnell M E, Inglis S C. *J. Infect. Dis.* (1994) 170(5): 1100-9.
34. Davis N L, Brown K W, Johnston R E, *J. Virol,* (1996) 70(6): 3781-7.
35. Layton G T, Harris S J, Myhan J, West D, Gotch F, Hill-Perkins M, Cole J S, Meyers N, Woodrow S, French T J, Adams S E, Kingsman A J. Induction of single and dual cytotoxic T-lymphocyte responses to viral proteins in mice using recombinant hybrid Ty-virus-like particles. *Immunology* (1996) 87: 171-8.
36. McGrory-W J; Bautista-D S; Graham-F L A simple technique for the rescue of early region I mutations into infectious human adenovirus type 5. *Virology* (1988) 163: 614-7.
37. Rodrigues E G, Zavala F, Eichinger D, Wilson J M, Tsuji M. Single immunizing dose of recombinant adenovirus efficiently induces CD8+ T cell-mediated protective immunity against malaria. *Journal of Immunology* (1997) 158: 1268-74.
38. Davis H L, Michel M L, Whalen R G. DNA-based immunization induces continuous secretion of hepatitis B surface antigen and high levels of circulating antibody. *Human Molecular Genetics* (1993) 2: 1847-51.
39. Miyahira Y, Murata K, Rodriguez D et al. Quantification of antigen specific CD8+ T cells using an ELISPOT assay. *J Immunol Methods* (1995) 18: 45-54.
40. Allsopp C E M, Plebanski M, Gilbert S et al. (1996) Comparison of numerous delivery systems for the induction of cytotoxic T lymphocytes. *European Journal of Immunology* (1996) 26:1951-1959.
41. Rodrigues E G, Zavala F, Eichinger D, Wilson J M, Tsuji M. Single immunizing dose of recombinant adenovirus efficiently induces CD8+ T cell-mediated protective immunity against malaria. *J. Immunol.* (1997) 158: 1268-74.
42. Schodel F, Wirtz R, Peterson D, Hughes J, Warren R, Sadoff J, Milich D. Immunity to malaria elicited by hybrid hepatitis B virus core particles carrying circumsporozoite protein epitopes. *J. Exp. Med.* (1994) 180: 1037-46.
43. Satchidanandam V, Zavala F, Moss B. Studies using a recombinant vaccinia virus expressing the circumsporozoite protein of *Plasmodium berghei*. *Mol. Biochem. Parasitol.* (1991) 48: 89-99.
44. Davis J R; Murphy J R; Baqar S; Clyde D F; Herrington D A; Levine M M. Estimate of anti-Plasmodium falciparum sporozoite activity in humans vaccinated with synthetic circumsporozoite protein (NANP)3. *Transactions of the Royal Society for Tropical Medicine and Hygiene.* (1989) 83: 748-50.
45. Meyer, H., Sutter, G. and Mayr, A. (1991). Mapping of deletions in the genome of the highly attenuated vaccinia virus MVA and their influence on virulence. *J. Gen. Virol.* 72: 1031-38.
46. Sutter G, Wyatt L S, Foley P L, Bennink J R, Moss B. A recombinant vector derived from the host range-restricted and highly attenuated MVA strain of vaccinia virus stimulates protective immunity in mice to influenza virus. *Vaccine* (1994) 12: 1032-40.
47. Doolan D L, Sedegah M, Hedstrom R C, Hobart P, Charoenvit Y, Hoffman, S L Circumventing genetic restriction of protection against malaria with multigene DNA immunization: CD8+ cell-, interferon gamma-, and nitric oxide-dependent immunity. *J. Exp. Med.* (1996) 183: 1739-46.
48. Muller H M, Reckmann I, Hollingdale M R, Bujard H, Robson K J, Crisanti A. Thrombospondin related anonymous protein (TRAP) of *Plasmodium falciparum* binds specifically to sulfated glycoconjugates and to HepG2 hepatoma cells suggesting a role for this molecule in sporozoite invasion of hepatocytes. *EMBO-J.* (1993) 12: 2881-9.

49. Chakrabarti S et al. *Mol. Cell. Biol.* (1995) 5: 3403-9.

50. Morrison H G, Bauer S P, Lange J V, Esposito J J, McCormick J B, Auperin D D Protection of guinea pigs from Lassa fever by vaccinia virus recombinants expressing the nucleoprotein or the envelope glycoproteins of Lassa virus. *Virology.* (1989) 171: 179-88.

51. Mackett M et al. *J. Virol.* (1984) 49: 857-864.

52. Carroll M W and Moss B E, *Biotechnology* (1995) 19: 352-4.

What is claimed is:

1. A method for generating a CD8+ T cell immune response in a human against melanoma comprising administering to said human at least one dose of each of the following:
   (i) a priming composition comprising one or more CD8+ T cell epitopes of melanoma, which are present in, or encoded by, a non-viral vector, or a viral vector that is non-replicating or replication-impaired in the human; and
   (ii) a boosting composition comprising a recombinant poxvirus vector encoding at least one of said one or more CD8+ T cell epitopes of melanoma, wherein the recombinant poxvirus vector is non-replicating or replication-impaired in the human;
   wherein the viral vector in (i) is derived from a different virus than the viral vector in (ii),
wherein the CD8+ T cell immune response against melanoma provides a positive clinical outcome in the human.

2. The method of claim 1 wherein the non-replicating or replication-impaired recombinant poxvirus vector in the boosting composition is a recombinant vaccinia virus.

3. The method of claim 2 wherein the recombinant vaccinia virus is a recombinant MVA vector.

4. The method of claim 1 wherein the non-replicating or replication-impaired recombinant poxvirus vector in the boosting composition is a recombinant avipox virus.

5. The method of claim 4 wherein the recombinant avipox virus is a recombinant fowlpox vector.

6. The method of claim 4 wherein the recombinant avipox virus is a recombinant canarypox vector.

7. The method of claim 6 wherein the recombinant canarypox vector is a recombinant ALVAC vector.

8. The method of claim 1 wherein the priming composition is a recombinant DNA plasmid.

9. The method of claim 1 wherein the priming composition is a non-viral vector.

10. The method of claim 1 wherein the priming composition is a non-replicating viral vector or a replication-impaired viral vector.

11. The method of claim 1 wherein the boosting composition of (ii) is delivered intravenously, intraepidermally, intramuscularly, subcutaneously or intradermally.

12. The method of claim 1 which further comprises administering an adjuvant.

13. A method for generating a CD8+ T cell immune response in a human against melanoma comprising administering to said human at least one dose of each of the following:
   (i) a priming composition comprising a DNA plasmid encoding one or more CD8+ T cell epitopes of melanoma; and
   (ii) a boosting composition comprising a recombinant vaccinia virus encoding at least one of said one or more CD8+ T cell epitopes of melanoma, wherein the recombinant vaccinia virus is non-replicating or replication-impaired in the human,
wherein the CD8+ T cell immune response against melanoma provides a positive clinical outcome in the human.

14. The method of claim 13 wherein the non-replicating or replication-impaired recombinant vaccinia virus is a recombinant MVA vector.

15. A method for generating a CD8+ T cell immune response in a human against melanoma comprising administering to said human at least one dose of each of the following:
   (i) a priming composition comprising a DNA plasmid encoding one or more CD8+ T cell epitopes of melanoma; and
   (ii) a boosting composition comprising a recombinant avipox virus encoding at least one of said one or more CD8+ T cell epitopes of melanoma,
wherein the CD8+ T cell immune response against melanoma provides a positive clinical outcome in the human.

16. The method of claim 15 wherein the recombinant avipox virus is a recombinant fowlpox vector.

17. The method of claim 15 wherein the recombinant avipox virus is a recombinant canarypox vector.

18. The method of claim 17 wherein the recombinant canarypox vector is a recombinant ALVAC vector.

19. A method for generating a $CD8^+$ T cell immune response in a human against melanoma comprising administering to said human at least one dose of each of the following:
(i) a priming composition comprising a DNA plasmid encoding one or more $CD8^+$ T cell epitopes of melanoma; and
(ii) a boosting composition comprising a recombinant poxvirus vector encoding at least one of said one or more $CD8^+$ T cell epitopes of melanoma, wherein the recombinant poxvirus vector is non-replicating or replication-impaired in the human;

wherein the $CD8^+$ T cell immune response against melanoma provides a positive clinical outcome in the human.

20. The method of claim 19 wherein the boosting composition of (ii) is delivered intravenously, intraepidermally, intramuscularly, subcutaneously or intradermally.

21. The method of claim 19 which further comprises administering an adjuvant.

22. The method of claim 13 wherein the boosting composition of (ii) is delivered intravenously, intraepidermally, intramuscularly, subcutaneously or intradermally.

23. The method of claim 13 which further comprises administering an adjuvant.

24. The method of claim 15 wherein the boosting composition of (ii) is delivered intravenously, intraepidermally, intramuscularly, subcutaneously or intradermally.

25. The method of claim 15 which further comprises administering an adjuvant.

26. The method of claim 1 wherein the $CD8^+$ T cell immune response against melanoma increases survival in the human.

27. The method of claim 13 wherein the $CD8^+$ T cell immune response against melanoma increases survival in the human.

28. The method of claim 15 wherein the $CD8^+$ T cell immune response against melanoma increases survival in the human.

29. The method of claim 19 wherein the $CD8^+$ T cell immune response against melanoma increases survival in the human.

* * * * *

UNITED STATES PATENT AND TRADEMARK OFFICE
CERTIFICATE OF CORRECTION

PATENT NO. : 7,514,087 B2 Page 1 of 1
APPLICATION NO. : 10/833439
DATED : April 7, 2009
INVENTOR(S) : Andrew McMichael et al.

It is certified that error appears in the above-identified patent and that said Letters Patent is hereby corrected as shown below:

On the Title Page
Item 54, Line 2, delete "IMMUNIZATION" and insert --VACCINATION--.

In Column 1
Line 2, delete "IMMUNIZATION" and insert --VACCINATION--.

Signed and Sealed this

Twenty-third Day of June, 2009

JOHN DOLL
*Acting Director of the United States Patent and Trademark Office*